(12) United States Patent
Ammon, Jr.

(10) Patent No.: US 6,864,098 B2
(45) Date of Patent: Mar. 8, 2005

(54) QUANTITATIVE MALDI-TIME OF FLIGHT MASS SPECTROMETRY OF PEPTIDES AND PROTEINS

(75) Inventor: Daniel M. Ammon, Jr., Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 441 days.

(21) Appl. No.: 09/876,412

(22) Filed: Jun. 7, 2001

(65) Prior Publication Data

US 2002/0031773 A1 Mar. 14, 2002

Related U.S. Application Data

(60) Provisional application No. 60/210,074, filed on Jun. 7, 2000.

(51) Int. Cl.$^7$ .............................................. G01N 24/00
(52) U.S. Cl. ........................................ 436/173; 436/86
(58) Field of Search ................................... 436/173, 86

(56) References Cited

PUBLICATIONS

Nelson et al. "Quantitative Determination of Proteins by MALDI–TOF Spectormetry", Anal. Chem., 1994, v. 66, pp. 1408–1415.*
Kingshott et al. "Direct Detection of Proteins Adsorbed on Synthetic Materials by MALDI–MS", Anal. Biochem., 1999, v. 273, pp 156–162.*
Fenselau,C., MALDI MS and Strategies for Protein Analysis, Analytical Chemistry, 1997, 661a–5a.
Wu, K. J., Odom, R. W., Characterizing Synthetic, Analytical Chemistry, Jul. 1, 1998, 456.
Vesting, M. M., Cotter, R. J.; In Time–of–Flight Mass Spectrometry; American Chemical Society Symposium Series 549: Washington, DC, 1994; 211–24.

Griesser, H.J., Study of Protein Adsorption at Monolayer and Sub–Monolayer Levels by Surface–MALDI Spectroscopy, Society for Biomaterials, 1998, San Diego, Ca.

Siuzdak, G., An Automated MALDI Mass Spectrometry Approach for Optimizing Cyclosporin Extraction and Quantitation.

Bornsen, K. O., Mohr, M. D., Are Quantitative Measurements Possible with MALDI–MS?, Analytical Methods and Instrumentation, Wiley, 1995 Vo12, No3, 158–160.

Sporns, P., Abell, D. C., Rapid Quantitation of Potato Glycoalkoids by Matrix–Assisted Laser Desorption/Ionization ToF Mass Spectroscopy, J. Agric. Food Chem. 1996,44, 2292–2296.

Nelson, K. D., Effects on Protein–Surface Interactions on Protein Ion Signal in MALDI Mass Spectrometry., Anal. Chem. 1999, 71, 268–272.

Voyager™ Biospectrometry™ Workstation with Delayed Extraction™ Technology, PE Biosytems Users Guide, 9/96.

Cheng, J., Terrettaz S., Blankman JI., Electrochemical Comparison of HEME Proteins by Insulated Electrode Voltammetry, Israel Journal of Chemistry, 37(2–3):259–266, 1997.

(List continued on next page.)

*Primary Examiner*—Yelena G. Gakh
(74) *Attorney, Agent, or Firm*—John F. Thomas

(57) ABSTRACT

A method of quantitatively analyzing a sample analyte involves performing matrix-assisted laser desorption ionization mass spectrometry on the sample analyte and an internal standard, and comparing the mass spectrometry of the sample analyte with the mass spectrometry of the internal standard.

4 Claims, 19 Drawing Sheets

OTHER PUBLICATIONS

Figure 3:
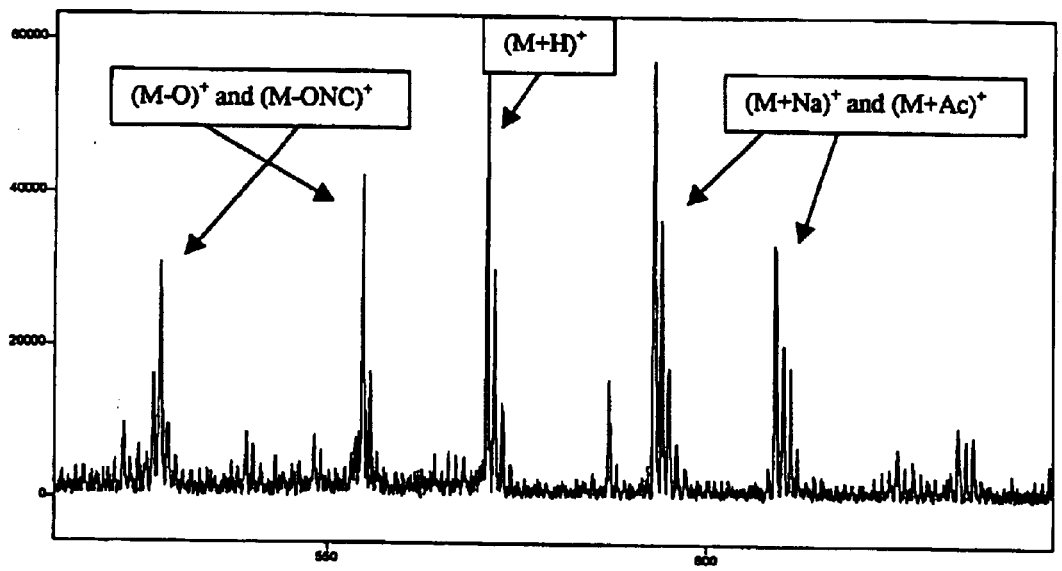

Han, David K., Eng, Jimmy, Zhou, Huilin, Aebersold, Ruedi, Quantitative Profiling of Differentiation–Induced Microsomal Proteins Using Isotope–Coded Affinity Tags and Mass Spectrometry, Nature Biotechnology, vol.: 19, No.: 10, pp. 946–951, Oct. 2001.

Gusev, A. I., Wilkinson, W. R., Proctor, A., Hercules D. M., Quantitaive Analysis of Peptides by Matrix Assisted Laser Desorption/Ionization Time of Flight Spectrometry, Applied Spectroscopy, 1993, vol.: 47, No.: 8, p. 1091–1092.

Gusev, A. I., Wilkinson, W. R., Proctor, A., Hercules D. M., Direct Quantitaive Analysis of Peptides Using Matrix Assisted Laser Desorption/Ionization, Fresenius' Journal of Analytical Chemistry, vol.: 354, No.: 4, p. 455–463, 1996.

Gobom, Johan, Kraeuter, Karl–Otto, Persson, Rita, Steen, Hanno, Roepstorff, Peter, Ekman, Rolf, Detection and Quantification of Neurotension in Human Brain Tissue by Matrix-Assisted Laser Desorption/Ionization Time of Flight Mass Spectrometry, Analytical Chemistry, 72, 3320–3326.

* cited by examiner

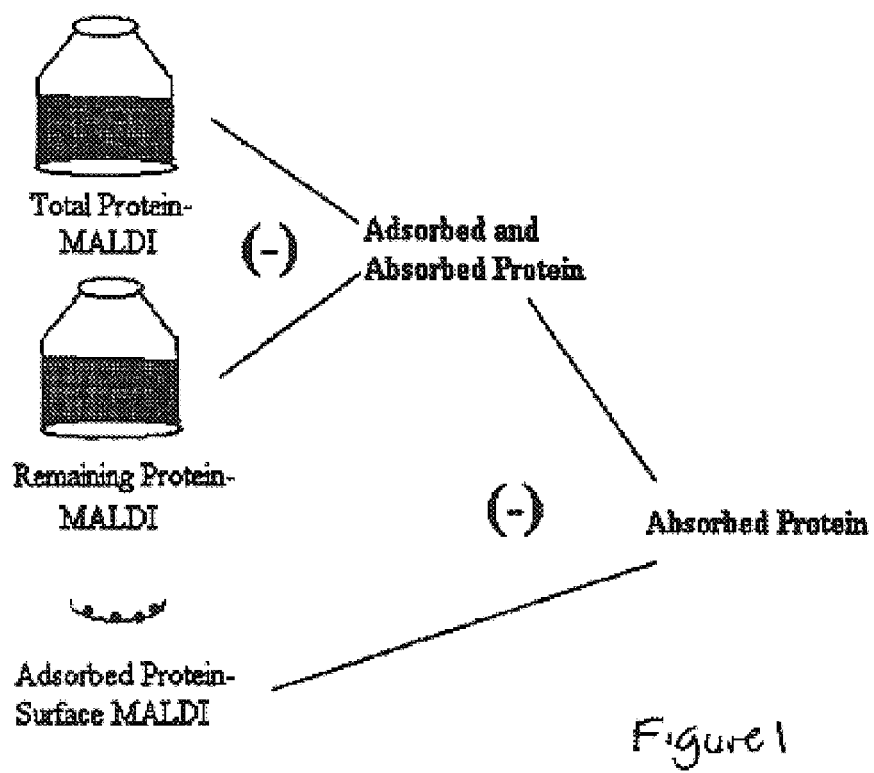
Figure 1
Figure 2
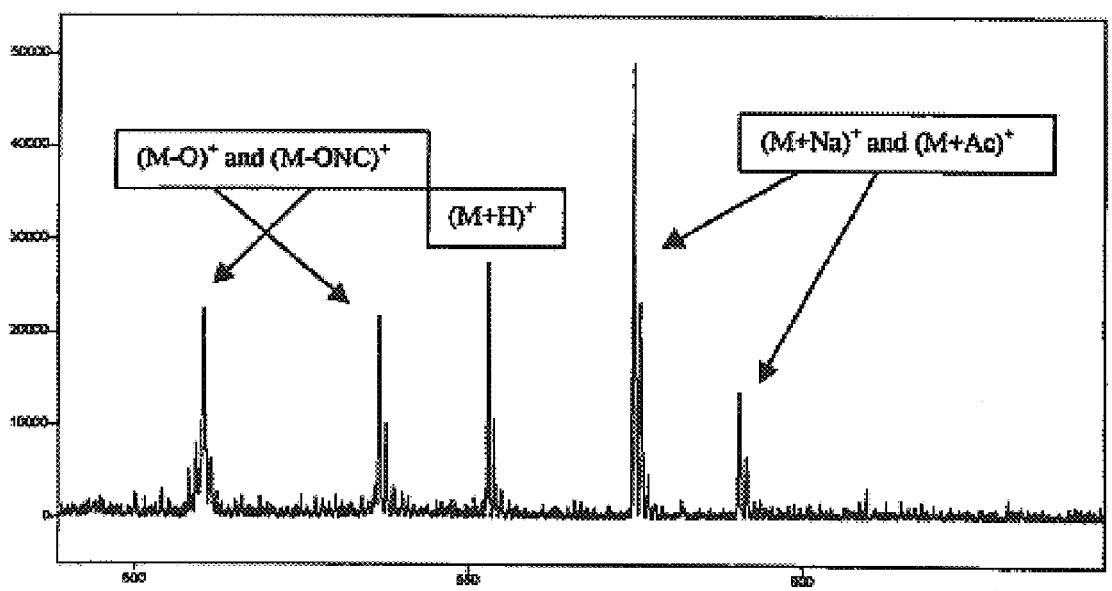

QUANTITATIVE MALDI-TIME OF FLIGHT MASS SPECTROMETRY OF PEPTIDES AND PROTEINS

This application claims the benefit under 35 USC 119(e) of prior provisional application Ser. No. 60/210,074, filed Jun. 7, 2000.

BACKGROUND

Matrix-Assisted Laser Desorption Ionization (MALDI) mass spectrometry is a bioanalytical mass spectrometry technique used to qualitatively analyze peptides and proteins. Fenselau, C., MALDI MS and Strategies for protein Analysis, Analytical Chemistry, 1997, 661a–5a. The technique has also been applied to technical polymers. Wu, K. J., Odom, R. W., Characterizing Synthetic, Analytical Chemistry, Jul. 1, 1998, 456. In MALDI, the sample and a small UV absorbing, Brönsted acidic molecule, the matrix, are dissolved in a solvent and co-crystallized. The matrix and sample are then irradiated with an ultraviolet laser. The matrix, which is in excess, with a molar ratio of 100–10,000:1 to the sample, absorbs the energy from the laser and protonates the sample molecule. Traditionally in mass spectrometry, the energy required to produce ionization of the sample molecule also causes fragmentation. But in MALDI, the matrix absorbs most of the energy from the laser and the sample molecule is desorbed intact. Therefore, the acquired mass spectrum contains few peaks; the molecular ion singly, doubly and triply charged (i.e. $MH^+$, $MH^{+2}$ and $MH^{+3}$) as well as dimers and trimers that are also singly, doubly and triply charged.

The major disadvantage to MALDI is the difficulty in providing quantitative information due to matrix and sample sensitivity. Vesting, M. M., In Time-of-Flight Mass Spectrometry; Cotter, R. J.; American Chemical Society Symposium Series 549: Washington, D.C., 1994; 211–24.

In the experiments reported here calibration curves were constructed for human serum albumin, lactoferrin and lysozyme utilizing cytochrome C as an internal standard. The calibration curves were used to quantify the protein uptake in a biomaterial. The results were compared to an ultra-violet (UV) colorimetric assay. The UV and MALDI results were compared to each other and to theoretical values. The MALDI and UV results were within 15% of each other and theoretical values.

The method of this invention provides for elimination of calibration curves and the implementation of a simple equation. The validity of the equation was confirmed with further experiments utilizing carbonic anhydrase, myoglobin, αlactalbumin and horse albumin with cytochrome C as an internal standard.

Experimental

Several proteins and small peptide fragments were used to demonstrate quantitative MALDI-ToF. The polypeptides, all purchased from Sigma Aldrich, were: Bovine Lactoferrin, Human Serum Albumin, Hen Egg Lysozyme, Horse Albumin, Bovine Carbonic Anhydrase, Bovine αLactalbumin, Horse Heart Myoglobin and YGGFM-NH2, Table 1. The internal standard method was used to construct calibration curves. Bovine Cytochrome C and YGGFL-NH2 were used as the internal standards (IS) for large proteins and peptides, respectively, also listed in Table 1. Man-made protein solutions were prepared to obtain MALDI-ToF mass spectra. The proteins were dissolved in a ternary(ter)-solvent system of acetonitrile, 3-morpholinepropanesulfonic acid (MOPS) buffer (7.2 pH) and 3.0% trifluoroacetic acid (TFA) in a 5:4:1(v:v:v) ratio. The MOPS buffer had a concentration of 4 g/L containing salt concentrations of 10 g/L.

TABLE 1

Protein Reference Information

| Polypeptide | Species | Molecular Weight (KD) | Text Symbol |
|---|---|---|---|
| Lactoferrin | Bovine | 78.0 | La |
| Albumin | Human | 66.4 | Has |
| Lysozyme | Hen Egg | 14.3 | L |
| Albumin | Horse | 65.7 | Al |
| Albumin | Bovine | 65.0 | BSA |
| Carbonic Anhydrase | Bovine | 29.0 | CA |
| αLactalbumin | Bovine | 14.2 | αL |
| Myoglobin | Horse | 16.9 | M |
| Cytochrome C | Bovine | 12.2 | CC |
| YGGFM-NH2 | Synthetic | 0.572 | YGGFM |
| YGGFL-NH2 | Synthetic | 0.545 | YGGFL |

Sinapinic acid (3,5 dimethoxy-4-hydroxycinnamic acid) was used as the matrix for all of the protein experiments. The matrix solvent system was the same as the protein solvent system: acetonitrile, MOPS and 3.0% TFA (5:4:1). The matrix concentration was about 10.0 mg/ml. Alphacyano-4-hydroxycinnamic acid was used as the matrix for the peptides. The matrix solvent system again was acetonitrile, MOPS and 3.0% TFA (5:4:1)

The working volumes for the peptides or proteins solutions were usually 1000 ul. The Bovine Cytochrome C, Internal Standard (IS), concentration range was between 0.3–0.6 pmol/ul. Smaller concentrations of the internal standard were used as the analyte molecular weight increased. This was done so as not to saturate the detector with the smaller IS molecule. The three proteins in which calibration curves were constructed were L, HSA and La. The concentration ranges examined for these proteins were between 1.0–7.0 pmol/ul. A stock solution of acetonitrile, MOPS and 3.0% TFA (5:4:1) was prepared daily for dilution of the protein solutions.

Custom oligonucleotides were prepared by SigmaGenosys; $(ATCG)_5$-TC and $(ATCG)_7$-AC. The solvent system used for the oligonucleotides was a 1:1 acetonitrile:water mixed 8:1 with a 50 mg/ml ammonium citrate in DI water solution, the matrix was 3-HPA.

MALDI Calibration Curves

Peptide Calibration Curve

Solutions were prepared to construct calibration curves for methionine enkephalinamide (YGGFM) utilizing leucine enkephalinamide (YGGFL) as the internal standard. The molecular weight of YGGFL was 554.6 D but with the associated acetate salt, 614.6 D. The molecular weight of YGGFM was 572.7 D but with the associated acetate salt, 632.7 D. Alphacyano-4-hydroxycinnamic acid was used as the matrix for this experiment. The matrix was weighed out to 0.0183 g and diluted in a ternary solvent system, containing acetonitrile, MOPS and 3.0% TFA (5:4:1), to 15.3 mg/ml. Stock solutions of each peptide were prepared from 0.0010 g of YGGFL and 0.0016 g of YGGFM. They were diluted to $1.6 \times 10^{-11}$ mole/ul and $2.5 \times 10^{-11}$ mole/ul, respectively. From these stock solutions various amounts (2–25 ul) were added to 20 ul of matrix solution. The result was five solutions containing different amounts of each peptide. The final concentrations and concentration ratios are in Table 2. Several samples containing two micoliters of each solution were dried on a sample plate for one hour before analysis.

The instrumental conditions for peptide analysis in this molecular weight range were developed by the manufacturer. (Voyager™ Biospectrometry™ Workstation with Delayed Extraction™ Technology, PE Biosystems users Guide, September, 1996). The instrumental conditions were optimized by the manufacture based on resolution. The experiment was performed in linear mode with a mass range between 250–10,000 D. The laser power was chosen such that the optimal signal to noise was achieved, fragmentation was minimized and that detector sensitivity was consistent. The laser power was 1602, the pulse delay time was 100 ns, the accelerating voltage was 20 KV, the grid voltage was at 13 KV and the guide wire voltage was at 1.0 KV.

TABLE 2

Final Concentrations for YGGFL and YGGFM

| Solution | [YGGFL]X10$^{-12}$ mole/ul | [YGGFM]X10$^{-12}$ mole/ul | [YGGFM]/ [YGGFL] |
|---|---|---|---|
| Solution 2A | 1.23 | 3.83 | 3.11 |
| Solution 2B | 1.14 | 5.36 | 4.70 |
| Solution 2C | 1.07 | 6.60 | 6.53 |
| Solution 2D | 0.86 | 10.1 | 11.74 |
| Solution 2E | 0.68 | 13.0 | 19.1 |

This was the only experiment where the internal standard concentration changed. In all other experiments, five different stock solutions for the protein of interest were prepared as well as stock solutions for the internal standard and matrix. In this approach the final volume was keep constant as well as the internal standard concentration and only the polypeptide of interest concentration changed.

Lysozyme (L) Calibration Curves

Solutions were prepared to construct calibration curves for L utilizing CC as the internal standard. Sinapinic acid (3,5 dimethoxy-4-hydroxycinnamic acid) was used as the matrix for this experiment. The matrix was weighed out to 0.0095 g and diluted in a ternary solvent system, containing acetonitrile, MOPS and 3.0% TFA (5:4:1), to 9.5 mg/ml. Stock solutions of each protein were prepared from 0.0019 g of L and 0.0016 g of CC. They were diluted to 1.32×10$^{-10}$ mole/ul and 1.30×10$^{-10}$ mole/ul, respectively, in 1000 ul of the same solvent system mentioned for the matrix. The CC stock solution was diluted 1:10 to 1.30×10$^{-11}$ mole/ul. From the L stock solution four other solutions were made with a 1000 ul working volume. The dilutions were made from 400 ul, 200 ul, 100 ul and 50 ul of the stock solution. The resultant concentrations were 5.28×10$^{-11}$ mole/ul, 2.64×10$^{-11}$ mole/ul, 1.32×10$^{-11}$ mole/ul and 6.6×10$^{-12}$ mole/ul. Two micoliters from L solutions 5A–E were mixed with 40 ul of matrix and 2 ul of the CC diluted stock solution. The final concentrations of the L and CC were shown in Table 5. The L in solutions D and E was below detection limits so one more solution was prepared as to have four data points on the calibration curve. The final solution contained 30 ul of matrix, 2.0 ul L [1.3×10$^{-10}$] mole/ul and 1.5 ul of the diluted CC stock solution. The final concentration in this solution was 5.8×10$^{-13}$ mole/ul of CC and 7.9×10$^{-12}$ mole/ul of L. Several samples, containing two micoliters of each solution, were dried on a sample plate one hour before analysis.

TABLE 3

CC-Dilutions and Concentrations

| Dilution | Dilution Factor | Concentrations (mole/ul) |
|---|---|---|
| 0.0016 g | 1000 ul | 1.3 × 10$^{-10}$ |
| Dilution-1 | 100:1000 | 1.3 × 11$^{-11}$ |
| Dilution-2 | 2:44 | 5.9 × 13$^{-12}$ |

TABLE 4

L-Dilutions and Concentrations

| Initial Concentrations | Dilution Factor | Concentrations (mole/ul) |
|---|---|---|
| 0.0019 g | 1000 ul | 1.3 × 10$^{-10}$ |
| 1.3 × 10$^{-10}$ | 2:44 | 6.0 × 10$^{-12}$ |
| 1.3 × 10$^{-10}$ | 400:1000 & 2:44 | 1.2 × 10$^{-12}$ |
| 1.3 × 10$^{-10}$ | 200:1000 & 2:44 | 1.2 × 10$^{-12}$ |
| 1.3 × 10$^{-10}$ | 100:1000 & 2:44 | 0.60 × 10$^{-12}$ |
| 1.3 × 10$^{-10}$ | 50:1000 & 2:44 | 0.30 × 10$^{-12}$ |

TABLE 5

Final Concentrations and Solution Molar Ratios for CC and L

| Solution | [L]10$^{-12}$mole/ul | [CC]10$^{-13}$mole/ul | [L]/[CC] |
|---|---|---|---|
| Solution 5C | 6.0 | 5.9 | 10.2 |
| Solution 5B | 2.4 | 5.9 | 4.1 |
| Solution 5A | 1.2 | 5.9 | 2.0 |
| Solution 5D | 0.60 | 5.9 | 1.0 |
| Solution 5E | 0.30 | 5.9 | 0.5 |

The instrumental conditions for L analysis in this molecular weight range were developed within this laboratory. The instrumental conditions were optimized based on resolution. The experiment was performed in linear mode with a mass range between 2000–100,000 D. The laser attenuation setting was chosen such that the optimal resolution was achieved, fragmentation was minimized, di or tri-mers formation was minimized and that detector sensitivity was consistent. The laser attenuation setting for L was 2050, the pulse delay time was 150 ns, the accelerating voltage was 25 KV, the grid voltage was at 23.8 KV and the guide wire voltage was at 3.8 KV.

Solutions were prepared to repeat the calibration curve for L utilizing CC as the internal standard. Sinapinic acid (3,5 dimethoxy-4-hydroxycinnamic acid) was used as the matrix for this experiment. The matrix was weighed out to 0.0104 g and diluted in a ternary solvent system, containing acetonitrile, MOPS and 3.0% TFA (5:4:1), to 10.4 mg/ml.

The dilutions and final concentrations of CC and L are shown in Tables 6, 7 and 8. Several samples, containing two micoliters of each solution in Table 8, were dried on a sample plate one hour before analysis.

The instrumental conditions for L analysis were the same as previously mentioned for L.

TABLE 6

CC-Dilutions and Concentrations

| Dilution | Dilution Factor | Concentrations(mole/ul) |
|---|---|---|
| 0.0040 g | 1000 ul | $3.2 \times 10^{-10}$ |
| Dilution-1 | 40:1000 | $1.3 \times 10^{-11}$ |
| Dilution-2 | 2:44 | $5.9 \times 10^{-13}$ |

TABLE 7

L-Dilutions and Concentrations

| Intial Concentrations | Dilution Factor | Concentrations (mole/ul) |
|---|---|---|
| 0.0080 g | 1000 ul | $5.5 \times 10^{-10}$ |
| $5.5 \times 10^{-10}$ | 200:1000 & 2:44 | $5.0 \times 10^{-12}$ |
| $5.5 \times 10^{-10}$ | 150:1000 & 2:44 | $3.8 \times 10^{-12}$ |
| $5.5 \times 10^{-10}$ | 100:1000 & 2:44 | $2.5 \times 10^{-12}$ |
| $5.5 \times 10^{-10}$ | 75:1000 & 2:44 | $1.9 \times 10^{-12}$ |
| $5.5 \times 10^{-10}$ | 50:1000 & 2:44 | $1.3 \times 10^{-12}$ |

TABLE 8

Final Concentrations and Solution Molar Ratios for CC and L

| Solution | [L] × $10^{-12}$ mole/ul | [CC] × $10^{-13}$ mole/ul | [L]/[CC] |
|---|---|---|---|
| Solution 8A | 5.0 | 5.9 | 8.5 |
| Solution 8B | 3.8 | 5.9 | 6.4 |
| Solution 8C | 2.5 | 5.9 | 4.2 |
| Solution 8D | 1.9 | 5.9 | 3.2 |
| Solution 8E | 1.3 | 5.9 | 2.2 |

Human Serum Albumin (HSA) Calibration Curves

Solutions were prepared to construct calibration curve for HSA utilizing CC as the internal standard. Sinapinic acid (3,5 dimethoxy-4-hydroxycinnamic acid) was used as the matrix for this experiment. The matrix was weighed out to 0.0098 g and diluted in a ter solvent system, containing acetonitrile, MOPS and 3.0% TFA (5:4:1), to 9.8 mg/ml.

The dilutions and concentrations of the HSA and CC were shown in Tables 9, 10 and 11. Several samples, containing two microliters of each solution from Table 11, were dried on a sample plate one hour before analysis.

The instrumental conditions for HSA analysis in this molecular weight range were developed within this laboratory. The instrumental conditions were optimized based on resolution. The experiment was performed in linear mode with a mass range between 2000–200,000 D. The laser attenuation setting was chosen such that the optimal resolution was achieved, fragmentation was minimized, di or tri-mers were minimized and that detector sensitivity was consistent. The laser attenuation setting for HSA was 2450, the pulse delay time was 400 ns, the accelerating voltage was 25 KV, the grid voltage was at 23.8 KV and the guide wire voltage was at 3.8 KV.

TABLE 9

CC-Dilutions and Concentrations

| Dilution | Dilution Factor | Concentrations(mole/ul) |
|---|---|---|
| 0.0043 g | 1000 ul | $3.5 \times 10^{-10}$ |
| Dilution-1 & 2 | 100:1000 & 37:100 | $1.3 \times 10^{-11}$ |
| Dilution-3 | 2:44 | $5.9 \times 10^{-13}$ |

TABLE 10

HSA-Dilutions and Concentrations

| Initial Concentrations | Dilution Factor | Concentrations (mole/ul) |
|---|---|---|
| 0.0139 g | 1000 ul | $2.1 \times 10^{-10}$ |
| $2.1 \times 10^{-10}$ | 2:44 | $9.7 \times 10^{-12}$ |
| $2.1 \times 10^{-10}$ | 80:100 & 2:44 | $7.8 \times 10^{-12}$ |
| $2.1 \times 10^{-10}$ | 60:100 & 2:44 | $5.8 \times 10^{-12}$ |
| $2.1 \times 10^{-10}$ | 40:100 & 2:44 | $3.9 \times 10^{-12}$ |
| $2.1 \times 10^{-10}$ | 20:100 & 2:44 | $2.0 \times 10^{-12}$ |

TABLE 11

Final Concentrations and Solution Molar Ratios for CC and HSA

| Solution | [HSA] × $10^{-12}$ mole/ul | [CC] × $10^{-13}$ mole/ul | [HSA]/[CC] |
|---|---|---|---|
| Solution 11A | 9.7 | 5.9 | 16.6 |
| Solution 11B | 7.8 | 5.9 | 13.3 |
| Solution 11C | 5.8 | 5.9 | 9.95 |
| Solution 11D | 3.9 | 5.9 | 6.63 |
| Solution 11E | 2.0 | 5.9 | 3.4 |

Solutions were prepared to repeat the calibration curve for HSA utilizing CC as the internal standard. Sinapinic acid (3,5 dimethoxy-4-hydroxycinnamic acid) was used as the matrix for this experiment. The matrix was weighed out to 0.0100 g and diluted in a ter solvent system, containing acetonitrile, MOPS and 3.0% TFA (5:4:1), to 10.0 mg/ml.

The dilutions and concentrations of the HSA and CC were shown in Tables 12, 13 and 14. Several samples, containing two micoliters of each solution from Table 14, were dried on a sample plate one hour before analysis.

The instrumental conditions for HSA analysis in this molecular weight range were the same as previously discussed.

TABLE 12

CC-Dilutions and Concentrations

| Dilution | Dilution Factor | Concentrations(mole/ul) |
|---|---|---|
| 0.0025 g | 1000 ul | $2.0 \times 10^{-10}$ |
| Dilution-1 | 65:1000 | $1.3 \times 10^{-11}$ |
| Dilution-2 | 2:44 | $5.9 \times 10^{-13}$ |

TABLE 13

HSA-Dilutions and Concentrations

| Initial Concentrations | Dilution factor | Concentrations(mole/ul) |
|---|---|---|
| 0.0192 g | 1000 ul | $3.0 \times 10^{-10}$ |
| $3.0 \times 10^{-10}$ | 2:44 | $13.5 \times 10^{-12}$ |

TABLE 13-continued

HSA-Dilutions and Concentrations

| Initial Concentrations | Dilution factor | Concentrations(mole/ul) |
|---|---|---|
| $3.0 \times 10^{-10}$ | 85:100 & 2:44 | $11.5 \times 10^{-12}$ |
| $3.0 \times 10^{-10}$ | 70:100 & 2:44 | $9.5 \times 10^{-12}$ |
| $3.0 \times 10^{-10}$ | 50:100 & 2:44 | $6.77 \times 10^{-12}$ |
| $3.0 \times 10^{-10}$ | 30:100 & 2:44 | $4.1 \times 10^{-12}$ |

TABLE 14

Final Concentrations and Solution Molar Ratios for CC and HSA

| Solution | [HSA] × $10^{-12}$ mole/ul | [CC] × $10^{-13}$ mole/ul | [HSA]/[CC] |
|---|---|---|---|
| Solution 14A | 13.5 | 5.9 | 22.9 |
| Solution 14B | 11.5 | 5.9 | 19.5 |
| Solution 14C | 9.48 | 5.9 | 16.1 |
| Solution 14D | 6.77 | 5.9 | 11.5 |
| Solution 14E | 4.06 | 5.9 | 6.9 |

Lactoferrin (La) Calibration Curves

Solutions were prepared to construct a calibration curve for La utilizing CC as the internal standard. Sinapinic acid (3,5 dimethoxy-4-hydroxycinnamic acid) was used as the matrix for this experiment. The matrix was weighed out to 0.0115 g and diluted in a ternary solvent system, containing acetonitrile, MOPS and 3.0% TFA (5:4:1), to 11.5 mg/ml.

The dilutions and concentrations of the La and CC were shown in Tables 15, 16 and 17. Several samples, containing two micoliters of each solution from Table 17, were dried on a sample plate one hour before analysis.

The instrumental conditions for La analysis in this molecular weight range were developed within this laboratory. The instrumental conditions were optimized based on resolution. The experiment was performed in linear mode with a mass range between 2000–300,000 D. The laser attenuation setting was chosen such that the optimal signal to noise was achieved, fragmentation was minimized, di or tri-mers were minimized and that detector sensitivity was consistent. The laser attenuation setting for lactoferrin was 2450, the pulse delay time was 200 ns, the accelerating voltage was 25KV, the grid voltage was at 23.3KV and the guide wire voltage was at 5.0KV.

TABLE 15

CC-Dilutions and Concentrations

| Dilution | Dilution Factor | Concentrations(mole/ul) |
|---|---|---|
| 0.0048 g | 1000 ul | $4.0 \times 10^{-10}$ |
| Dilution-1&2 | 200:1000 & 100:1000 | $7.8 \times 10^{-12}$ |
| Dilution-3 | 2:44 | $3.5 \times 10^{-13}$ |

TABLE 16

La-Dilutions and Concentrations

| Initial Concentrations | Dilution Factor | Concentrations(mole/ul) |
|---|---|---|
| 0.0201 g | 1000 ul | $2.5 \times 10^{-10}$ |
| $2.5 \times 10^{-10}$ | 90:200 & 2:44 | $5.1 \times 10^{-12}$ |
| $2.5 \times 10^{-10}$ | 75:200 & 2:44 | $4.3 \times 10^{-12}$ |
| $2.5 \times 10^{-10}$ | 50:200 & 2:44 | $2.9 \times 10^{-12}$ |

TABLE 16-continued

La-Dilutions and Concentrations

| Initial Concentrations | Dilution Factor | Concentrations(mole/ul) |
|---|---|---|
| $2.5 \times 10^{-10}$ | 30:200 & 2:44 | $1.7 \times 10^{-12}$ |
| $2.5 \times 10^{-10}$ | 20:200 & 2:44 | $1.1 \times 10^{-12}$ |

TABLE 17

Final Concentrations and Solution Molar Ratios for CC and La

| Solution | [La] × $10^{-12}$ mole/ul | [CC] × $10^{-13}$ mole/ul | [La]/[CC] |
|---|---|---|---|
| Solution 17A | 5.13 | 3.5 | 13.2 |
| Solution 17B | 4.28 | 3.5 | 11.0 |
| Solution 17C | 2.85 | 3.5 | 7.3 |
| Solution 17D | 1.71 | 3.5 | 4.4 |
| Solution 17E | 1.14 | 3.5 | 2.9 |

Solutions were prepared to repeat the calibration curve for La utilizing CC as the internal standard. Sinapinic acid (3,5 dimethoxy-4-hydroxycinnamic acid) was used as the matrix for this experiment. The matrix was weighed out to 0.0115 g and diluted in a ternary solvent system, containing acetonitrile, MOPS and 3.0% TFA (5:4:1), to 12.2 mg/ml.

The dilutions and concentrations of the La and CC were shown in Tables 18, 19 and 20. Several samples, containing two micoliters of each solution from Table 20, were dried on a sample plate one hour before analysis.

The instrumental conditions for La analysis in this molecular weight range were the same as discussed above.

TABLE 18

CC-Dilutions and Concentrations

| Dilution | Dilution Factor | Concentrations(mole/ul) |
|---|---|---|
| 0.0049 g | 1000 ul | $4.0 \times 10^{-10}$ |
| Dilution-1&2 | 195:1000 & 100:1000 | $7.8 \times 10^{-12}$ |
| Dilution-3 | 2:44 | $3.5 \times 10^{-13}$ |

TABLE 19

La-Dilutions and Concentrations

| Initial Concentrations | Dilution Factor | Concentraions(mole/ul) |
|---|---|---|
| 0.0214 g | 1000 ul | $2.7 \times 10^{-10}$ |
| $2.7 \times 10^{-10}$ | 90:200 & 2:44 | $5.5 \times 10^{-12}$ |
| $2.7 \times 10^{-10}$ | 75:200 & 2:44 | $4.6 \times 10^{-12}$ |
| $2.7 \times 10^{-10}$ | 50:200 & 2:44 | $3.0 \times 10^{-12}$ |
| $2.7 \times 10^{-10}$ | 30:200 & 2:44 | $1.8 \times 10^{-12}$ |
| $2.7 \times 10^{-10}$ | 20:200 & 2:44 | $1.2 \times 10^{-12}$ |

TABLE 20

Final Concentrations and Solution Molar Ratios for CC and La

| Solution | [La] × $10^{-12}$ mole/ul | [CC] × $10^{-13}$ mole/ul | [La]/[CC] |
|---|---|---|---|
| Solution 20A | 5.47 | 3.5 | 15.6 |
| Solution 20B | 4.56 | 3.5 | 13.0 |
| Solution 20C | 3.04 | 3.5 | 8.8 |
| Solution 20D | 1.82 | 3.5 | 5.2 |
| Solution 20E | 1.22 | 3.5 | 3.5 |

UV Calibration Curves
Bicinchoninic Acid BSA Method

The UV experiments were performed on a Shimadzu UV 1606 model spectrometer. UV calibration curves were constructed based on a colorimetric assay developed by Sigma. Generally, a protein in the presence of $Cu^{+2}$ forms a tetradenate-Cu+1 complex. The complex then binds with two bicinchoninic acid (BCA) molecules to form the final purple color complex, BCA–Cu+1 ternary complex. More specifically there are three solutions involved in performing this experiment. Solution 3 is a bovine serum albumin (BSA) standard solution with a concentration of 2 mg/ml. The solvent system is an aqueous system with 0.9% saline and 0.05% sodium azide. Solution 2 is a 4.0% cupric sulfate solution. Solution 1 contains sodium carbonate, sodium bicarbonate, bicinchoninic acid and sodium tartrate in 0.2N sodium hydroxide. Solutions 1 and 2 are mixed together in a 50 to 1 part ratio, respectively. For a standard calibration curve, two milliliters are placed in six test tubes with varying amount of solution 3 to produce six solutions containing five different concentrations of BSA. One solution contains no protein, a blank. The solutions are then processed at 37° C. for 15 minutes, cooled and the absorbance measured. The absorbance, a purple color at 562 nm, versus concentration calibration curve is linear over a 2 ug/ml to 2000 ug/ml concentration range.

Protein Calibration Curves by UV Analysis

UV calibration curves were not performed with peptides because the MALDI calibration curve was not applied to any peptide experiments.

Calibration curves for L were constructed in duplicate utilizing the BCA/BSA method developed by Sigma. There was one exception to the method previously mentioned, instead of utilizing the standard BSA protein solution, provided by Sigma, L was used as the standard solution at a 1.0 mg/ml concentration in MOPS buffer. Typically, the BCA/BSA calibration curve is constructed and only approved proteins can be applied to the calibration curve. Approved proteins interact with the copper and BCA in equivalent molar relative to BSA. L is not an approved protein for this method. The copper and BCA binding response may not be one molecule of BSA to one molecule of L. To eliminate this possibility, L was used to construct a calibration curve to analyzed L sample solutions.

The L stock solution was prepared by weighing 10 mg of L and diluting it in 10 ml of MOPS buffer for a final concentration of 1 mg/ml. Solution 2 is a 4.0% cupric sulfate solution. Solution 1 contains sodium carbonate, sodium bicarbonate, bicinchoninic acid and sodium tartrate in 0.2N sodium hydroxide. Solutions 1 and 2 are mixed together in a 50 to 1 part ratio, respectively, to produce a BCA stock solution. Two milliliters of the BCA stock solution was placed into six vials. In each vial containing the BCA stock solution, 0 ul, 2 ul, 5 ul, 10 ul, 20 ul and 50 ul of the L stock solutions were added. The final concentrations are listed in Table 21. The solutions were incubated for 30 minutes at 37° C., cooled and the absorbance measured.

TABLE 21

Final L Concentrations for the UV Calibration Curve

| Solution | [L] ug/ml |
| --- | --- |
| Solution 21A | 0.0 |
| Solution 21B | 1.0 |
| Solution 21C | 2.5 |

TABLE 21-continued

Final L Concentrations for the UV Calibration Curve

| Solution | [L] ug/ml |
| --- | --- |
| Solution 21D | 5.0 |
| Solution 21E | 10.0 |
| Solution 21F | 25.0 |

Calibration curves for HSA were constructed in duplicate utilizing the BCA/BSA method developed by Sigma. There was one exception to the method previously mentioned, instead of utilizing the standard BSA protein solution, provided by Sigma, HSA was used as the standard solution at a 2.0 mg/ml concentration in MOPS buffer. Typically, the BCA/BSA calibration curve is constructed and only approved proteins can be applied to the calibration curve. Approved proteins interact with the copper and BCA in equivalent molar relative to BSA. HSA is not an approved protein for this method. The copper and BCA binding response may not be one molecule of BSA to one molecule of HSA. To eliminate this possibility, HSA was used to construct a calibration curve to analyzed HSA sample solutions.

The HSA stock solution was prepared by weighing 20 mg of HSA and diluting it in 10 ml of MOPS buffer for a final concentration of 2 mg/ml. Solution 2 is a 4.0% cupric sulfate solution. Solution 1 contains sodium carbonate, sodium bicarbonate, bicinchoninic acid and sodium tartrate in 0.2N sodium hydroxide. Solutions 1 and 2 are mixed together in a 50 to 1 part ratio, respectively, to produce a BCA stock solution. Two milliliters of the BCA stock solution was placed into six vials. In each vial containing the BCA stock solution, 0 ul, 10 ul, 20 ul, 30 ul, 40 ul and 50 ul of the HSA stock solutions were added. The final concentrations are listed in Table 22. The solutions were incubated for 30 minutes at 37° C., cooled and the absorbance measured.

TABLE 22

Final HSA Concentrations for the UV Calibration Curve

| Solution | [HSA] ug/ml |
| --- | --- |
| Solution 22A | 0.0 |
| Solution 22B | 10.0 |
| Solution 22C | 20.0 |
| Solution 22D | 30.0 |
| Solution 22E | 40.0 |
| Solution 22F | 50.0 |

Calibration curves for La were constructed in duplicate utilizing the BCA/BSA method developed by Sigma. There was one exception to the method previously mentioned, instead of utilizing the standard BSA protein solution, provided by Sigma, La was used as the standard solution at a 2.0 mg/ml concentration in MOPS buffer. Typically, the BCA/BSA calibration curve is constructed and only approved proteins can be applied to the calibration curve. Approved proteins interact with the copper and BCA in equivalent molar relative to BSA. La is not an approved protein for this method. The copper and BCA binding response may not be one molecule of BSA to one molecule of La. To eliminate this possibility, La was used to construct a calibration curve to analyzed La sample solutions.

The La stock solution was prepared by weighing 20 mg of La and diluting it in 10 ml of MOPS buffer for a final concentration of 2 mg/ml. Solution 2 is a 4.0% cupric sulfate solution. Solution 1 contains sodium carbonate, sodium bicarbonate, bicinchoninic acid and sodium tartrate in 0.2N sodium hydroxide. Solutions 1 and 2 are mixed together in a 50 to 1 part ratio, respectively, to produce a BCA stock solution. Two milliliters of the BCA stock solution was placed into six vials. In each vial containing the BCA stock solution, 0 ul, 10 ul, 20 ul, 30 ul, 40 ul and 50 ul of the La stock solutions were added. The final concentrations are listed in Table 10. The solutions were incubated for 30 minutes at 37° C., cooled and the absorbance measured.

TABLE 23

Final La Concentrations for the UV Calibration Curve

| Solution | [La] ug/ml |
|---|---|
| Solution 23A | 0.0 |
| Solution 23B | 10.0 |
| Solution 23C | 20.0 |
| Solution 23D | 30.0 |
| Solution 23E | 40.0 |
| Solution 23F | 50.0 |

Sample Preparation for the Application of the Calibration Curves

Experimental Outline

This section will discuss the sample preparations for the application of the MALDI and UV calibration curves to determine the adsorption and absorption of HSA, La and L onto and into contact lens materials. An experimental illustration is shown in FIG. 1. The experimental outline will be generally discussed here and specifically discussed for each protein and technique in the next sections. Generally, sample vials labeled Total Protein and Remaining Protein in FIG. 1 were the same protein solution with the exception that the vial labeled Remaining Protein had an ACCUVUE™ contact lens placed in it. The ACCUVUE™ contact lens material is composed of 98% hydroxethylmethacrylate (HEMA) and 2% methacrylic acid. The L solution had a concentration of 0.6 mg/ml, the HSA and La solutions were both 2.0 mg/ml. A solution mixture containing 2.0 mg/ml and 0.6 mg/ml of HSA and L was also evaluated. All vials contained 1.5 ml of solution. Both solution samples were incubated at 37° C. for 48 hours, cooled and analyzed by the UV colorimetric assay and MALDI. The difference in protein content between the two solutions would be the total protein adsorbed and absorbed onto and into the contact lens material. The contact lens was then removed and analyzed by surface MALDI to determine adsorbed protein. The difference between the adsorbed protein onto the lens and the adsorbed/absorbed result provided the answer to total absorbed protein.

Sample Preparations for L Uptake by a Contact Lens Material

The sample preparation for the application of the L calibration curves to the absorption and adsorption of L into and onto a contact lens material is now discussed utilizing CC as the internal standard via MALDI. Sinapinic acid was weighed out to 0.010 g and diluted to 10.0 mg/ml. A stock solution of the internal standard, CC, was prepared from 0.0021 g and diluted to a concentration of 11.9 pmol/ul. The final solutions were prepared from 40 ul of the matrix solution, 2 ul of the CC solution and 2 ul of the solutions labeled either Total Protein or Remaining Protein. The final CC concentration was 0.541 pmol/ul. Two micoliters of each solution were dried on a sample plate for one hour before analysis.

A second set of solutions were prepared to analyze for L deposition into and onto a contact lens material utilizing CC as the internal standard via MALDI. Sinapinic acid was weighed out to 0.0099 g and diluted in the usual ternary solvent system and diluted to 9.9 mg/ml. A stock solution of the internal standard, CC, was prepared from 0.0034 g and diluted to a concentration of 13.8 pmol/ul. The final solution was prepared from 40 ul of the matrix solution, 2 ul of the CC solution and either 2 ul of the solutions labeled Total Protein or Remaining Protein. The final CC concentration was 0.627 pmol/ul.

The instrumental conditions for analysis of either the Total Protein samples or the Remaining Protein samples were the same as mentioned for the MALDI Calibration Curves.

The L deposition solutions for UV analysis were the same samples analyzed by MALDI. The BCA stock solution was prepared as per the UV calibration Curves. Twenty micoliters from either the Total Protein or Remaining Protein solutions were mixed with BCA stock solution. The solutions were incubated for 30 minutes at 37° C., cooled and the absorbance measured.

Sample Preparations for HSA Uptake by a Contact Lens Material

The sample preparation for the application of the HSA calibration curves to the absorption and adsorption of HSA into and onto a contact lens material is now discussed. Solutions were prepared to quantitate HSA solutions utilizing CC as the internal standard via MALDI. Sinapinic acid was weighed out to 0.0098 g and diluted to 9.8 mg/ml. A stock solution of the internal standard, CC, was prepared from 0.0049 g and diluted to a concentration of 11.9 pmol/ul. The final solution was prepared from 40 ul of the matrix solution, 2 ul of the CC solution and 2 ul of the solutions labeled either Total Protein or Remaining Protein. The final CC concentration was 0.543 pmol/ul. Two micoliters of each solution were dried on a sample plate for one hour before analysis.

A second set of solutions were prepared to quantitate HSA deposition utilizing CC (bovine) as the internal standard via MALDI. Sinapinic acid was weighed out to 0.010 g and diluted to 10.0 mg/ml. A stock solution of the internal standard, CC, was prepared from 0.0042 g and diluted to a concentration of 10.2 pmol/ul. The final solution was prepared from 40 ul of the matrix solution, 2 ul of the CC solution and either 2 ul of the solutions labeled Total Protein or Remaining Protein. The final CC concentration was 0.465 pmol/ul. Two micoliters of each solution were dried on a sample plate one hour before analysis.

The instrumental conditions for analysis of either the Total Protein samples or the Remaining Protein samples were the same as above.

The HSA deposition solutions for UV analysis were the same samples analyzed by MALDI. The BCA stock solution was prepared as above. Twenty micoliters from either the Total Protein or Remaining Protein solutions were mixed with BCA stock solution. The solutions were incubated for 30 minutes at 37° C., cooled and the absorbance measured.

Sample Preparations for La Uptake by a Contact Lens Material

The sample preparation for the application of the La calibration curves to the absorption and adsorption of La into and onto a contact lens material is now discussed utilizing CC as the internal standard via MALDI. Sinapinic acid was weighed to 0.010 g and diluted to 10.0 mg/ml. A stock solution of the internal standard, CC, was prepared from 0.0031 g and diluted to a concentration of 7.53 pmol/ul. The final solution was prepared from 40 ul of the matrix solution, 2 ul of the cytochrome C solution and 2 ul of the solutions labeled either Total Protein or Remaining Protein. The final CC concentration was 0.342 pmol/ul. Two micoliters of each solution were dried on a sample plate for one hour before analysis.

A second set of solutions were prepared to analyze La deposition into and onto a contact lens material utilizing CC as the internal standard via MALDI. Sinapinic acid was weighed out to 0.0098 g and diluted to 9.8 mg/ml. A stock solution of the internal standard, CC, was prepared from 0.0049 g and diluted to a concentration of 5.95 pmol/ul. The final solution was prepared from 40 ul of the matrix solution, 2 ul of the CC solution and either 2 ul of the solutions labeled Total Protein or Remaining Protein. The final CC concentration was 0.270 pmol/ul. Again, two micoliters of each solution were dried on a sample plate one hour before analysis. The instrumental conditions for analysis of either the Total Protein samples or the Remaining Protein samples were the same as above.

The La deposition solutions for UV analysis were the same samples analyzed by MALDI. The BCA stock solution was prepared as above. Twenty micoliters from either the Total Protein or Remaining Protein solutions were mixed with BCA stock solution. The solutions were incubated for 30 minutes at 37° C., cooled and the absorbance measured.

Sample Preparations for a Mixture of HSA and L Uptake by a Contact Lens Material The sample preparation for the application of a mixture of HSA and L calibration curves to the absorption and adsorption of these proteins into and onto a contact lens material is now discussed utilizing CC as the internal standard via MALDI. Sinapinic acid was weighed out to 0.0099 g and diluted to 9.9 mg/ml. A stock solution of the internal standard, CC, was prepared from 0.0047 g and diluted to a concentration of 11.4 pmol/ul. The final solution was prepared from 40 ul of the matrix solution, 2 ul of the CC solution and either 2 ul of the solutions labeled Total Protein or 4 ul of the solutions labeled Remaining Protein. The final CC concentration was 0.520 pmol/ul. Two micoliters of each solution were dried on a sample plate for one hour before analysis. Twice as many samples were deposited so half could be analyzed using L instrumental conditions and the other half using HSA instrumental conditions.

A second set of solutions were prepared to analyze L and HSA deposition into and onto a contact lens material utilizing CC as the internal standard via MALDI. Sinapinic acid was weighed out to 0.0102 g and diluted to 10.2 mg/ml. A stock solution of the internal standard, CC, was prepared from 0.0045 g and diluted to a concentration of 11.0 pmol/ul. The final solution was prepared from 40 ul of the matrix solution, 2 ul of the CC solution and either 2 ul of the solutions labeled Total Protein or 4 ul of the solutions labeled Remaining Protein. The final CC concentration was 0.498 pmol/ul. Two micoliters of each solution were dried on a sample plate one hour before analysis. Again, twice as many samples were deposited so half could be analyzed using L instrumental conditions and the other half using HSA instrumental conditions. The instrumental conditions for analysis of either the Total Protein samples or the Remaining Protein samples were the same as above for L.

The mixtures of HSA and L deposition solutions for UV analysis were the same samples analyzed by MALDI. The BCA stock solution was prepared as above. Twenty micoliters from either the Total Protein or Remaining Protein solutions were mixed with BCA stock solution. The solutions were incubated for 30 minutes at 37° C., cooled and the absorbance measured.

Sample Preparations for Surface MALDI of Contact Lenses

This section describes the protocol used for sample preparations for the analysis of contact lenses by Surface MALDI is now described. Surface MALDI involves placing matrix directly on the surface of a material and desorbing molecules directly off said surface. In this case ACCUVUE, a contact lens material, was removed from the deposition solution, labeled Remaining Protein, quartered and dried on the sample plate. Two microliters of a solution containing sinapinic acid at a concentration of 10 mg/ml and CC at a concentration of 0.59 pmol/ul in a ter solvent system, containing acetonitrile, MOPS buffer and 3.0% TFA (5:4:1), was deposited on the lens surface and allowed to dry. The surface was analyzed by MALDI under the conditions mentioned for the protein of interest: L, La or HSA.

Quantitative MALDI: the CIM Equation

The CIM Equation

The CIM equation is an equation derived to quantitate proteins by MALDI utilizing fundamental parameters: concentration, peak intensities and protein molecular weight. If shown valid, utilization of the CIM equation could reduce the time of protein quantitative analysis via MALDI by 90% as well explain some of the fundamental aspects of the MALDI process. Calibration curves, for each protein, were constructed from analysis of ion intensities from MALDI spectrum and protein concentration. Calibration curves were constructed by graphing the ratio of the sum of all the sample protein intensities to the sum of all the IS protein intensities (ΣProtein Intensities/ΣIS Intensities) versus the ratio of the concentration of the sample protein to the Concentration of the IS. After the calibration curves were completed, it was observed that the slope of the lines for each protein could be predicted by an equation based on the molecular weight, in kilodaltons, for each protein, equation 1. Table 11 lists the experimental slopes and the predicted slopes for each protein.

$$\text{Slope} = 2.5/MW(\text{Protein in } KD) \qquad 1$$

TABLE 24

Slopes from Protein Calibration Curves

| Protein | Experimental Slope | Predicted Slope |
|---------|--------------------|-----------------|
| L       | 0.19               | 0.17            |
| HSA     | 0.035              | 0.038           |
| La      | 0.025              | 0.031           |

For now, the constant 2.5 is a constant for these three proteins only. The origin of the constant 2.5 will be described in the next few paragraphs but for now the constant 2.5 will be called the phun factor. In an attempt to determine the origin of the phun factor, the entire equation of the line was determined, equation 2. The HSA equation of the line will be used as an example inserting the CIM equation for the slope. For ease, the Y intercept was assumed to be zero.

$$\underbrace{\sum I(HSA)/\sum I(CC)}_{Y} = \underbrace{(2.5/MW(HSA))}_{M} \times \underbrace{([HSA]/[CC])}_{X} \qquad 2$$

HSA=Albumin
CC=Cytochrome C (IS)
[Concentration]
I=MALDI Mass Spectrum Peak Intensities Equation 2 was then rearranged so that the fundamental parameters for HSA were on one side and the fundamentals for CC were on the other side with the phun factor, equation 3.

$$(MW(HSA) \times \Sigma I(HSA))/[HSA] = (2.5 = \Sigma I(CC))/[CC] \qquad 3$$

It can quickly be seen that the two sides contain the same fundamental parameters except for the absence of the molecular weight of CC. The molecular weight was placed into the equation by way of the phun factor. The phun factor was changed from 2.5 to 12.2/5.0 or the molecular weight of CC, 12.2KD, divided by 5.0.

The changed is displayed in equation 4. The phun factor is now 5.0 and both sides of the equation contain all of the fundamental parameters.

$$(MW(HSA) \times \Sigma I(HSA))/[HSA] = (MW(CC) \times \Sigma I(CC))/([CC] \times 5.0) \qquad 4$$

The origin of the phun factor has not been determined but it can be eliminated from the equation by using simple logic. The equation for L is shown in equation 5.

$$(MW(L) \times \Sigma I(L))/[L] = (MW(CC) \times \Sigma I(CC))/([CC] \times 5.0) \qquad 5$$

Since equations 4 and 5 both equal the same CC fundamentals then the two sides equal each other. In other word, eliminating CC as the internal standard to determine HSA fundamentals and using L as the internal standard yields the CIM equation, equation 6. This equation is valid for these three proteins; L, HSA and La. Other proteins and their equations will be discussed in the result and discussion section.

$$(MW(HSA) \times \Sigma I(HSA))/[HSA] = (MW(L) \times \Sigma I(L))/[L] \qquad 6$$

or $$(MW(Sample) \times \Sigma I(Sample))/[Sample] = (MW(IS) \times \Sigma I(IS))/IS \qquad 6$$

There are assumptions underlying the CIM equation. Some assumptions were reasoned from the experimental results while others were derived from experimental procedures. The assumptions derived from experimental procedures were that a mixture of acetonitrile, water and 0.3% TFA is the solvent system and that the matrix is sinapinic acid. Since no other solvent systems or matrices were attempted these may or may not be necessarily universal limitations of the CIM equation. The assumptions derived from experimental results are as follows; the entire sample must be scan averaged, summing peaks intensities is preferable although the use of parent peaks is acceptable, the spectrum should be baseline subtracted, the sample concentration range is between the limit of detection and linear range of the molecule and the molecular weight difference between sample and internal standard should be 30KD or less for large molecules and the samples should ionize on the same functional group. If the internal standard and sample molecules ionize on different functional groups, phun factors should be used to compensate for those differences.

Sample Preparations to Apply the CIM Equation to Horse Albumin (Al)

The sample preparation for the application of the CIM equation is now discussed utilizing horse Al with CC as the internal standard via MALDI. Sinapinic acid was weighed out to 0.0107 g and diluted to 10.7 mg/ml. A stock solution of the internal standard, CC, was prepared from 0.0037 g and diluted to a concentration of 12.0 pmol/ul. Three test samples were prepared by dissolving 0.0030 g, 0.0028 g and 0.0028 g of Al in 1 ml, 0.94 ml and 0.94 ml of MOPS buffer solution. The final solutions were prepared from 40 ul of the matrix solution, 2 ul of the CC solution and 2 ul of the Alsolutions. Each of the three Alsolutions were analyzed at least five times. The final CC concentration was 0.546 pmol/ul. Two microliters of each solution were dried on a sample plate one hour before analysis. The instrumental conditions for Alanalysis were the same as HSA mentioned for the MALDI Calibration Curves.

Sample Preparations to Apply the CIM Equation to Carbonic Anhydrase (CA)

The sample preparation for the application of the CIM equation is now discussed utilizing CA with CC as the internal standard via MALDI. Sinapinic acid was weighed out to 0.0101 g and diluted to 10.1 mg/ml. A stock solution of the internal standard, CC, was prepared from 0.0032 g and diluted to a concentration of 13.0 pmol/ul. Three test samples were prepared by dissolving 0.0021 g, 0.0020 g and 0.0022 g of CA all in 1 ml of MOPS buffer solution. The final solutions were prepared from 40 ul of the matrix solution, 2 ul of the CC solution and 2 ul of the CA solutions. Each of the three CA solutions were analyzed at least five times. The final CC concentration was 0.590 pmol/ul. Two microliters of each solution were dried on a sample plate one hour before analysis. The instrumental conditions for CA analysis were the same as HSA mentioned above.

Sample Preparations to Apply the CIM Equation for αLactalbumin (αL)

The sample preparation for the application of the CIM equation is now discussed utilizing αL with CC as the internal standard via MALDI. Sinapinic acid was weighed out to 0.0098 g and diluted to 9.8 mg/ml. A stock solution of the internal standard, CC, was prepared from 0.0031 g and diluted to a concentration of 12.6 pmol/ul. Three test samples were prepared by dissolving 0.0012 g, 0.0011 g and 0.0011 g of αL all in 1 ml of MOPS buffer solution. The αL was 85% pure. The final solutions were prepared from 40 ul of the matrix solution, 2 ul of the CC solution and 2 ul of the αL solutions. Each of the three αL solutions were analyzed at least five times. The final CC concentration was 0.570 pmol/ul. Two microliters of each solution were dried on a sample plate one hour before analysis. The instrumental conditions for αL analysis were the same as L for the MALDI calibration Curves.

Sample Preparations to Apply the CIM Equation for Myoglobin (M)

The sample preparation for the application of the CIM equation is now discussed utilizing M with CC as the internal standard via MALDI. Sinapinic acid was weighed out to 0.0098 g and diluted to 9.8 mg/ml. A stock solution of the internal standard, CC, was prepared from 0.0031 g and diluted to a concentration of 12.6 pmol/ul. Three test samples were prepared by dissolving 0.0010 g, 0.0012 g and 0.0011 g of M all in 1 ml of MOPS buffer solution. The M was 90% pure. The final solutions were prepared from 40 ul of the matrix solution, 2 ul of the CC solution and 2 ul of the M solutions. Each of the three M solutions were analyzed at least five times. The final CC concentration was 0.570 pmol/ul. Two microliters of each solution were dried on a sample plate one hour before analysis. The instrumental conditions for M analysis were the same as L mentioned above.

Sample Preparations to Apply the CIM Equation to M and αL

The sample preparation for the application of the CIM equation is now discussed utilizing M with αL as the internal standard via MALDI. Sinapinic acid was weighed out to 0.0102 g and diluted to 10.2 mg/ml. Three test samples were prepared by dissolving 0.0033 g, 0.0028 g and 0.0028 g of M in 3.5 ml, 3.2 ml and 3.0 ml, respectively, of MOPS buffer solution. Three different IS solutions were prepares from 0.0035 g, 0.0032 g and 0.0030 g of αL in 3.5 ml, 3.2 ml and 3.0 ml of MOPS buffer, respectively. The final solutions were prepared from 40 ul of the matrix solution, 2 ul of the αL solutions and 2 ul of the M solutions. Each of the M solutions was mixed with the αL respectively. Two micoliters of each solution were dried on a sample plate one hour before analysis. The instrumental conditions for M and αL and analysis were the same as L mentioned above.

Sample Preparations to Apply the CIM Equation to L and A1

The sample preparation for the application of the CIM equation is now discussed utilizing Al with L as the IS via MALDI. Sinapinic acid was weighed out to 0.0104 g and diluted to 10.4 mg/ml. Three test samples were prepared by dissolving 0.0057 g, 0.0057 g and 0.0063 g of Al each in 1 ml of a ternary solvent system, containing acetonitrile, MOPS and 3.0% TFA (5:4:1). Three different IS solutions were prepares from 0.0037 g, 0.0041 g and 0.0058 g of L each in 1 ml of a ter solvent system, containing acetonitrile, MOPS and 3.0% TFA (5:4:1). The first two L solutions were diluted 2:10 and the last 15:100. The final solutions were prepared from 40 ul of the matrix solution, 2 ul of the Al solutions and 2 ul of the L solutions. Each of the Al solutions was mixed with the L solutions respectively. Two micoliters of each solution were dried on a sample plate one hour before analysis. The instrumental conditions for Al and L and analysis were the same as L mentioned above.

Sample Preparations to Apply the CIM Equation to Protein Mixtures(run#1)

The sample preparation for the application of the CIM equation is now discussed utilizing Myo, CA and L with CC as the IS via MALDI. Sinapinic acid was weighed out to 0.010 g and diluted to 10.0 mg/ml. The first test samples were prepared by dissolving 0.0035 g of CC, 0.0029 g of CA, 0.0045 g of L and 0.0017 g of Myo each in 1 ml of a ternary solvent system, containing acetonitrile, MOPS and 3.0% TFA (5:4:1). The solutions were mixed and diluted to a final concentration of $5.98 \times 10^{-13}$ mol/ul of CC, $2.08 \times 10^{-12}$ mol/ul of CA, $1.31 \times 10^{-12}$ mol/ul of L and $8.33 \times 10^{-13}$ mol/ul of Myo. Two micoliters of each solution were dried on a sample plate one hour before analysis. The instrumental parameters were the same as L mentioned above.

Sample Preparations to Apply the CIM Equation to Protein Mixtures(run#2)

The sample preparation for the application of the CIM equation is now discussed utilizing Myo, CA and L with CC as the IS via MALDI. Sinapinic acid was weighed out to 0.010 g and diluted to 10.0 mg/ml. The first test samples were prepared by dissolving 0.0025 g of CC, 0.0028 g of CA, 0.0041 g of L and 0.0021 g of Myo each in 1 ml of a ternary solvent system, containing acetonitrile, MOPS and 3.0% TFA (5:4:1). The solutions were mixed and diluted to a final concentration of $4.38 \times 10^{-13}$ mol/ul of CC, $1.98 \times 10^{-12}$ mol/ul of CA, $1.19 \times 10^{31\ 12}$ mol/ul of L and $6.60 \times 10^{31\ 13}$ mol/ul of Myo. Two micoliters of each solution were dried on a sample plate one hour before analysis. The instrumental parameters were the same as L mentioned above.

Sample Preparations to Apply the CIM Equation to Oligonucleotides

The sample preparation for the application of the CIM equation is now discussed utilizing $(ATCG)_5$-TC (7.0 kD) with $(ATCG)_7$-AC (9.2 kD) as the IS via MALDI. HPA was weighed out to 0.050 g and diluted to 50.0 mg/ml in a 1:1 acetonitrile:water solvent system. Ammonium hydrocitrate was measured to 0.050 g in and diluted to 50 mg/ml in DI water. The HPA solution and ammonium citrate solution were mixed 8:1 respectively. The test samples were prepared by dissolving 191.2 ug of $(ATCG)_5$-TC and 188.1 ug of $(ATCG)_7$-AC each in 100 ul of DI water. The solutions were mixed and diluted to a final concentration of $1.23 \times 10^{-11}$ mol/ul and $8.95 \times 10^{-12}$ mol/ul. Two micoliters of each solution were dried on a sample plate one hour before analysis. A second set of solutions were mixed and diluted to $4.12 \times 10^{-12}$ mol/ul and $4.48 \times 10^{-12}$ mol/ul. The instrumental parameters were optimized based on resolution. The samples were analyzed in positive and negative ion mode.

Sample Analyses

This section discusses the sample analyses of every sample by MALDI-ToF mass spectrometry. The samples were introduced into the ultrahigh vacuum and the pressure was allowed to drop below $1 \times 10^{-7}$ Torr. The laser power was initiated and the entire sample was analyzed by scanning the laser focal point over the sample in a right to left and up and down motion. This scan average analysis has been performed before because of the heterogeneity of the biomolecules distributed in the matrix (Nelson, R. W., Quantitative Determination of Proteins by Matrix-Assisted Laser Desorption/Ionization Time-of-Flight Mass Spectroscopy, Anal. Chem. 1994, 66, 1408–1415; Siuzdak, G., An Automated MALDI Mass Spectrometry Approach for Optimizing Cyclosporin Extraction and Quantitation; Bornsen, K. O., Mohr, M. D., Are Quantitative Measurements Possible with MALDI-MS?, Analytical Methods and Instrumentation, Wiley, 1995 Vol2, No3, 158–160; Spoms, P., Abell, D. C., Rapid Quantitation of Potato Glycoalkoids by Matrix-Assisted Laser Desorption/Ionization Time-of-Flight Spectroscopy, J. Agric. Food Chem. 1996, 44, 2292–2296). Every sample was scan averaged to a total of 50–250 points or until no more sample was detected.

RESULTS AND DISCUSSION

MALDI Calibration Curves

The next few sections will discuss the construction of seven calibration curves. The sample preparations for each calibration curve were outlined previously. Each section here will discuss ion formation and the calibration curve results.

Methionine Enkephalinamide (YGGFM) and Leucine Enkephalinamide (YGGFL)

Calibration Curve

Figure 4:
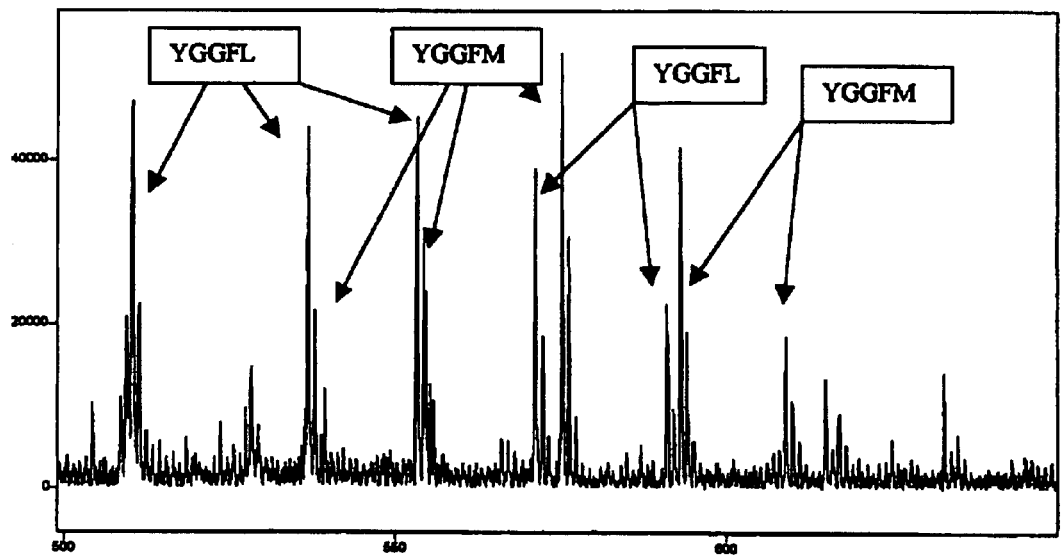
Figure 5:
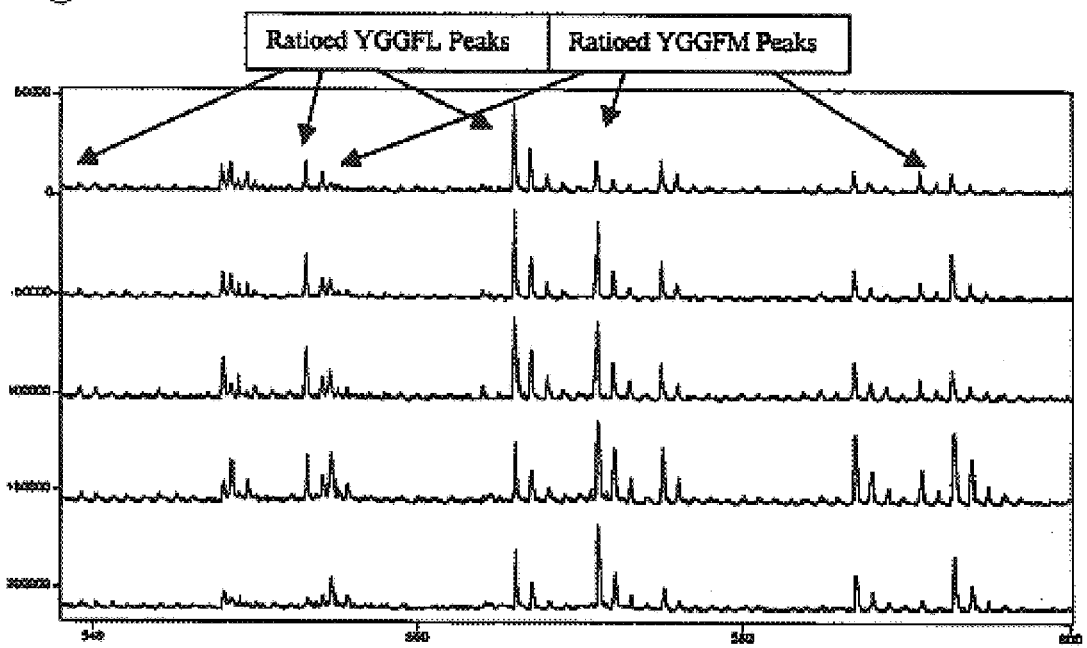

Samples were analyzed by MALDI to construct calibration curves for YGGFM utilizing YGGFL as the internal standard. The MALDI mass spectra for YGGFL is displayed in FIG. 2. The $(M+H)^+$ molecular ion can be seen at 555.6D. The spectrum also contains sodium and acetate related adduct peaks at 577.6D and 597.6D. Peaks at 538.6 and 512.6 are oxygen, carbon and nitrogen losses from the peptide backbone. FIG. 3 is the MALDI mass spectrum for YGGFM. The $(M+H)^+$ molecular ion can is detected at 573.7D. The spectrum also contains sodium and acetate related adduct peaks at 595.7D and 615.7D. Peaks at 557.7 and 531.7 are oxygen, carbon and nitrogen losses from the peptide backbone. FIG. 4 is a MALDI mass spectrum of the two components in combination. This is performed to determine if the peaks associated with both peptides could be resolved. FIG. 5 is an example of stacked set of spectra showing YGGFM increasing in peak intensity (concentration) from top to bottom (573D) while showing YGGFL decreasing relatively (577).

Figure 6:
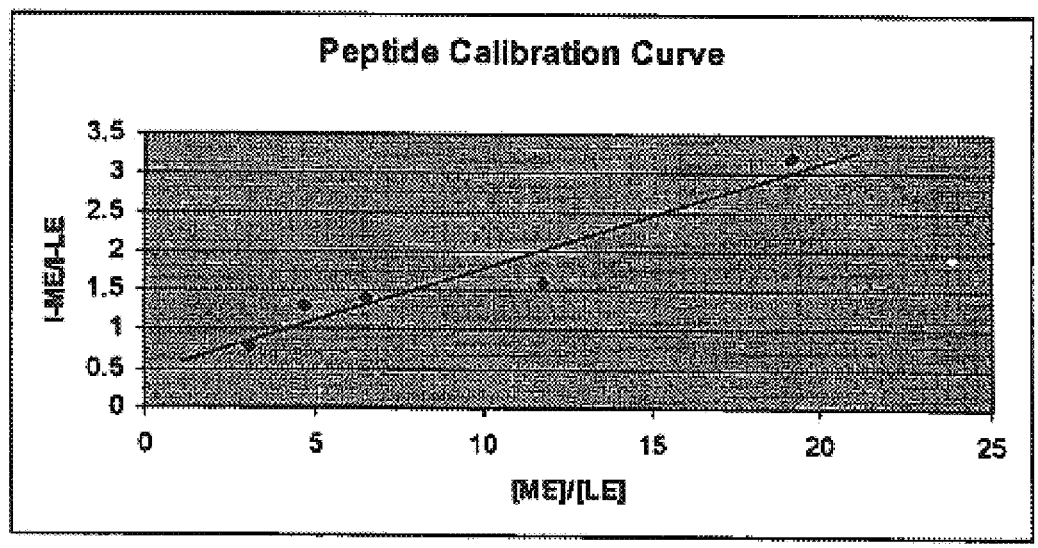
Figure 7:
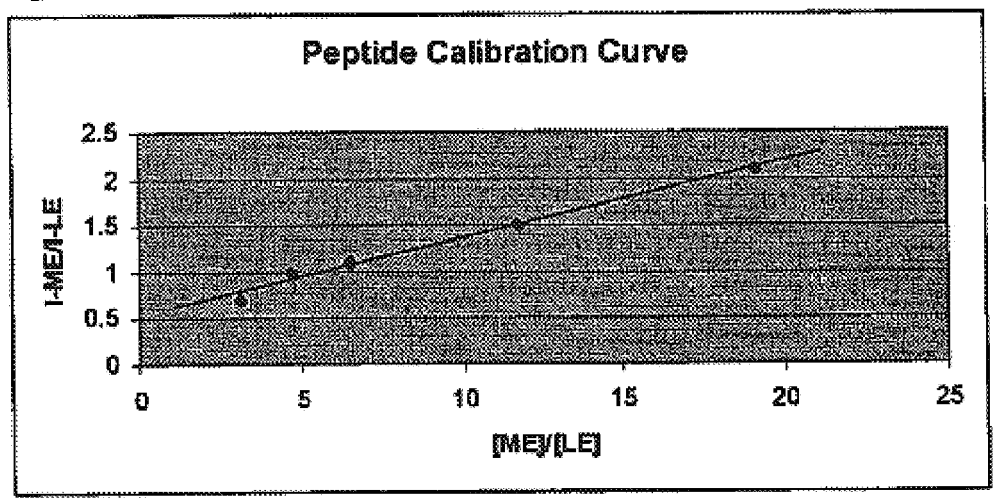

In this study we describe two different approaches for the construction of calibration curves from the intensity data in the mass spectrum in FIG. 5. A first approach was to ratio the intensity of the molecular ions $(M+H)^+$ of each molecule (YGGFM/YGGFL) and plot this ratio versus the same concentration ratio. This calibration curve is shown in FIG. 6. The equation of the line and the correlation coefficient are $Y=0.13X+0.45$ and $R^2=0.958$. A second calibration curve was constructed by summing the intensities of three peaks for each peptide, taking the ratio and plotting that ratio versus the same concentration ratios. The three peaks chosen for YGGFL and YGGFM were 539D, 555D, 577D and 557D, 573D, 595D, respectively which are assigned in the above paragraph. This calibration curve was displayed in FIG. 7. The equation of the line and correlation coefficient are $Y=0.082X+0.53$ and $R^2=0.993$. The concentration ratios and peak intensity ratios from both approaches are seen in Table 25. It can quickly be determined from the correlation coefficient that the line derived from the summation of multiple peaks yields a better fit.

TABLE 25

Final Concentrations and Peak Intensity Ratios for YGGFL and YGGFM

| Solution | I-YGGFM/ I-YGGFL | ΣI-YGGFM/ ΣI-YGGFL | [YGGFM]/[YGGFL] |
|---|---|---|---|
| Solution 25A | 0.8 | 0.7 | 3.11 |
| Solution 25B | 1.3 | 1.0 | 4.70 |
| Solution 25C | 1.4 | 1.1 | 6.53 |
| Solution 25D | 1.6 | 1.5 | 11.74 |
| Solution 25E | 3.2 | 2.1 | 19.1 |

L Calibration Curves Utilizing CC as the Internal Standard

In order to extend the quantitative method to proteins a similar approach was tested to construct calibration curves for L utilizing CC as the IS.

Figure 8:
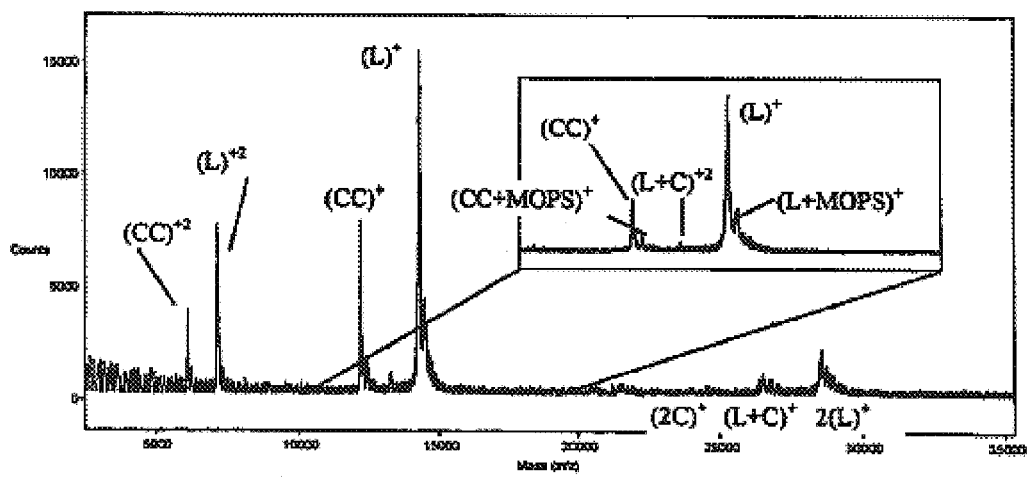

The MALDI mass spectrum of a mixture of L and CC was shown in FIG. 8. The MALDI analyses yielded many peaks in the mass spectrum. The L related ions were $(L)^{+2}$ at 7.1KD, $(L+MOPS\ buffer)^{+2}$ at 7.2KD, $(L)^{+1}$ at 14.3KD, $(L+MOPS\ buffer)^{+1}$ at 14.5KD, $(L+CC)^{-2}$ at 13.3KD, $(L+CC)^{+1}$ at 26.5KD and finally $(2L)^{+1}$ at 28.6KD. The CC related ions were $(CC)^{+2}$ at 6.1KD, $(CC+MOPS\ buffer)^{+2}$ at 6.2KD, $(CC)^{+1}$ at 12.2KD, $(CC+MOPS\ buffer)^{+1}$ at 12.4KD, $(L+CC)^{+2}$ at 13.3KD, $(L+CC)^{+1}$ at 26.5KD and finally $(2CC)^{+1}$ at 24.4KD. The molecular ion region was expanded in FIG. 8 to better illustrate the molecular ion peaks.

Figure 9:
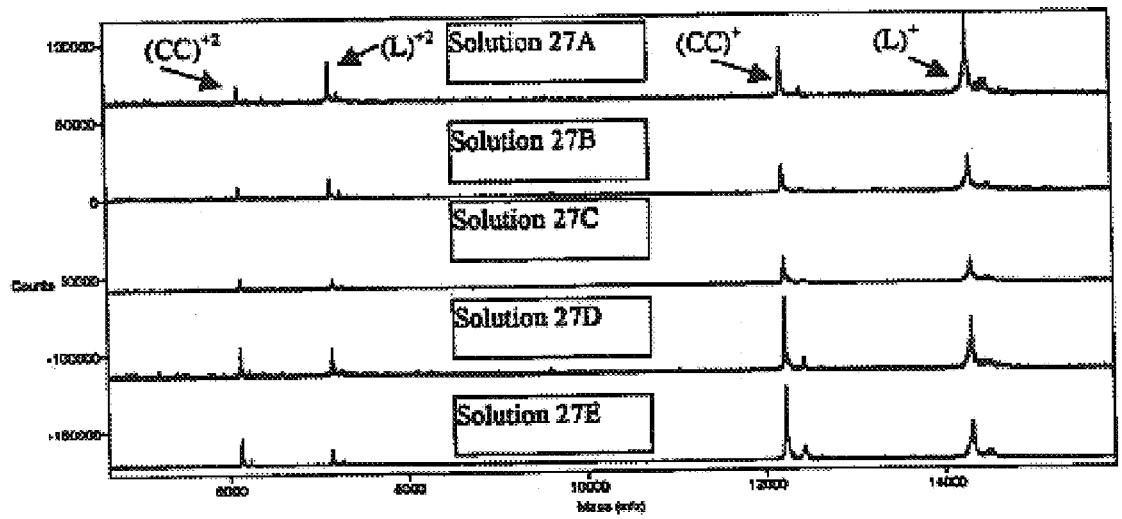

Two calibration curves were constructed from the mass spectrum from four concentrations (refer to Table 5). FIG. 9 is an example of stacked spectrum showing L decreasing in concentration (and peak intensity) from top to bottom while showing CC increasing relatively. The first calibration curve was the intensity ratios of the molecular ions (L/CC) versus the concentration ratios. This calibration curve was shown in FIG. 10. The equation of the line and the correlation coefficient are $Y=0.15X+0.11$ and $R^2=0.991$ (ANOVA 95%–F=107.1). The second calibration curve was the sum of all the related L peak intensities divided by the sum of all of the CC peak intensities (ratios) versus the same concentration ratios. This calibration curve was displayed in FIG. 11. The equation of the line and correlation coefficient are $Y=0.19X+0.10$ and $R^2=0.9997$ (ANOVA 95%–F=3814.0). Each data point on the calibration curve was an average of results from 4 to 5 spectra. The concentration ratios and peak intensity ratios from both approaches can be seen in Table 26. This corresponds with sample preparations from Tables 3, 4 and 5. Signal from samples 5D and 5E were below detection limits so another sample was prepared for analysis. That sample has been labeled Sample 26D. It can quickly be determined from the correlation coefficient that the summing approach yields a better fit.

TABLE 26

Final Concentrations and Peak Intensity Ratios for L and CC

| Solution | I-L/I-CC | ΣI-L/ΣI-CC | [L]/[CC] |
|---|---|---|---|
| Solution 26A | 0.37 | 0.46 | 2.0 |
| Solution 26B | 0.74 | 0.90 | 4.1 |
| Solution 26C | 1.83 | 2.02 | 10.2 |
| Solution 26D | 2.09 | 2.66 | 13.6 |

Two more calibration curves were constructed from the mass spectra from five concentrations to reproduce the above results (refer to Table 8). The first calibration curve was constructed from the intensity ratios of the molecular ions (L/CC) versus the concentration ratios. This calibration curve was shown in FIG. 12. The equation of the line and the correlation coefficient are $Y=0.18X+0.11$ and $R^2=0.998$ (ANOVA 95%–F=793.2). The second calibration curve was the sum of all the related L peak intensities divided by the sum of all of the CC peak intensities (ratio) versus the same concentration ratios. This calibration curve is displayed in FIG. 13. The equation of the line and correlation coefficient are $Y=0.19X+0.12$ and $R^2=0.9992$ (ANOVA 95%–F=1762.6). Each data point was an average of results from 4 to 5 mass spectra. The concentration ratios and peak intensity ratios, both approaches, can be seen in Table 27. This section corresponds to those sample preparations for data Table 6, 7 and 8. It can quickly be determined from the correlation coefficient that the summing approach yields a better fit.

TABLE 27

Final Concentrations and Peak Intensity Ratios for L and CC

| Solution | I-L/I-CC | ΣI-L/ΣI-CC | [L]/[CC] |
|---|---|---|---|
| Solution 27A | 1.65 | 1.79 | 8.5 |
| Solution 27B | 1.22 | 1.34 | 6.4 |
| Solution 27C | 0.88 | 0.94 | 4.2 |
| Solution 27D | 0.72 | 0.77 | 3.2 |
| Solution 27E | 0.47 | 0.52 | 2.2 |

HSA Calibration Curves Utilizing CC as the IS

Figure 14:
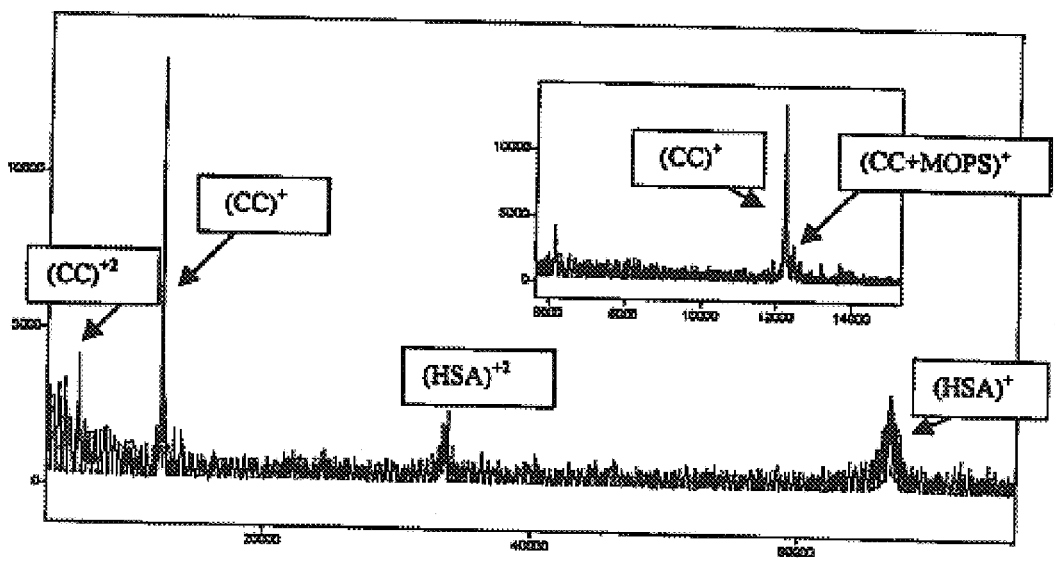

Samples were analyzed by MALDI to construct calibration curves for HSA utilizing CC as the IS (refer to Table 11). The MALDI mass spectrum of a mixture of HSA and CC is shown in FIG. 14. The MALDI analyses yielded many peaks in the mass spectrum. The HSA related ions were $(HSA)^{+2}$ at 33.2KD, $(HSA)^{+1}$ at 66.4KD, $(2HSA)^{+1}$ at 132.8KD (not shown) and finally $(3HSA)^{+1}$ at 199.2KD (not shown). The CC related ions were $(CC)^{+2}$ at 6.1KD, $(CC+MOPS\ buffer)^{+2}$ at 6.2KD, $(CC)^{+1}$ at 12.2KD and $(CC+MOPS\ buffer)^{+1}$ at 12.4KD. The molecular ion region was expanded in FIG. 14 to better illustrate the CC molecular ion peaks.

Figure 15:
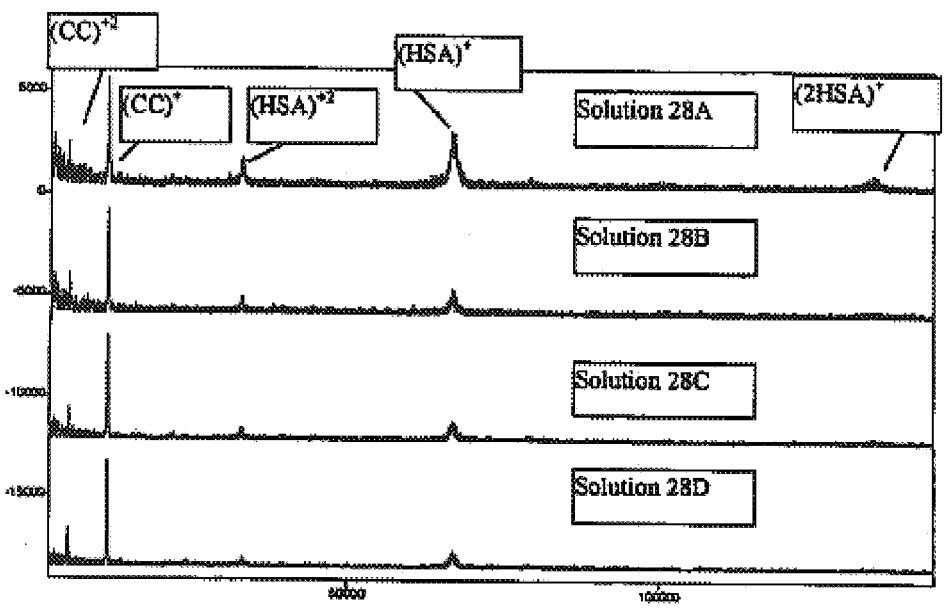

Two calibration curves were constructed from the intensities resulting from mass spectra of four concentration ratios. FIG. 15 is an example of stacked spectrum showing HSA decreasing in concentration (and peak intensity) from top to bottom while showing CC increasing relatively. The first approach to the calibration curve was based on plotting the intensity ratios of the molecular ions (HSA/CC) versus the concentration ratios. This calibration curve was shown in FIG. 16. The equation of the line and the correlation coefficient are Y=0.028X+0.010 and $R^2$=0.993 (ANOVA 95%–F=135.6). The second approach for the calibration curve was plotting the sum of all the related HSA peak intensities divided by the sum of all of the CC peak intensities (ratios) versus the same concentration ratios. This calibration curve is displayed in FIG. 17. The equation of the line and correlation coefficient are Y=0.034X+0.055 and $R^2$=0.9991 (ANOVA 95%–F=1049.2). Each data point on the calibration curve was an average of 4 to 5 spectra. The concentration ratios and peak intensity ratios from both approaches can be seen in Table 28. It can quickly be determined from the correlation coefficient that the summing approach yields a better fit.

TABLE 28

Final Concentrations and Peak Intensity Ratios for HSA and CC

| Solution | I-HSA/I-CC | ΣI-HSA/ΣI-CC | [HSA]/[CC] |
| --- | --- | --- | --- |
| Solution 28A | 0.49 | 0.62 | 16.6 |
| Solution 28B | 0.39 | 0.52 | 13.3 |
| Solution 28C | 0.27 | 0.40 | 9.95 |
| Solution 28D | 0.21 | 0.28 | 6.63 |

Figure 18:
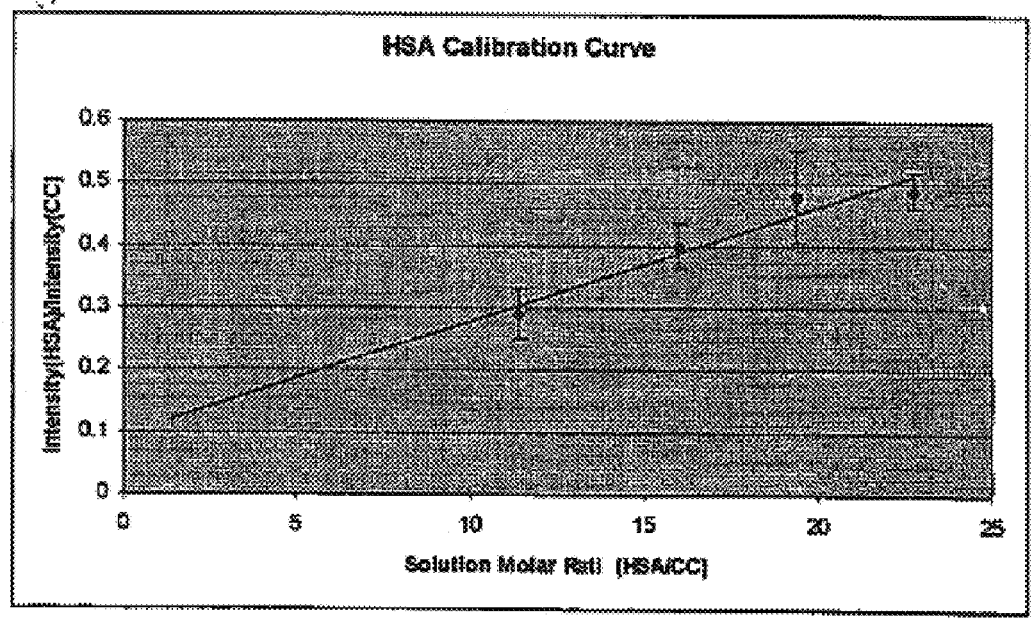

Two more calibration curves were constructed from the mass spectra from five concentrations to reproduce the above results (refer to Table 14). The first calibration curve was based on ratioing the intensities the molecular ions (HSA/CC) and plotting them versus the concentration ratios. This calibration curve is shown in FIG. 18. The equation of the line and the correlation coefficient are Y=0.018X+0.095 and $R^2$=0.966 (ANOVA 95%–F=27.9). The second calibration curve was constructed from the sum of all the related HSA peak intensities divided by the sum of all of the CC peak intensities (ratio) versus the concentration ratios. This calibration curve is displayed in FIG. 19. The equation if the line and correlation coefficient are Y=0.035X+0.044 and $R^2$=0.992 (ANOVA 95%–F=122.9). Each data point is an average of 4 to 5 mass spectra. The concentration ratios and peak intensity ratios, both approaches, can be seen in Table 29. It can quickly be determined from the correlation coefficient that the summing approach yields a better fit.

TABLE 29

Final Concentrations and Peak Intensity Ratios for HSA and CC

| Solution | I-HSA/I-CC | ΣI-HSA/ΣI-CC | [HSA]/[CC] |
| --- | --- | --- | --- |
| Solution 29A | 0.49 | 0.85 | 22.9 |
| Solution 29B | 0.48 | 0.75 | 19.5 |
| Solution 29C | 0.40 | 0.58 | 16.1 |
| Solution 29D | 0.29 | 0.46 | 11.5 |

La Calibration Curves Utilizing CC as the IS

Figure 20:
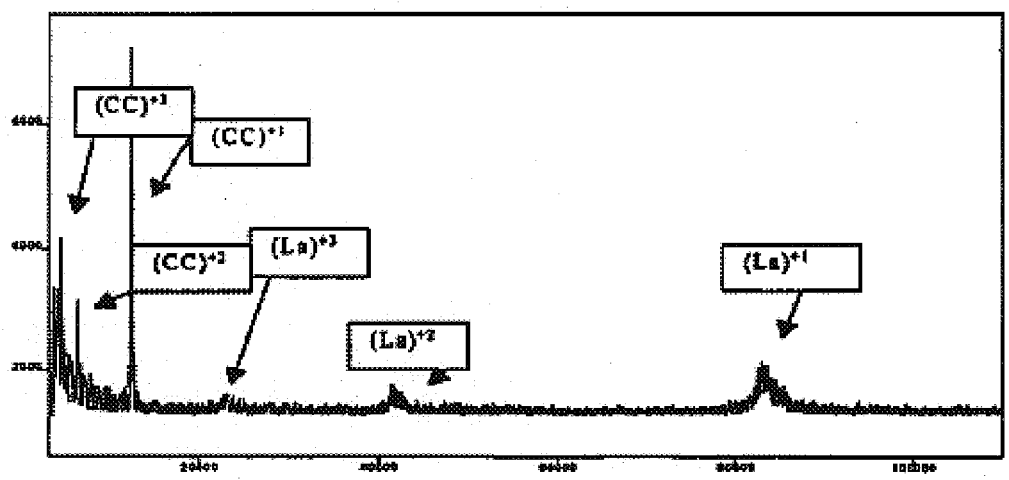

Samples were analyzed by MALDI to construct calibration curves for La utilizing CC as the IS. The MALDI mass spectrum of a mixture of La and CC is shown in FIG. 20. The MALDI analyses yielded many peaks in the mass spectra. The La related ions were $(La)^{+3}$ at 26.3KD, $(La)^{+2}$ at 39.0KD and $(La)^{+1}$ at 78.0KD. At high concentration $(2La)^{+1}$ at 156.0KD was sometimes detected. The CC related ions were $(CC)^{+3}$ at 4.1KD, $(CC)^{+2}$ at 6.1KD, $(CC+MOPS\ buffer)^{+2}$ at 6.2KD, $(CC)^{+1}$ at 12.2KD, $(CC+MOPS\ buffer)^{+1}$ at 12.4KD and finally $(2\ CC)^{+1}$ at 24.4KD.

Figure 21:
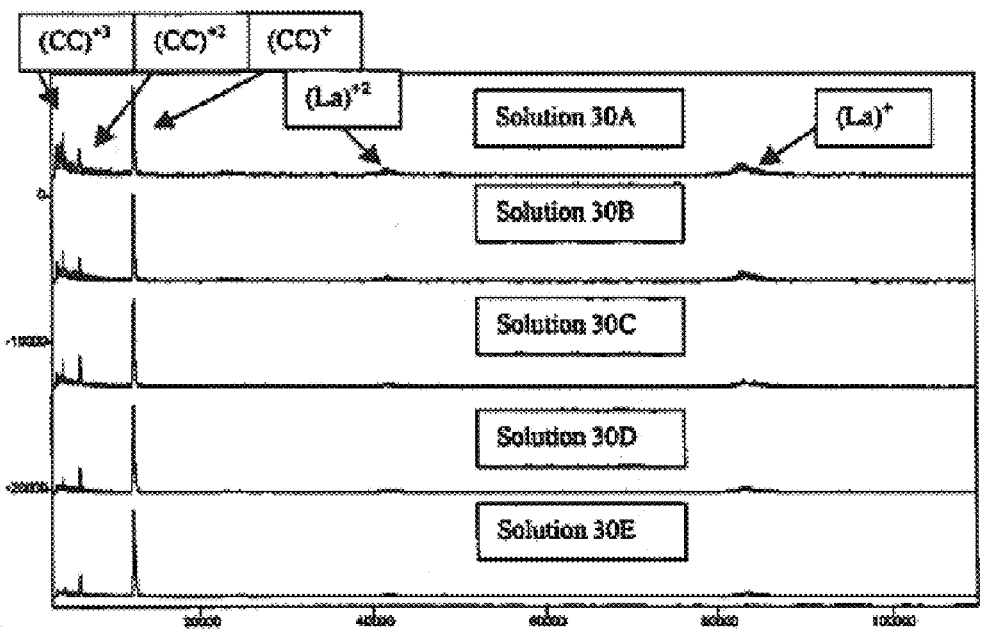
Figure 22:
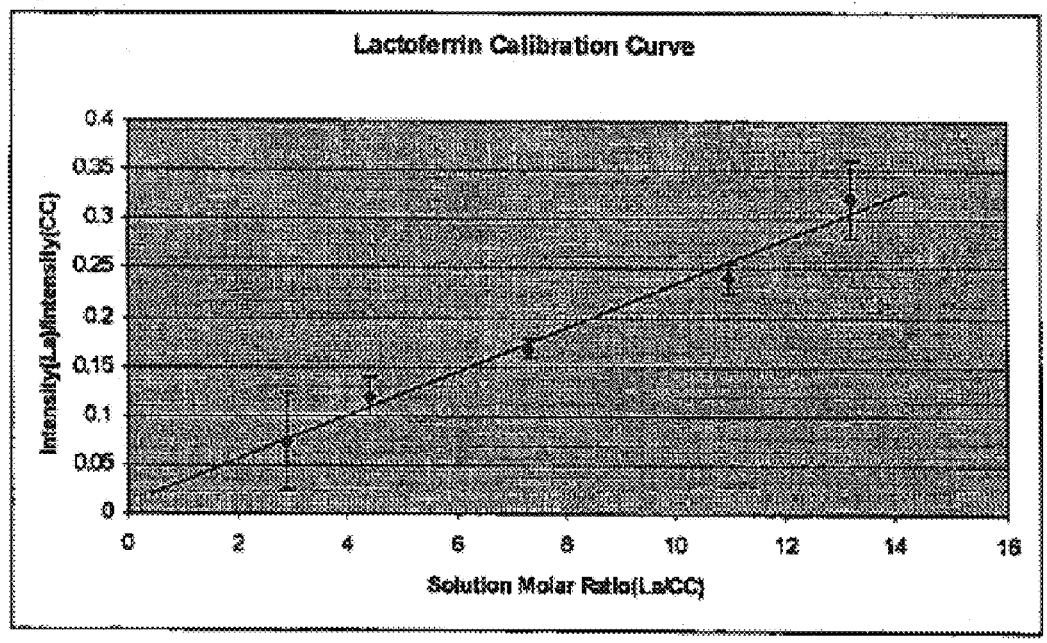

Two calibration curves were constructed from the intensity results from the mass spectra from five concentration ratios (refer to Table 17). FIG. 21 is an example of stacked spectrum showing La decreasing in concentration (and peak intensity) from top to bottom while showing CC increasing relatively. The first approach to calibration curve construction was based on plotting the intensity ratios of the molecular ions (La/CC) versus the concentration ratios. This calibration curve is shown in FIG. 22. The equation of the line and the correlation coefficient are Y=0.022X+0.012 and $R^2$=0.992 (ANOVA 95%–F=183.2). The approach for the second calibration curve was to plot the sum of all the related La peak intensities divided by the sum of all of the CC peak intensities (ratios) versus the concentration ratios. This calibration curve is displayed in FIG. 23. The equation of the line and correlation coefficient are Y=0.027X+0.016 and $R^2$=0.9992 (ANOVA 95%–F=1829.8). Each data point on the calibration curve is an average of results from 4 to 5 spectra. The concentration ratios and peak intensity ratios from both approaches can be seen in Table 30. It can quickly be determined from the correlation coefficient that the summing approach yields a better fit.

TABLE 30

Final Concentrations and Peak Intensity Ratios for La and CC

| Solution | I-La/I-CC | ΣI-La/ΣI-CC | [La]/[CC] |
| --- | --- | --- | --- |
| Solution 30A | 0.32 | 0.38 | 13.2 |
| Solution 30B | 0.24 | 0.31 | 11.0 |
| Solution 30C | 0.17 | 0.21 | 7.3 |
| Solution 30D | 0.12 | 0.14 | 4.4 |
| Solution 30E | 0.074 | 0.095 | 2.9 |

Figure 24:
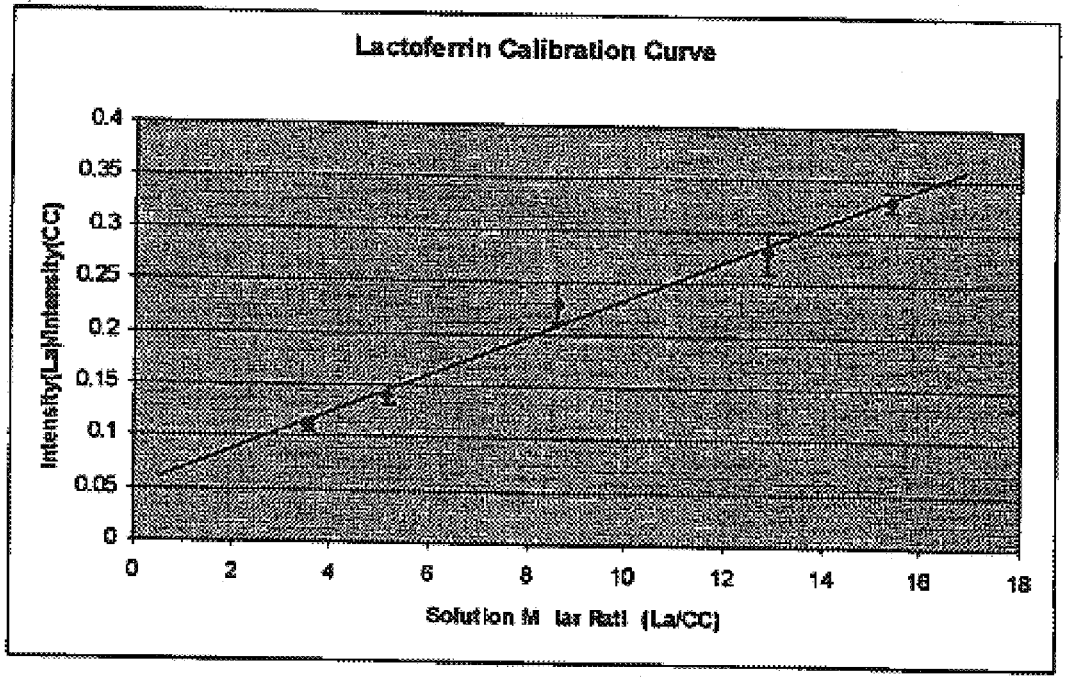

Two more calibration curves were constructed from the mass spectra from five concentrations to reproduce the above results (refer to Table 20). The first calibration curve was based on ratioing the intensities of the molecular ions (La/CC) versus the concentration ratios. This calibration curve is shown in FIG. 24. The equation of the line and the correlation coefficient are Y=0.018X+0.051 and $R^2$=0.992 (ANOVA 95%–F=174.2). The second calibration curve was constructed from the sum of all the related La peak intensities divided by the sum of all of the CC peak intensities (ratio) versus the concentration ratios. This calibration curve is displayed in FIG. 25. The equation of the line and correlation coefficient are Y=0.024X+0.017 and $R^2$=0.993 (ANOVA 95%–F=207.2). Each data point was an average of results from 4 to 5 mass spectra. The concentration ratios and peak intensity ratios from both approaches can be seen in Table 31. It can quickly be determined from the correlation coefficient that the summing approach yields a better fit.

TABLE 31

Final Concentrations and Peak Intensity Ratios for La and CC

| Solution | I-La/I-CC | ΣI-La/ΣI-CC | [La]/[CC] |
| --- | --- | --- | --- |
| Solution 31A | 0.33 | 0.37 | 15.6 |
| Solution 31B | 0.28 | 0.35 | 13.0 |
| Solution 31C | 0.23 | 0.22 | 8.8 |
| Solution 31D | 0.14 | 0.14 | 5.2 |
| Solution 31E | 0.11 | 0.10 | 3.5 |

UV Calibration Curves

The next few sections will discuss the construction of three UV calibration curves. The sample preparations for each calibration curve were described and outlined in the experimental under UV Calibration Curves.

Figure 26:
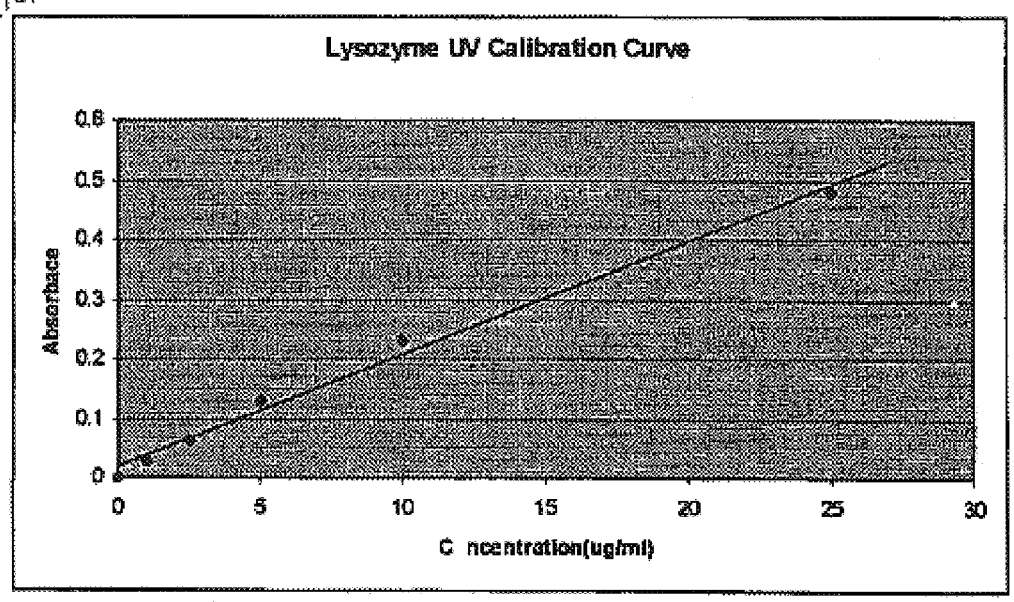

The UV calibration curves for L were constructed by graphing absorbance versus concentration, Table 32. The experiment was run in duplicate and the results were identical. The calibration curve is shown in FIG. 26. The equation of the line is Y=0.019X+0.018 with a correlation coefficient of 0.996.

TABLE 32

Final L Absorbences and Concentrations for the UV Calibration Curve

| Solution | [L]ug/ml | Absorbence |
|---|---|---|
| Solution 32A | 0.0 | 0.0 |
| Solution 32B | 2.5 | 0.029 |
| Solution 32C | 1.0 | 0.069 |
| Solution 32D | 5.0 | 0.129 |
| Solution 32E | 10.0 | 0.232 |
| Solution 32F | 25.0 | 0.479 |

Figure 27:
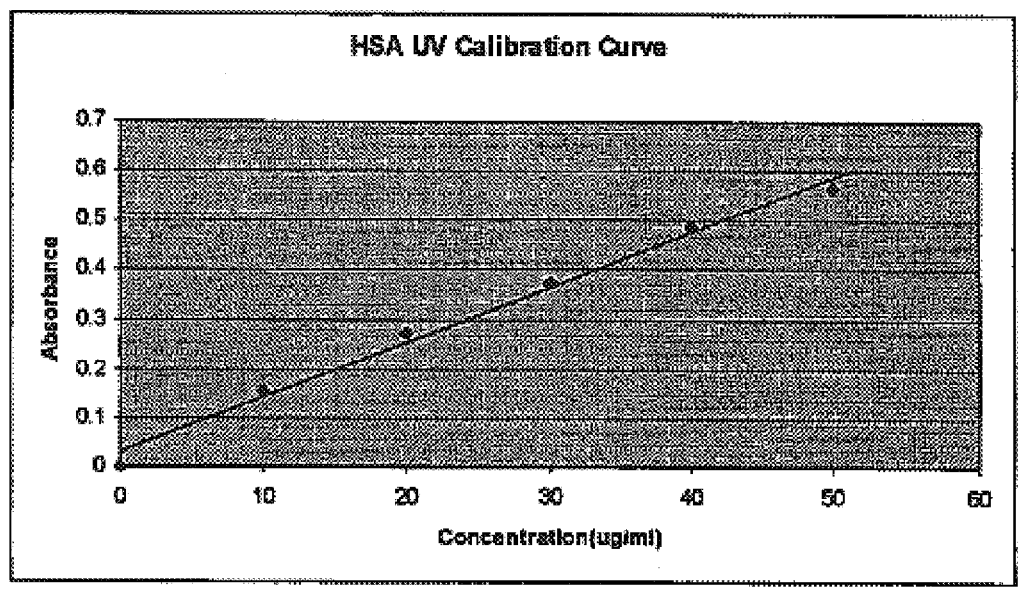

The UV calibration curves for HSA were constructed by graphing absorbence versus concentration, Table 33. The experiment was run in duplicate and the results again were identical. The calibration curve is shown in FIG. 27. The equation of the line is Y=0.0112X+0.029 with a correlation coefficient of 0.995.

TABLE 33

Final HSA Absorbences and Concentrations for the UV Calibration Curve

| Solution | [HSA]ug/ml | Absorbence |
|---|---|---|
| Solution 33A | 0.0 | 0.0 |
| Solution 33B | 10.0 | 0.156 |
| Solution 33C | 20.0 | 0.275 |
| Solution 33D | 30.0 | 0.374 |
| Solution 33E | 40.0 | 0.488 |
| Solution 33F | 50.0 | 0.564 |

Figure 28:
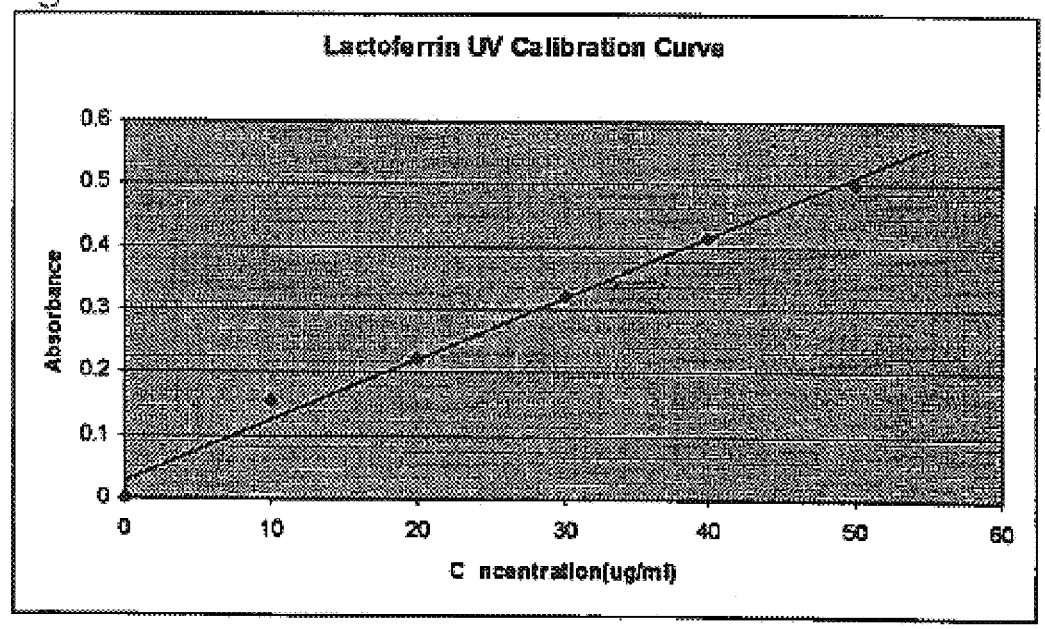

The UV calibration curves for La were constructed by graphing absorbence versus concentration, Table 34. The experiment was run in duplicate and the results again were identical. The calibration curve is shown in FIG. 28. The equation of the line is Y=0.0097X+0.027 and has a correlation coefficient of 0.995.

TABLE 34

Final La Absorbences and Concentrations for the UV Calibration Curve

| Solution | [La]ug/ml | Absorbence |
|---|---|---|
| Solution 34A | 0.0 | 0.0 |
| Solution 34B | 10.0 | 0.155 |
| Solution 34C | 20.0 | 0.223 |
| Solution 34D | 30.0 | 0.321 |
| Solution 34E | 40.0 | 0.414 |
| Solution 34F | 50.0 | 0.502 |

MALDI and UV Results for the Application of the Calibration Curves

MALDI and UV Results for L Uptake by a Contact Lens Material

Samples were analyzed by MALDI to determine L absorption and adsorption into and onto ACCUVUE™, a contact lens material, utilizing CC as the internal standard. The ion formation for L and CC was discussed in the section for MALDI Calibration Curves.

Figure 12:
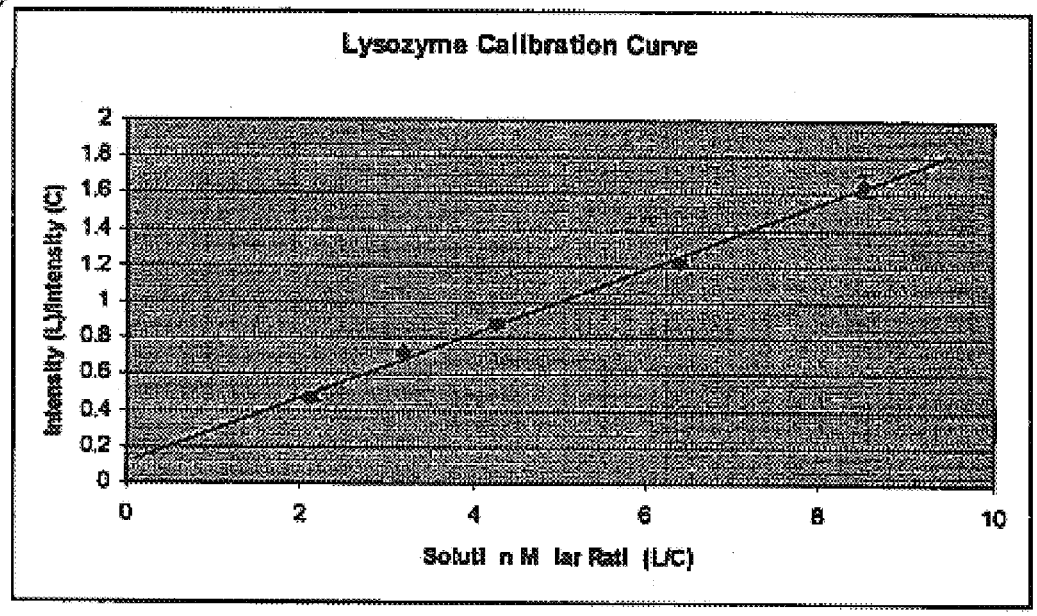
Figure 13:
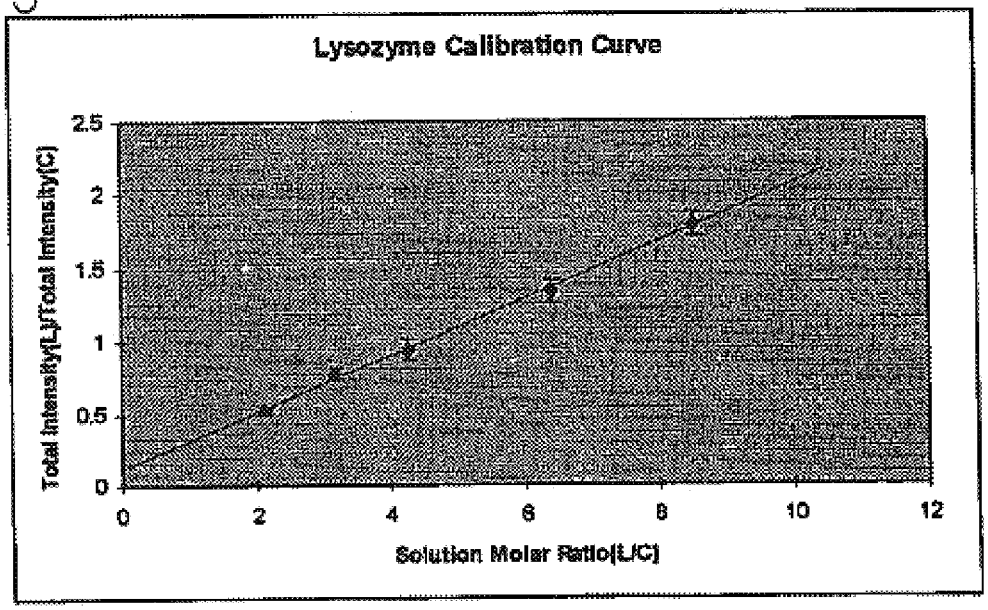
Figure 29:
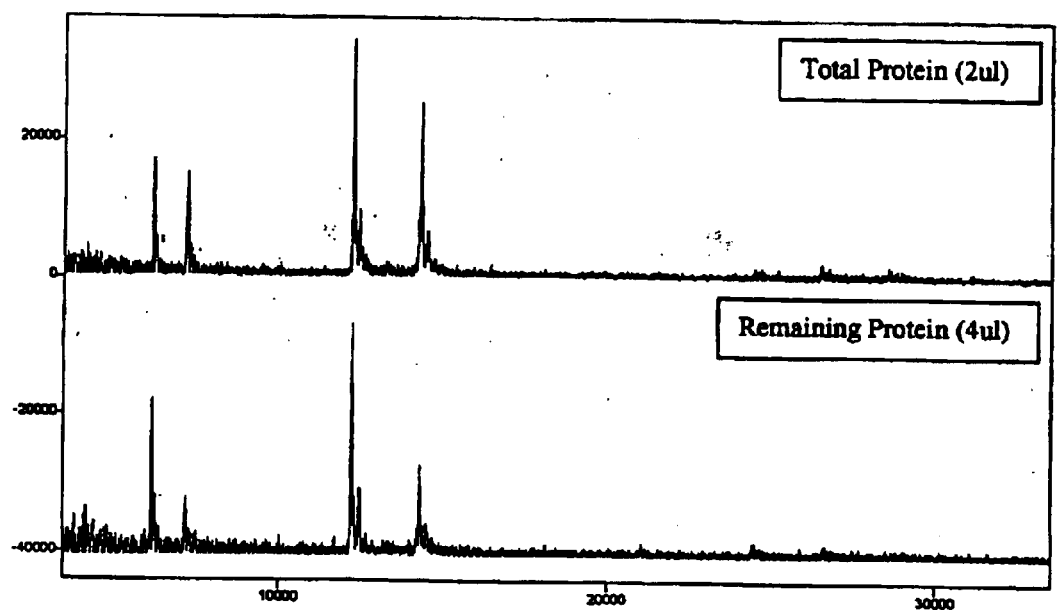

Samples solutions labeled Total Protein and Remaining Protein were analyzed for L content by MALDI. The MALDI, as reported above. Six L solutions labeled Total Protein contained no contact lens material. The concentrations of these solutions were 0.6 mg/ml. Each vial contained 1.5 ml of the solution for a theoretical amount of 900 ug of L. Aliquots of these solutions were taken, mixed with matrix, CC and analyzed by MALDI-ToF MS. From the obtained MALDI mass spectrum the parent peak intensity ratio, L divided by CC, was determined to be 0.69+/−0.14. This data was applied to both L calibration curves, FIGS. 10 and 12. The L content in this sample set determined by MALDI was either 1,001 ug+/−200 (FIG. 10) or 834 ug+/−167 (FIG. 12). From the same obtained MALDI mass spectra the sum of the peak intensity ratios, L divided by CC, was determined to be 0.72+/−0.13. This data was applied to both L calibration curves, FIGS. 11 and 13. The L content in this sample set determined by MALDI, utilizing the summing approach, was either 844 ug+/−152 (FIG. 3.11) or 820 ug+/−148 (FIG. 13). Both approaches yielded data statistically the same as the theoretical L content, 900 ug. The solutions labeled Remaining Protein were the same solutions labeled total Protein, 0.6 mg/ml, but this solution had a contact lens placed in it. Aliquots of these solutions were taken, mixed with matrix, CC and analyzed by MALDI. From the obtained MALDI mass spectrum the parent peak intensity ratio, L divided by CC, was determined to be 0.37+/−0.03. This data was applied to both L calibration curves, FIGS. 10 and 12. The L content in this sample set determined by MALDI was either 223 ug+/−22 (FIG. 10) or 204 ug+/−21 (FIG. 12). From the same obtained MALDI mass spectrum the sum of the peak intensity ratios, L divided by CC, was determined to be 0.42+/−0.04. This data was applied to both L calibration curves, FIGS. 11 and 13. The L content in this sample set determined by MALDI was either 218 ug+/−22 (FIG. 11) or 204 ug+/−20 (FIG. 13). Each data point was an average of five or six mass spectra. MALDI stack spectrum of the Total Protein and the Remaining protein can be seen in FIG. 29. The peaks in the spectrum were identified in FIG. 8. The above data is tabulated in Tables 35 and 36.

The L uptake by the ACCUVUE contact lens was determined by subtracting the Total Protein results from the Remaining Protein results. These results were also included in Tables 35 and 36.

TABLE 35

L Uptake of an ACCUVUE Contact Lens Material Utilizing Parent Peak Ratios from MALDI Mass Spectra

Figure 10:
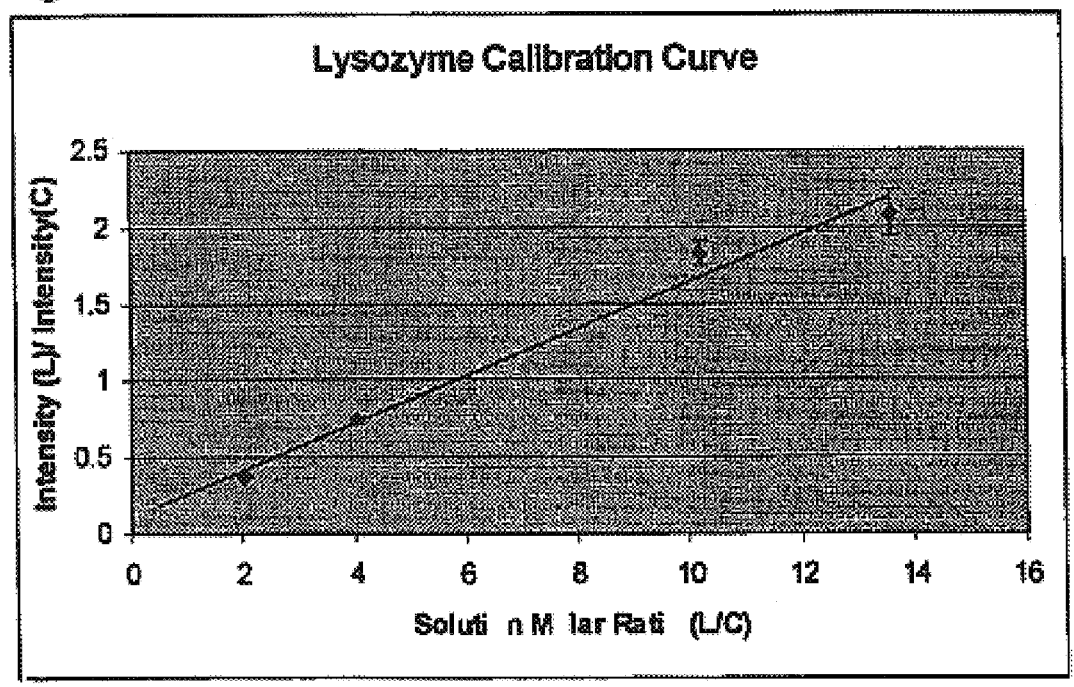

| Calibration Curve | Total Protein(ug) | Remaining Protein(ug) | L Uptake(ug) |
|---|---|---|---|
| FIG. 10 | 1001 +/− 200 | 223 +/− 22 | 778 +/− 201 |
| FIG. 12 | 843 +/− 167 | 204 +/− 21 | 630 +/− 168 |

TABLE 36

L Uptake of an ACCUVUE Contact Lens Material Utilizing Summing Peak Ratios from MALDI Mass Spectra

Figure 11:
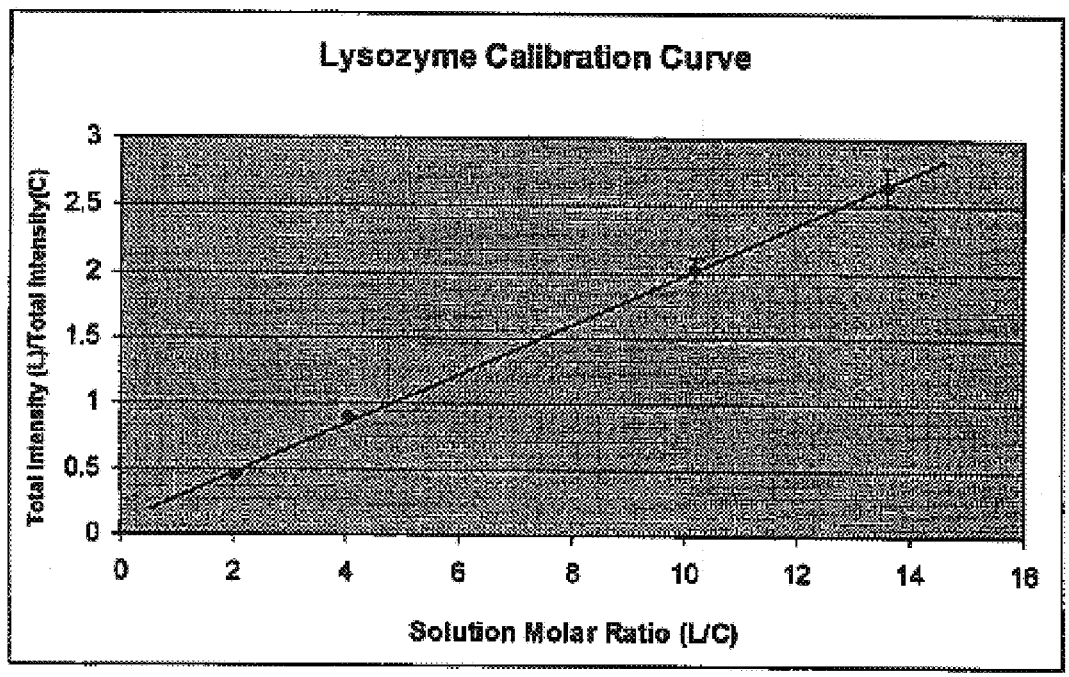

| Calibration Curve | Total Protein(ug) | Remaining protein(ug) | L Uptake(ug) |
|---|---|---|---|
| FIG. 11 | 844 +/− 152 | 218 +/−+22 | 626 +/− 153 |
| FIG. 13 | 820 +/− 148 | 204 +/− 20 | 616 +/− 149 |

Samples solutions labeled Total Protein and Remaining Protein were analyzed for L content by an UV calorimetric assay. These were the same solutions analyzed above by MALDI. The UV sample preparations for this sample set and the UV calibration curve were discussed above. Aliquots of these solutions were mixed with BCA stock solution, incubated, cooled and the absorbence measured. The absorbencies of the samples labeled Total Protein were 0.171+/−0.007. This corresponds to 972 ug+/−40 of L. Aliquots of solutions labeled Remaining Protein were mixed with BCA stock solution, incubated, cooled and the absorbance measured. The absorbencies of the samples labeled Remaining Protein were 0.061+/−0.002. This corresponds to 277 ug+/−10 of L. Each data point was an average of six UV measurements. The UV absorbence data was tabulated in Tables 37. The L uptake by the ACCUVUE contact lens was determined by subtracting the Total Protein results from the Remaining Protein results. These results are included in Tables 38.

TABLE 37

L UV Absorbence Data

| Sample | Total Protein Absorbence | Remaining protein Absorbence |
|---|---|---|
| Sample 1 | 0.164 | 0.061 |
| Sample 2 | 0.171 | 0.059 |
| Sample 3 | 0.168 | 0.061 |
| Sample 4 | 0.172 | 0.059 |
| Sample 5 | 0.174 | 0.065 |
| Sample 6 | 0.184 | 0.061 |
| Mean +/− SD | 0.171 +/− 0.007 | 0.061 +/− 0.002 |

TABLE 38

L Uptake by UV Method

| Total Protein | Remaining Protein | L Uptake |
|---|---|---|
| 972 +/− 40 | 277 +/− 10 | 695 +/− 41 |

The L uptake measured by UV was in good agreement (1σ) with the MALDI results utilizing either the parent peak ratio method or the summing peak ratio method.

The L experiment above was duplicated. The protein content in the Total Protein and Remaining Protein solutions were tabulated in Tables 39 and 40 utilizing both sets of calibration curves and both ratio methods. The L uptake by the ACCUVUE contact lens was determined by subtracting the Total Protein results from the Remaining Protein results. These results are also included in Tables 39 and 40.

TABLE 39

L Uptake of an ACCUVUE Contact Lens Material
Utilizing Parent Peak Ratios from MALDI Mass Spectra

| Calibration Curve | Total Protein(ug) | Remaining Protein(ug) | L Uptake(ug) |
|---|---|---|---|
| FIG. 10 | 1080 +/− 116 | 250 +/− 27.8 | 830 +/− 119 |
| FIG. 12 | 900 +/− 96.3 | 208 +/− 23.1 | 692 +/− 99.0 |

TABLE 40

L Uptake of an ACCUVUE Contact Lens Material
Utilizing Summing Peak Ratios from MALDI Mass Spectra

| Calibration Curve | Total Protein(ug) | Remaining Protein(ug) | L Uptake(ug) |
|---|---|---|---|
| FIG. 11 | 979 +/− 81.5 | 261 +/− 30.3 | 718 +/− 87.0 |
| FIG. 13 | 947 +/− 75.8 | 245 +/− 28.4 | 702 +/− 80.9 |

The same sample solutions above labeled Total Protein and Remaining Protein were analyzed for L content by an UV calorimetric assay. The UV sample preparations for this sample set and the calibration curve results are reported above. The UV absorbence data is tabulated in Table 41. The L content was determined by applying the absorbence results to the calibration curve. The L uptake by the ACCUVUE contact lens was determined by subtracting the Total Protein results from the Remaining Protein results. These results were included in Tables 42.

TABLE 41

L UV Absorbence Data

| Sample | Total Protein Absorbence | Remaining Protein Absorbence |
|---|---|---|
| Sample 1 | 0.181 | 0.073 |
| Sample 2 | 0.187 | 0.069 |
| Sample 3 | 0.181 | 0.069 |
| Sample 4 | 0.177 | 0.074 |
| Sample 5 | 0.181 | 0.079 |
| Sample 6 | 0.182 | — |
| Mean +/− SD | 0.182+/−0.003 | 0.073+/−0.004 |

TABLE 42

L Uptake by UV Method

| Total Protein | Remaining protein | L Uptake |
|---|---|---|
| 1073+/−18 | 352+/−19 | 721+/−26 |

The L uptake measured by UV was in good agreement (1σ) with the MALDI results utilizing either the parent peak ratio method or the summing peak ratio method.

MALDI and UV Results for HSA Uptake by a Contact Lens Material

Figure 30:
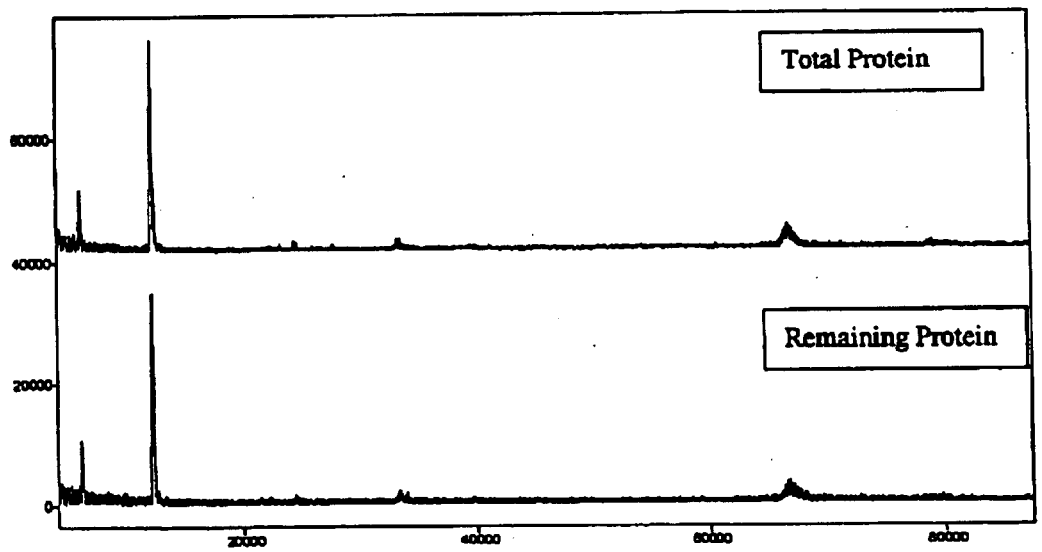

Samples were analyzed by MALDI to determine HSA absorption and adsorption into and onto ACCUVUE, a contact lens material, utilizing CC as the Internal Standard (IS). The MALDI sample preparations for this sample set and the HSA calibration curve results are discussed above. MALDI stack spectra of the Total Protein and the Remaining Protein can be seen in FIG. 30. The peaks in the spectrum are identified in FIG. 14. The protein content in the Total Protein and Remaining Protein solutions were tabulated in Tables 43 and 44 utilizing both sets of calibration curves and both ratio methods. The HSA uptake by the ACCUVUE contact lens was determined by subtracting the Total Protein results from the Remaining Protein results. These results are also included in Tables 43 and 44.

TABLE 43

HSA Uptake of an ACCUVUE Contact Lens Material
Utilizing Parent Peak Ratios from MALDI Mass Spectrum

Figure 16:
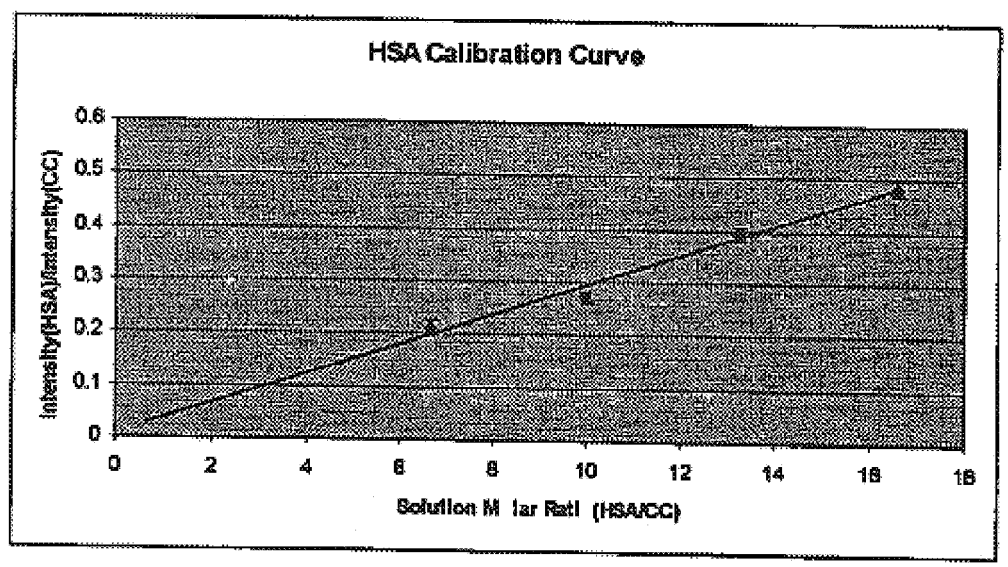

| Calibration Curve | Total Protein(ug) | Remaining Protein(ug) | HSA Uptake(ug) |
|---|---|---|---|
| FIG. 16 | 4054+/−341 | 4137+/−114 | −83+/−359 |
| FIG. 18 | 780+/−66 | 910+/−25 | −130+/−71 |

TABLE 44

HSA Uptake of an ACCUVUE Contact Lens Material
Utilizing Summing Peak Ratios from MALDI Mass Spectra

Figure 17:
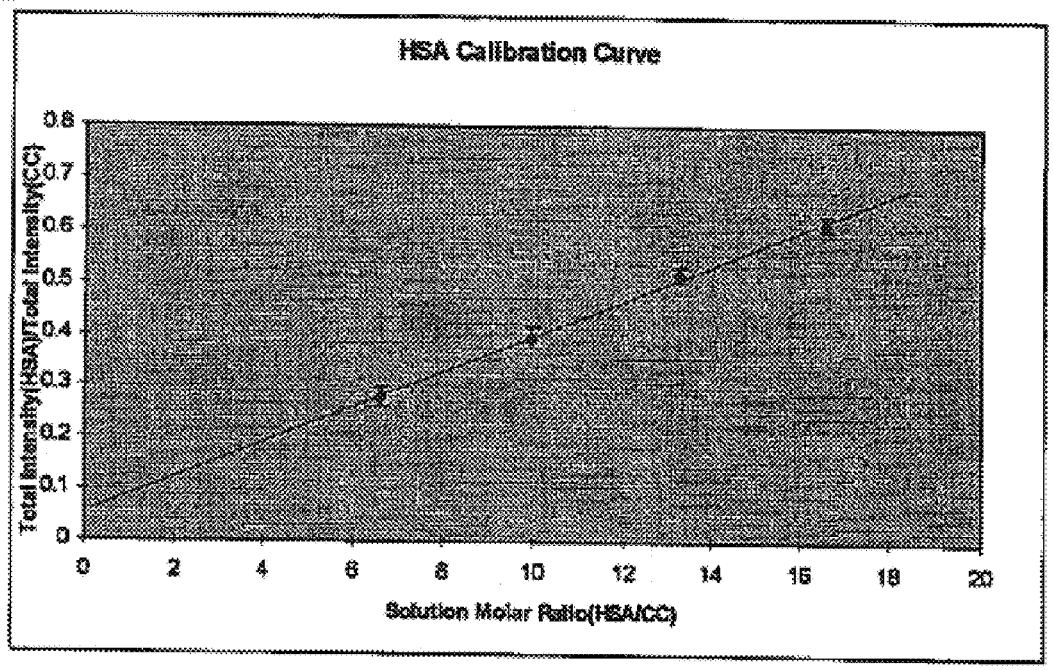
Figure 19:
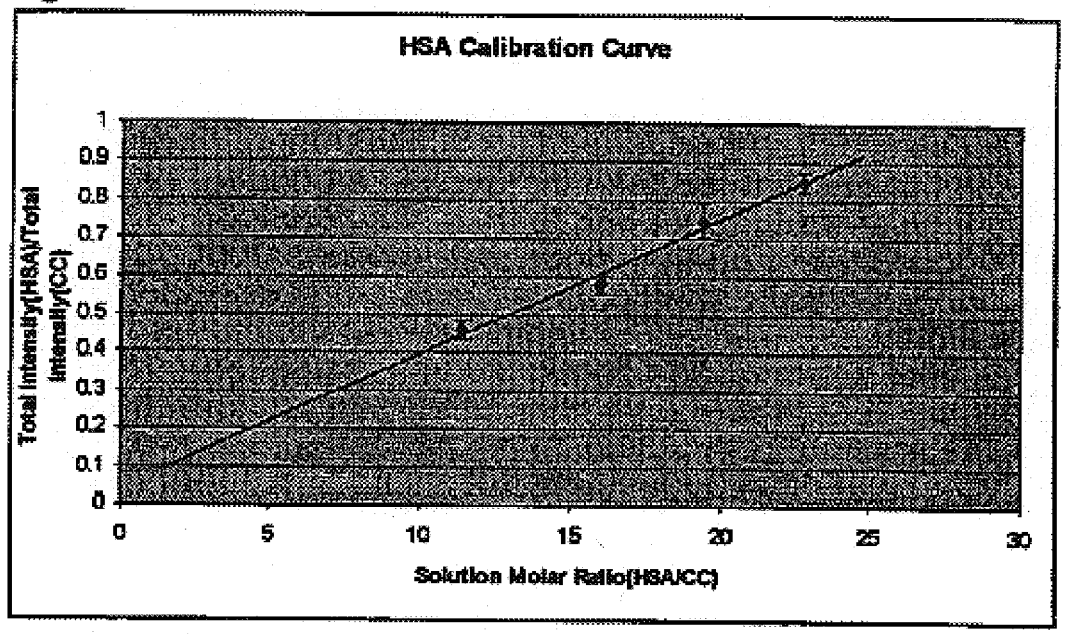

| Calibration Curve | Total Protein(ug) | Remaining Protein(ug) | HSA Uptake(ug) |
|---|---|---|---|
| FIG. 17 | 2306+/−96 | 2375+/−77 | −69+/−123 |
| FIG. 19 | 2608+/−148 | 2675+/−86 | −67+/−171 |

Samples solutions labeled Total Protein and Remaining Protein were analyzed for HSA content by an UV colorimetric assay. The UV sample preparations for this sample set and the calibration curve results are discussed above. The UV absorbence data is tabulated in Tables 45. The HSA content was determined by applying the absorbence results to the calibration curve. The HSA uptake by the ACCUVUE contact lens was determined by subtracting the Total Protein results from the Remaining Protein results. These results were included in Tables 46.

TABLE 45

HSA UV Absorbence Data

| Sample | Total Protein Absorbence | Remaining Protein Absorbence |
|---|---|---|
| Sample 1 | 0.293 | 0.298 |
| Sample 2 | 0.295 | 0.299 |
| Sample 3 | 0.298 | 0.290 |
| Sample 4 | 0.294 | 0.298 |
| Sample 5 | 0.298 | 0.303 |
| Sample 6 | 0.300 | 0.304 |
| Mean +/− SD | 0.296+/−0.003 | 0.299+/−0.005 |

TABLE 46

HSA Uptake by UV Method

| Total protein | Remaining Protein | Albumin Uptake |
|---|---|---|
| 2862+/−29 | 2886+/−48 | −24+/−56 |

The HSA uptake measured by UV was in good agreement (1σ) with the MALDI results utilizing either the parent peak ratio method or the summing peak ratio method.

The HSA experiment above was duplicated. Samples solutions labeled Total Protein and Remaining Protein were analyzed for HSA content by MALDI. The MALDI sample preparations for this sample set and the HSA calibration curve results are discussed above. The protein content in the Total Protein and Remaining Protein solutions are tabulated in Tables 47 and 48 utilizing both sets of calibration curves and both ratio methods. The HSA uptake by the ACCUVUE contact lens was determined by subtracting the Total Protein results from the Remaining Protein results. These results are also included in Tables 47 and 48.

TABLE 47

HSA Uptake of an ACCUVUE Contact Lens Material
Utilizing Parent Peak Ratios from MALDI Mass Spectrum

| Calibration Curve | Total Protein(ug) | Remaining Protein(ug) | HSA Uptake(ug) |
|---|---|---|---|
| FIG. 16 | 4795+/−333 | 4867+/−300 | −72.0+/−448 |
| FIG. 18 | 2727+/−189 | 2839+/−175 | −112+/−257 |

TABLE 48

HSA Uptake of an ACCUVUE Contact Lens Material
Utilizing Summing Peak Ratios from MALDI Mass Spectrum

| Calibration Curve | Total Protein(ug) | Remaining Protein(ug) | HSA Uptake(ug) |
|---|---|---|---|
| FIG. 17 | 2770+/−93 | 2829+/−94 | −59+/−132 |
| FIG. 19 | 3006+/−101 | 3063+/−101 | −57+/−143 |

Samples solutions labeled Total Protein and Remaining Protein were analyzed for HSA content by an UV calorimetric assay. The UV sample preparations for this sample set and the calibration curve results are discussed above. The UV absorbence data was tabulated in Tables 48. The HSA content was determined by applying the absorbence results to the calibration curve. The HSA uptake by the ACCUVUE contact lens was determined by subtracting the Total Protein results from the Remaining Protein results. These results were included in Tables 49.

TABLE 48

HSA UV Absorbence Data

| Sample | Total Protein Absorbence | Remaining Protein Absorbence |
|---|---|---|
| Sample 1 | 0.361 | 0.361 |
| Sample 2 | 0.371 | 0.369 |
| Sample 3 | 0.376 | 0.366 |
| Sample 4 | 0.373 | 0.375 |
| Sample 5 | 0.362 | 0.383 |
| Sample 6 | 0.371 | 0.385 |
| Mean +/− SD | 0.369+/−0.006 | 0.373+/−0.010 |

TABLE 49

HSA Uptake by UV Method

| Total Protein | Remaining Protein | HSA Uptake |
|---|---|---|
| 3642+/−59 | 3685+/−99 | −43+/−115 |

The HSA uptake measured by UV was in good agreement (1σ) with the MALDI results utilizing either the parent peak ratio method or the summing peak ratio method.

MALDI and UV Results for La Uptake by a Contact Lens Material

Figure 31:
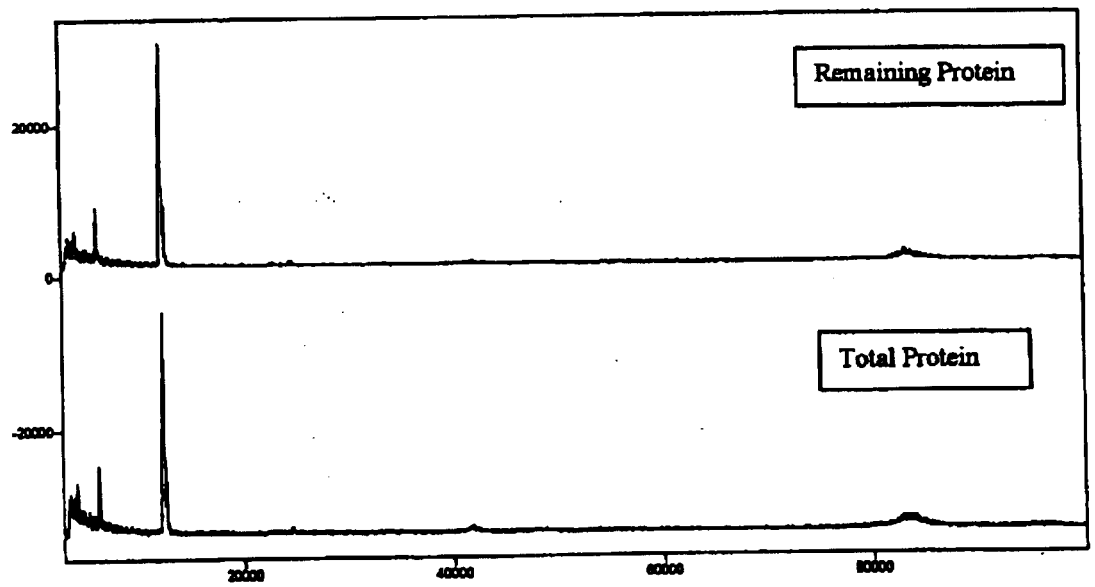

Samples were analyzed by MALDI to determine La absorption and adsorption into and onto ACCUVUE, a contact lens material, utilizing CC as the IS. The MALDI sample preparations for this sample set and the La calibration curve results are discussed above. MALDI stack spectra of the Total Protein and the Remaining Protein can be seen in FIG. 31. The peaks in the spectrum were identified in FIG. 20. The protein content in the Total Protein and Remaining Protein solutions were tabulated in Tables 50 and 51 utilizing both sets of calibration curves and both ratio methods. The La uptake by the ACCUVUE contact lens was determined by subtracting the Total Protein results from the Remaining Protein results. These results were also included in Tables 50 and 51.

TABLE 50

La Uptake of an ACCUVUE Contact Lens Material
Utilizing Parent Peak Ratios from MALDI Mass Spectra

| Calibration Curve | Total Protein(ug) | Remaining Protein(ug) | La Uptake(ug) |
|---|---|---|---|
| FIG. 22 | 3481+/−281 | 3081+/−276 | 400+/−393 |
| FIG. 24 | 2347+/−189 | 1858+/−167 | 489+/−252 |

TABLE 51

La Uptake of an ACCUVUE Contact Lens Material
Utilizing Summing Peak Ratios from MALDI Mass Spectra

Figure 23:
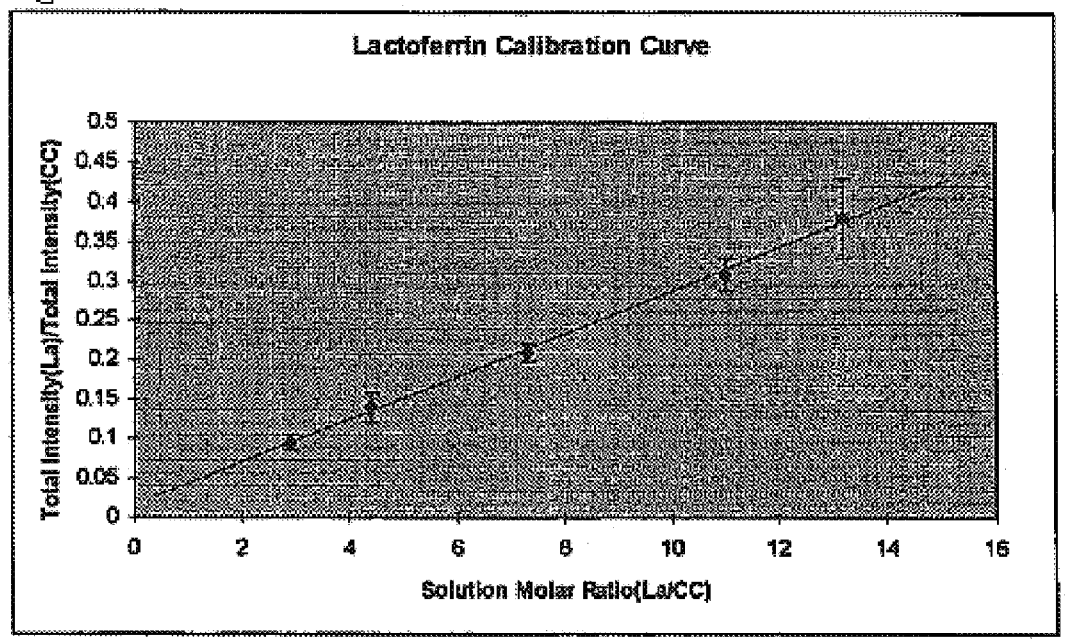
Figure 25:
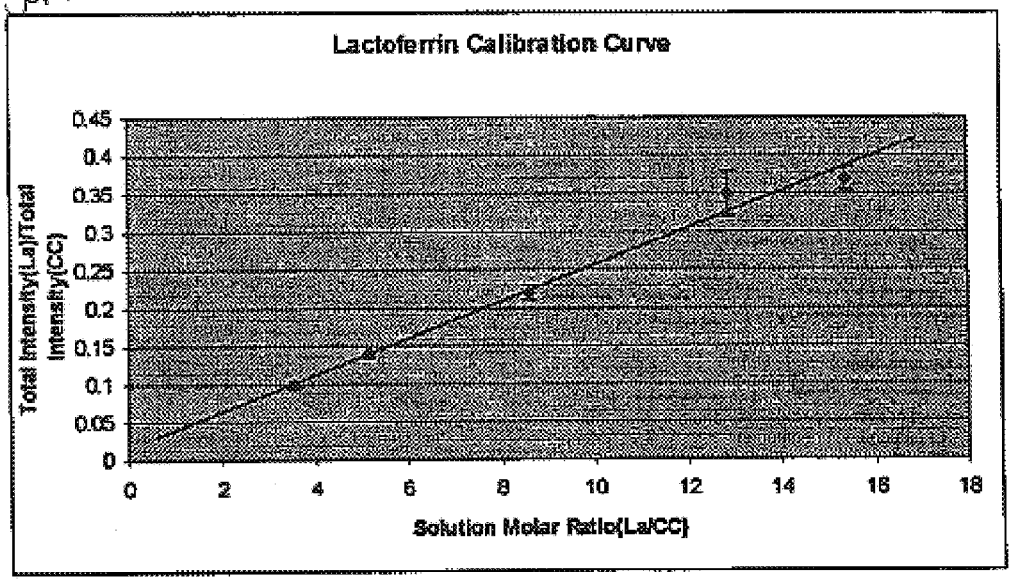

| Calibration Curve | Total Protein(ug) | Remaining Protein(ug) | La Uptake(ug) |
|---|---|---|---|
| FIG. 23 | 2282+/−159 | 2021+/−130 | 261+/−205 |
| FIG. 25 | 2531+/−177 | 2237+/−143 | 294+/−223 |

Samples solutions labeled Total Protein and Remaining Protein were analyzed for La content by an UV colorimetric assay. The UV sample preparations for this sample set and the calibration curve results are provided above. The UV absorbence data is tabulated in Tables 52. The La content was determined by applying the absorbence results to the calibration curve. The La uptake by the ACCUVUE contact lens was determined by subtracting the Total Protein results from the Remaining Protein results. These results were included in Tables 53.

TABLE 52

La UV Absorbence Data

| Sample | Total Protein Absorbence | Remaining Protein Absorbence |
|---|---|---|
| Sample 1 | 0.287 | 0.250 |
| Sample 2 | 0.293 | 0.254 |
| Sample 3 | 0.288 | 0.250 |
| Sample 4 | 0.287 | 0.272 |
| Sample 5 | 0.283 | 0.249 |
| Sample 6 | 0.277 | 0.243 |
| Mean +/− SD | 0.286+/−0.005 | 0.253+/−0.010 |

TABLE 53

La Uptake by UV Method

| Total Protein | Remaining | La Uptake |
|---|---|---|
| 3238+/−57 | 2825+/−112 | 413+/−126 |

The La uptake measured by UV was in good agreement (1σ) with the MALDI results utilizing either the parent peak ratio method or the summing peak ratio method.

The La experiment above was duplicated. Samples solutions labeled Total Protein and Remaining Protein were analyzed for La content by MALDI. The MALDI sample preparations for this sample set and the La calibration curve results are discussed above. The protein content for the Total Protein and Remaining Protein solutions are tabulated in Tables 54 and 55 utilizing both sets of calibration curves and both ratio methods. The La uptake by the ACCUVUE contact lens was determined by subtracting the Total Protein results from the Remaining Protein results. These results are also included in Tables 54 and 55.

TABLE 54

La Uptake of an ACCUVUE Contact Lens Material
Utilizing Parent Peak Ratios from MALDI Mass Spectra

| Calibration Curve | Total Protein(ug) | Remaining Protein(ug) | La Uptake(ug) |
|---|---|---|---|
| FIG. 22 | 3728+/−229 | 3285+/−113 | 443+/−255 |
| FIG. 24 | 3050+/−188 | 2510+/−87 | 540+/−207 |

TABLE 55

La Uptake of an ACCUVUE Contact Lens Material
Utilizing Summing Peak Ratios from MALDI Mass Spectra

| Calibration Curve | Total Protein(ug) | Remaining Protein(ug) | La Uptake(ug) |
|---|---|---|---|
| FIG. 23 | 2497+/−110 | 2188+/−87 | 309+/−140 |
| FIG. 25 | 2780+/−123 | 2432+/−96 | 348+/−156 |

Samples solutions labeled Total Protein and Remaining Protein were analyzed for La content by an UV colorimetric assay. The UV sample preparations for this sample set and the calibration curve results are provided above. The UV absorbence data is tabulated in Tables 56. The La content was determined by applying the absorbence results to the La calibration curve. The La uptake by the ACCUVUE contact lens was determined by subtracting the Total Protein results from the Remaining Protein results. These results were included in Tables 57.

TABLE 56

La UV Absorbence Data

| Sample | Total Protein Absorbence | Remaining Protein Absorbence |
|---|---|---|
| Sample 1 | 0.287 | 0.264 |
| Sample 2 | 0.302 | 0.257 |
| Sample 3 | 0.304 | 0.259 |
| Sample 4 | 0.316 | 0.274 |
| Sample 5 | 0.306 | 0.267 |
| Sample 6 | 0.299 | 0.250 |
| Mean +/− SD | 0.302+/−0.009 | 0.261+/−0.008 |

TABLE 57

La Uptake by UV Method

| Total Protein | Remaining Protein | La Uptake |
|---|---|---|
| 3437+/−102 | 2925+/−90 | 512+/−136 |

The La uptake measured by UV was in good agreement (1σ to 2σ) with the MALDI results utilizing either the parent peak ratio method or the summing peak ratio method.

MALDI and UV Results for a L and HSA Mixtures and Their Uptake by a Contact Lens Material Samples were analyzed by MALDI to determine a L and HSA Mixture absorption and adsorption into and onto ACCUVUE, a contact lens material, utilizing CC as the IS.

The ion formation for HSA, L and CC was discussed in earlier sections.

This section will be outlined as follows: Total L results against two L calibration curves using two ratio methods (parent peak and summing approach), Total HSA results against two HSA calibration curves using two ratio methods (parent peak and summing approach), Remaining L results against two L calibration curves using two ratio methods (parent peak and summing approach), Remaining HSA results against two HSA calibration curves utilizing two ratio methods (parent peak and summing approach) and finally the UV results. It should be noted that the UV can not discriminate between proteins but can only determine total protein (HSA+L). This experiment was then repeated.

Figure 32:
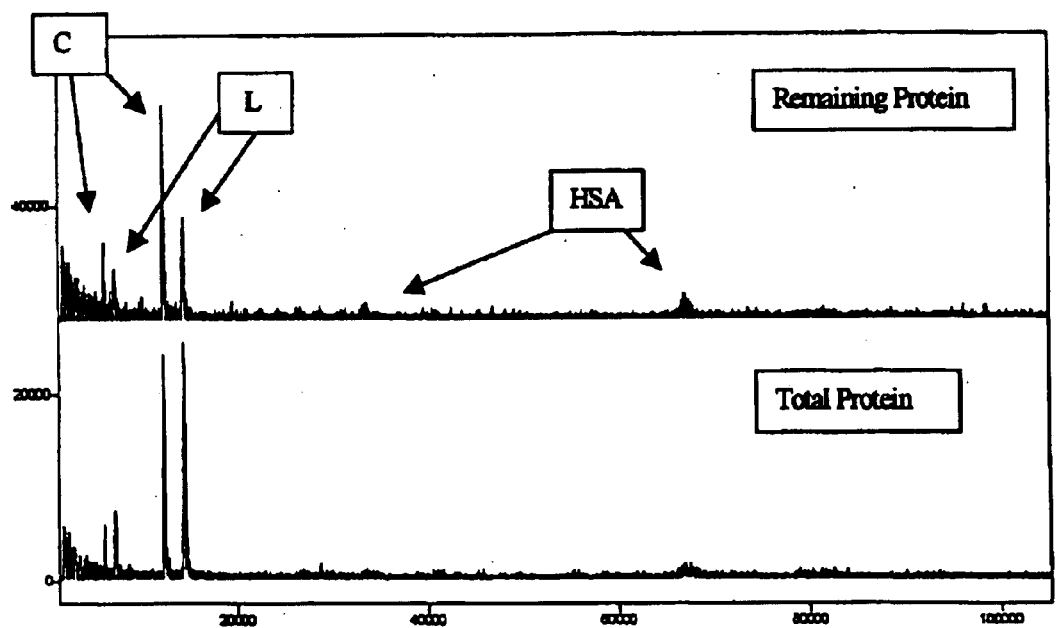
Figure 33:
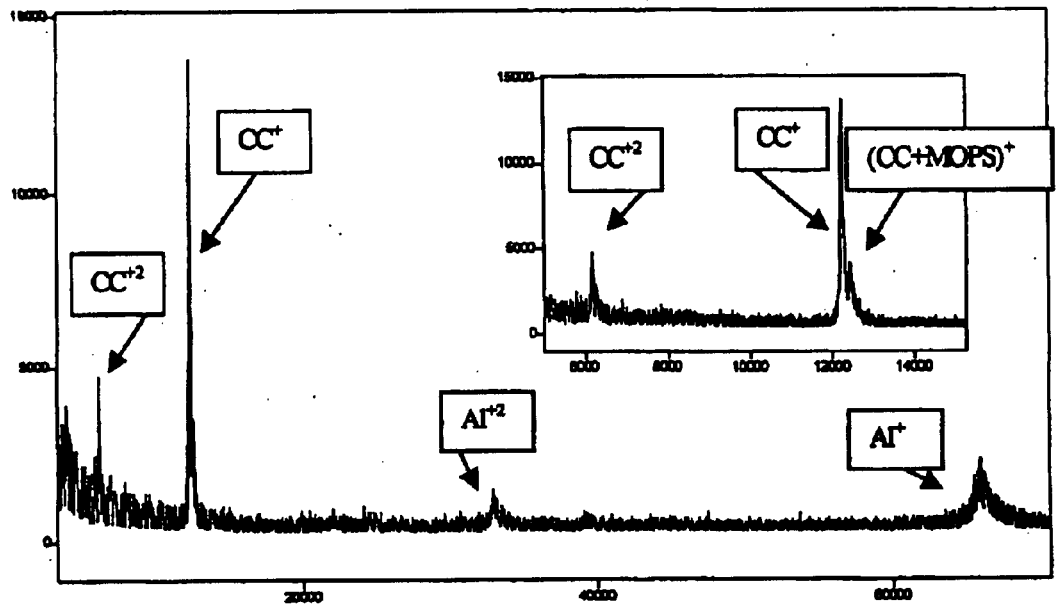

Samples solutions labeled Total Protein and Remaining Protein were analyzed for a mixture of L and HSA content by MALDI. The MALDI sample preparations for this sample set was discussed in above. Six solutions containing HSA and L were labeled Total Protein. This solution contained no contact lens material. The concentrations of these solutions were 2.6 mg/ml, 2.0 mg/ml HSA and 0.6 mg/ml L. Each vial contained 1.5 ml of the solution for a theoretical amount of 3900 ug for both proteins. Aliquots of these solutions were taken, mixed with matrix, CC and analyzed by MALDI. From the obtained MALDI mass spectrum the parent peak intensity ratio, L divided by CC, was determined to be 1.11+/−0.11. This data was applied to both L calibration curves, FIGURES 3.10 and 3.12. The L content in this sample set determined by MALDI was either 1566 ug+/−155 (FIG. 10) or 1306 ug+/−129 (FIG. 12). From the same obtained MALDI mass spectrum the sum of the peak intensity ratios, L divided by CC, was determined to be 1.12+/−0.09. This data was applied to both L calibration curves, FIGS. 11 and 13. The L content in this sample set determined by MALDI was either 1261 ug+/−101 (FIG. 11) or 1237 ug+/−99 (FIG. 13). Both approaches yielded data statistically higher than the theoretical L content, 900 ug. From the obtained MALDI mass spectrum the parent peak intensity ratio, HSA divided by CC, was determined to be 0.122+/−0.008. This data was applied to both HSA calibration curves, FIGS. 16 and 18. The HSA content in this sample set determined by MALDI was either 4365 ug+/−286 (FIG. 16) or 1637 ug+/−107 (FIG. 18). From the same obtained MALDI mass spectrum the sum of the peak intensity ratios, HSA divided by CC, was determined to be 0.142+/−0.008. This data was applied to both HSA calibration curves, FIGS. 17 and 19. The HSA content in this sample set determined by MALDI was either 2792 ug+/−157 (FIG. 17) or 3055 ug+/−172 (FIG. 19). The summing approach yielded data statistically the same to the theoretical HSA content, 3000 ug. The solutions labeled Remaining Protein were the same mixed L and HSA solutions, 2.6 mg/ml, but this solution had a contact lens placed in it. Aliquots of these solutions were taken, mixed with matrix, CC and analyzed by MALDI. From the obtained MALDI mass spectrum the parent peak intensity ratio, L divided by CC, was determined to be 0.48+/−0.02. This data was applied to both L calibration curves, FIGS. 10 and 12. The L content in this sample set determined by MALDI was either 580 ug+/−24 (FIG. 10) or 483 ug+/−20 (FIG. 12). From the same obtained MALDI mass spectrum the sum of the peak intensity ratios, L divided by CC, was determined to be 0.54+/−0.08. This data was applied to both L calibration curves, FIGS. 11 and 13. The L content in this sample set determined by MALDI was either 544 ug+/−81 (FIG. 11) or 519 ug+/−77 (FIG. 13). From the obtained MALDI mass spectrum the parent peak intensity ratio, HSA divided by CC, was determined to be 0.127+/−0.016. This data was applied to both HSA calibration curves, FIGS. 16 and 18. The HSA content in this sample set determined by MALDI was either 4560 ug+/−574 (FIG. 16) or 1940 ug+/−244 (FIG. 18). From the same obtained MALDI mass spectrum the sum of the peak intensity ratios, HSA divided by CC, was determined to be 0.145+/−0.013. This data was applied to both HSA calibration curves, FIGS. 17 and 19. The HSA content in this sample set determined by MALDI was either 2889 ug+/−259 (FIGURE 3.17) or 3149 ug+/−282 (FIG. 19). Each data point was an average of seven or six mass spectra. MALDI stack spectrum of the Total Protein and the Remaining protein can be seen in FIGS. 32 and 33. FIG. 32 is stacked spectrum of the mixture using L instrumental parameters and FIG. 33 is stacked spectrum of the mixture using HSA instrumental condition. The peaks in the spectrum were identified in FIG. 14. The above data was tabulated in Tables 58 and 59. The L and HSA uptake by the ACCUVUE contact lenses were determined by subtracting the Total Protein results from the Remaining Protein results. These results are also included in Tables 58 and 59.

TABLE 58

L and HSA Uptake of an ACCUVUE Contact Lens Material Utilizing Parent Peak Ratios from MALDI Mass Spectra

| Calibration Curve | Total Protein(ug) | Remaining Protein(ug) | Protein Uptake |
|---|---|---|---|
| FIG. 10(L) | 1566+/−155 | 580+/−24 | 986+/−157 |
| FIG. 12(L) | 1306+/−129 | 483+/−20 | 823+/−131 |
| FIG. 16 (HSA) | 4365+/−286 | 4560+/−574 | −195+/−641 |
| FIG. 18 (HSA) | 1637+/−107 | 1940+/−244 | −303+/−266 |

TABLE 59

L and HSA Uptake of an ACCUVUE Contact Lens Material Utilizing Summing Peak Ratios from MALDI Mass Spectra

| Calibration Curve | Total Protein(ug) | Remaining Protein(ug) | Protein Uptake |
|---|---|---|---|
| FIG. 10(L) | 1261+/−101 | 544+/−81 | 717+/−129 |
| FIG. 12(L) | 1237+/−99 | 519+/−77 | 718+/−125 |
| FIG. 16 (HSA) | 2792+/−157 | 2889+/−259 | −97+/−302 |
| FIG. 18 (HSA) | 3055+/−172 | 3149+/−282 | −94+/−330 |

Samples solutions labeled Total Protein and Remaining Protein were analyzed for L and HSA content by an UV colorimetric assay. The UV sample preparations for this sample set was discussed above. Six L and HSA solutions labeled Total Protein contained no contact lens material. The concentrations of these solutions were 2.6 mg/ml. Each vial contained 1.5 ml of the solution for a theoretical amount of 3900 ug of HSA and L. Aliquots of these solutions were mixed with BCA stock solution, incubated, cooled and the absorbence measured. The absorbencies of the samples labeled Total Protein were 0.412+/−0.007. This corresponds to 3111 ug+/−53 of utilizing the L UV calibration curve. This corresponds to 5116 ug+/−87 of utilizing the HSA UV calibration curve. Solutions labeled Remaining Protein were the same mixture L and HSA solutions, 2.6 mg/ml, but this solution had a contact lens placed in it. Aliquots of these solutions were mixed with BCA stock solution, incubated, cooled and the absorbence measured. The absorbencies of the samples labeled Remaining Protein were 0.345+/−0.006. This corresponds to 2582 ug+/−45 of utilizing the L UV calibration curve. The absorbence corresponds to 4219 ug+/−73 of utilizing the HSA UV calibration curve. Each data point was an average of six UV measurements. The raw data is tabulated in Tables 60. The HSA and L uptake by the ACCUVUE contact lenses were determined by subtracting the Total Protein results from the Remaining Protein results. These results are given in Table 61.

TABLE 60

HSA and L Mixture UV Raw Data

| Sample | Total Protein Absorbence | Remaining Protein Abdorbence |
|---|---|---|
| Sample 1 | 0.402 | 0.336 |
| Sample 2 | 0.406 | 0.347 |
| Sample 3 | 0.411 | 0.341 |
| Sample 4 | 0.416 | 0.344 |
| Sample 5 | 0.422 | 0.347 |
| Sample 6 | 0.412 | 0.355 |
| Mean+/−SD | 0.412+/−0.007 | 0.345+/−0.006 |

TABLE 61

Protein Uptake by UV Method

| Calibration Curve | Total Protein | Remaining Protein | Protein Uptake |
|---|---|---|---|
| L | 3111+/−53 | 2582+/−45 | 529+/−70 |
| HSA | 5116+/−87 | 4219+/−73 | 897+/−114 |

This UV method can not discriminate between proteins so the overall protein content was either 529 ug, L calibration curve, or 897 ug with the HSA calibration curve. Since the solution was a mixture of the two proteins, the actual result falls between 897–529 ug. The MALDI method can discriminate between proteins and those results, Tables 58 and 59, fall within the UV range for protein uptake.

The above experiment was repeated. Samples solutions labeled Total Protein and Remaining Protein were analyzed for L and HSA content by MALDI. The MALDI sample preparations for this sample set and the calibration curve results are discussed for L and HSA above. The ratios were applied to the appropriate calibration curves and the protein content was tabulated in Tables 62 and 63. The L and HSA uptake by the ACCUVUE contact lenses were determined by subtracting the Total Protein results from the Remaining Protein results. These results are also included in Tables 62 and 63.

TABLE 62

L and HSA Uptake of an ACCUVUE Contact Lens Material Utilizing Parent Peak Ratios from MALDI Mass Spectra

| Calibration Curve | Total Protein(ug) | Remaining Protein(ug) | Protein Uptake |
|---|---|---|---|
| FIG. 10 (L) | 1767+/−178 | 638+/−51 | 1129+/−185 |
| FIG. 12 (L) | 1472+/−149 | 532+/−43 | 940+/−143 |
| FIG. 16 (HSA) | 5360+/−404 | 5674+/−332 | −314+/−522 |
| FIG. 18 (HSA) | 3126+/−236 | 3616+/−211 | −490+/−317 |

TABLE 63

L and HSA Uptake of an ACCUVUE Contact Lens Material Utilizing Summing Peak Ratios from MALDI Mass Spectra

| Calibration Curve | Total Protein(ug) | Remaining Protein(ug) | Protein Uptake |
|---|---|---|---|
| FIG. 11 (L) | 1498+/−107 | 646+/−54 | 852+/−120 |
| FIG. 13 (L) | 1472+/−105 | 620+/−52 | 852+/−117 |
| FIG. 17 (HSA) | 2531+/−152 | 2531+/−133 | 0+/−202 |
| FIG. 19 (HSA) | 2806+/−169 | 2806+/−148 | 0+/−225 |

Samples solutions labeled Total Protein and Remaining Protein were analyzed for lysozyme and albumin content by an UV calorimetric assay. The UV sample preparations for this sample set and the UV calibration curves were discussed above. The absorbences are tabulated in Tables 64. The results were applied to both the HAS and L calibration curves and the results are in Table 65. The HSA and L uptake by the ACCUVUE contact lenses were determined by subtracting the Total Protein results from the Remaining Protein results. These results are also included in Table 65.

TABLE 64

HSA and L Mixture UV Raw Data

| Sample | Total Protein Absorbance | Remaining Protein Absorbence |
|---|---|---|
| Sample 1 | 0.441 | 0.363 |
| Sample 2 | 0.451 | 0.365 |
| Sample 3 | 0.431 | 0.332 |
| Sample 4 | 0.449 | 0.357 |
| Sample 5 | 0.444 | 0.366 |
| Sample 6 | 0.448 | 0.365 |
| Mean+/−SD | 0.444+/−0.007 | 0.358+/−0.013 |

TABLE 65

Protein Uptake by UV Method

| Calibration Curve | Total Protein | Remaining Protein | Protein Uptake |
|---|---|---|---|
| L | 3363+/−53 | 2684+/−97 | 679+/−111 |
| HSA | 5544+/−87 | 4393+/−160 | 1151+/−182 |

This UV method can not discriminate between proteins so the overall protein content was either 697 ug, L calibration curve, or 1151 ug with the HSA calibration curve. Since the solution was a mixture of the two proteins, the actual result falls between 1151–697 ug. The MALDI method can discriminate between proteins and those results, Tables 62 and 63, fall within the UV range for protein uptake.

Surface MALDI Results

The contact lens, from each of the solutions: L, HSA, La and the HSA, L mixtures, were dried, covered with a solution containing matrix and CC (IS). There was no protein detected, except the internal standard, for lenses soaked in the HSA, La or the mixture of L and HSA. It was expected that there was no HSA detected for the HSA only sample since no HSA was absorbed into the contact lens. The contact lens absorbed about 400 ug of La but none was detected by surface MALDI analyses. These calibration curves do not account for interaction between the lens and the La because they were constructed from results performed by standard matrix-MALDI analysis. In fact it has been reported by Nelson et. al. (Nelson, K. D., Effects on Protein-Surface Interactions on Protein Ion Signal in MALDI Mass Spectrometry., Anal. Chem. 1999, 71, 268–272) that Protein-surface interaction has an effect on MALDI ion signal. L was detected for lenses deposited in the L solution only. The first sample set contained 14+/−2.6 ug of L at the surface. The second set contained 31+/−6.0 ug of L.

Protein Uptake into the ACCUVUE Contact Lens Material

The ACCUVUE contact lens material is composed of 98% hydroxyethylmethacrylate (HEMA) and 2% methacrylic acid. This material is anionically charged in the buffered MOPS solution, pH=7.2. It has a propensity to interact with cationic biomolecules. L and La were the only proteins to absorbed/adsorbed into or onto this material. L and La have polyisoelectric constants (pI) of 11.0 and 8.7, respectively. They are cationically charged in a buffered solution with a pH of 7.2 and interacted with the anionic lens material. HSA has a pI of 4.5 so at a pH of 7.0 it has a negative charge. This biomolecule did not absorb or adsorb into the negatively charged contact lens material.

Application of the CIM Equation

The next few sections will discuss the application of the CIM equation for four proteins, Al, CA, M and αL. The sample preparations for each protein were outlined in the experimental section above.

The Application of the CIM Equation to Al

Figure 34:
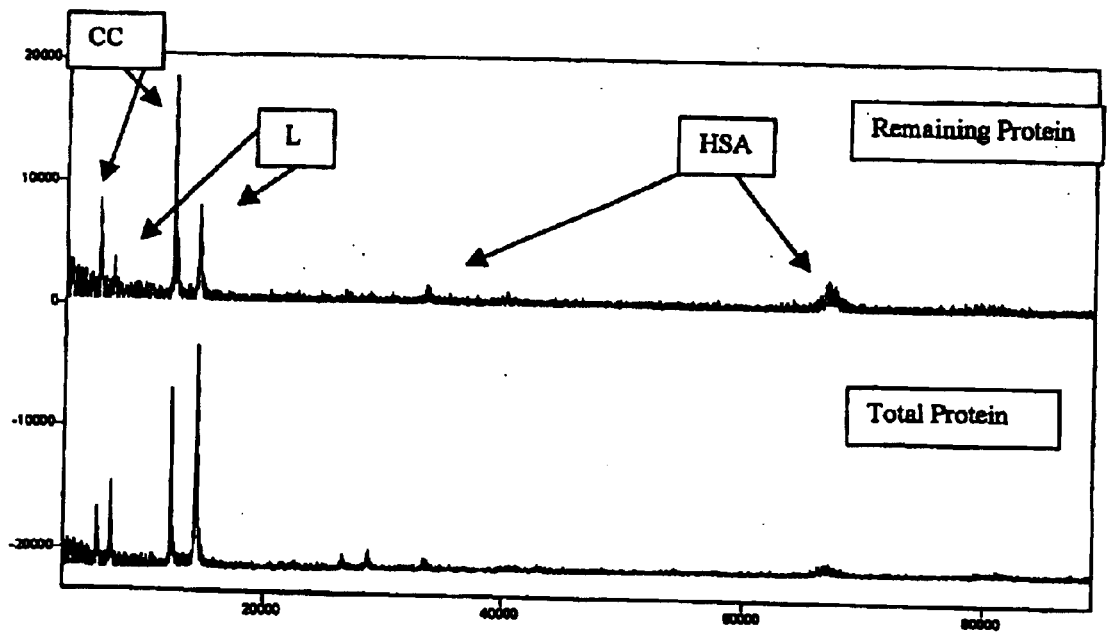

Samples were analyzed by MALDI to apply the CIM equation for Al utilizing CC as the IS. The MALDI mass spectrum of Al and CC is shown in FIG. 34. The MALDI analyses yielded many peaks in the mass spectrum. The Al related ions were $(Al)^{+2}$ at 33.9KD, $(Al)^{+1}$ at 65.7KD, $(2Al)^{+1}$ at 131.4KD (not shown) and finally $(3Al)^{+1}$ at 197.1KD (not shown). The Cytochrome C (CC) related ions were $(CC)^{+2}$ at 6.1KD, $(CC+MOPS\ buffer)^{+2}$ at 6.2KD, $(CC)^{+1}$ at 12.2KD and $(CC+MOPS\ buffer)^{+1}$ at 12.4KD. The molecular ion region was expanded in FIG. 34 to better illustrate the CC molecular ion peaks.

The sample preparations for these results are as discussed above. There were three known solutions prepared. The samples were analyzed by MALDI. The CIM equation was applied to the results and the protein content was determined. The results were then compared to the known protein content.

The first solution, solution 1, contained 3000 ug in 1 ml of solution. Two micoliters of this solution was mixed with 40 ul of matrix and 2 ul of the internal standard (0.546 pmole/ul), dried and analyzed by MALDI. There were many forms of the CIM equation based on rearrangement. The form utilized in this discussion was equation 2.

$$\sum I(AI)/\sum I(CC) = (2.5/MW(AI)) \times ([AI]/[CC]) \qquad 2$$
$$\ \ \ \ \ Y\ \ \ \ \ \ \ \ \ \ \ \ \ \ \ \ \ \ \ \ \ \ \ \ \ =\ \ \ \ \ \ \ \ \ \ M\ \ \ \ \ \ \ \ \ \ \ \ \ \ \ \ X$$

Y or the sum of the intensity ratios was determined from the spectra to be 0.142+/−0.014. The calculated slope is 2.5/65.7 or 0.038. The X is $([Al]/[5.46\times10^{-13}\ mole/ul])$. With one unknown [Al], the concentration of Al was calculated to be $2.04\times10^{-12}$ mole/ul. To determine the actual amount, in microgram, in the original solution involves multiplying this answer by the dilution factor, 44/2, the number of micoliters of the original solution, 1000, the molecular weight of Al, 65,667 g/mole, converting grams to milligrams, 1000 and finally converting milligrams to micrograms, 1000. The CIM equation predicted that the solution containing a theoretical amount of 3000 ug had 2960+/−300 ug of Al. This experiment was repeated twice more. The second and third solutions, solutions 2 and 3, both contained 2800 ug in 940 ul of solution. The sums of the peak intensity ratios were 0.146+/−0.010 and 0.140+/−0.016, respectively. The CIM equation predicts that solution 2 contained 2850+/−195 ug of Al while solution 3 contained 2733+/−312 ug of Al.

TABLE 66

Al Results Utilizing the CIM Equation

| Solution | Theoretical(ug) | CIM Prediction(ug) |
|---|---|---|
| Solution 1 | 3000 | 2960+/−300 |
| Solution 2 | 2800 | 2850+/−195 |
| Solution 3 | 2800 | 2733+/−312 |

The Application of the CIM Equation to Carbonic Anhydrase (CA)

Figure 35:
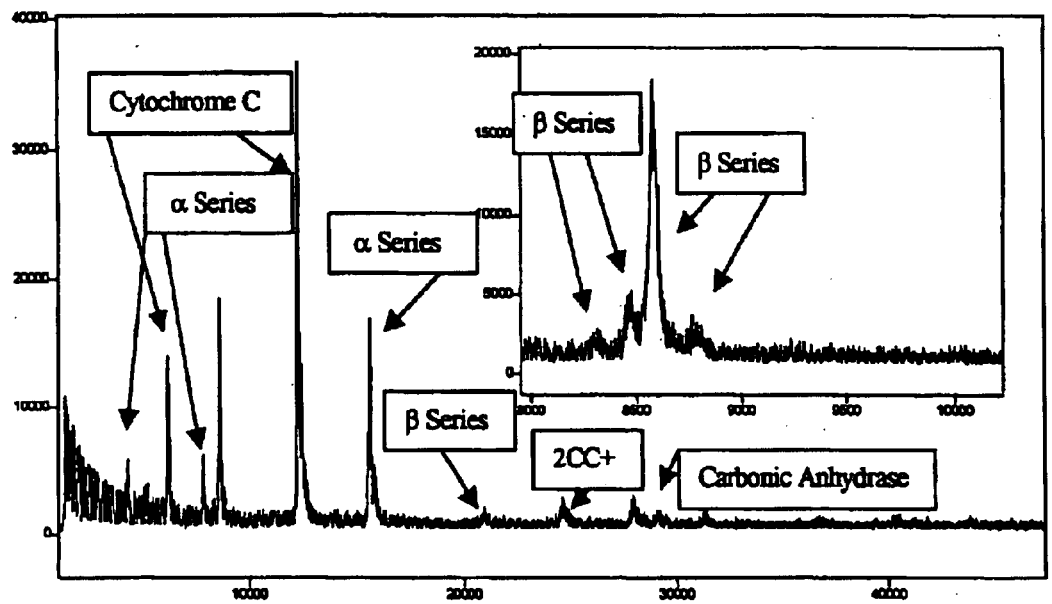

Samples were analyzed by MALDI to apply the CIM equation for CA utilizing CC as the IS. The MALDI mass spectrum of CA and CC was shown in FIG. 35. The MALDI analyses yielded many peaks in the mass spectra. The CA MALDI mass spectrum revealed that this protein fragmented into two series of peaks, the α and β series. The α series contains the molecular ion $(CA)^+$ at 29.1KD, an $(\alpha)^+$ fragment at 15.6KD, the same $(\alpha+MOPS\ buffer)^+$ fragment plus a buffer at 15.8KD and the $(\alpha)^{+2}$ doubly charged related peaks at 7.8KD and 7.9KD. The β series contains the molecular ion (CA) at 29.1KD, the molecular ion minus 8.5KD at 20.6KD, finally a series of peaks at 8.8KD, 8.5KD, 8.4KD and 8.3KD. The 8.5KD β series region was expanded in FIG. 35 to better illustrate these ion peaks. The CC related ions were $(CC)^{+2}$ at 6.1KD, $(CC+MOPS\ buffer)^{+2}$ at 6.2KD, $(CC)^{+1}$ at 12.2KD and $(CC+MOPS\ buffer)^{+1}$ at 12.4KD.

The sample preparations for these results were as discussed above. There were three known solutions prepared. The samples were analyzed by MALDI. The CIM equation was applied to the results and the protein content was determined. The results were then compared to the known protein content.

There were many forms of the CIM equation based on rearrangement. The form utilized in this discussion was equation 2. The Y function or $\Sigma I(CA)/\Sigma I(CC)$ involves summing the peaks of the related ions and taking the ratio. In the past with the HSA, Al, L and La, what was occurring during summation of the peak intensities was summation of all of the molecules. In this case summing all of the peaks, the α and β series, would involve summing twice as many molecules since the protein fragmented into two. In order to count all of the molecule once either the sum of the α series peaks will be used or the sum of the β series for the CA Y component of the equation.

$$\sum I(CA)/\sum I(CC) = (2.5/MW(CA)) \times ([CA]/[CC]) \qquad 2$$
$$\ \ \ \ \ Y\ \ \ \ \ \ \ \ \ \ \ \ \ \ \ \ \ \ \ \ \ \ \ \ \ =\ \ \ \ \ \ \ \ \ \ M\ \ \ \ \ \ \ \ \ \ \ \ \ \ \ \ X$$

The first solution, solution 1, contained 2100 ug in 1 ml of solution. Two micoliters of this solution was mixed with 40 ul of matrix and 2 ul of the internal standard (0.590 pmole/ul), dried and analyzed by MALDI under the conditions mentioned in section 3.2.4.3. For solution 1 the Y or the sum of the α intensity divided by the sum of the CC intensities was determined from the spectrum to be 0.506+/−0.019. The calculated slope is 2.5/29.1 or 0.086. The X is $([CA]/[5.90\times10^{-13}\ mole/ul])$. With one unknown [CA], the concentration of CA was calculated to be $3.47\times10^{-12}$ mole/ ul. To determine the actual amount, in microgram, in the original solution involves multiplying this answer by the dilution factor, 44/2, the number of micoliters of the original solution, 1000, the molecular weight of CA, 29105 g/mole, converting grams to milligrams, 1000 and finally converting milligrams to micrograms, 1000. The CIM equation predicted that the solution containing a theoretical amount of 2100 ug had 2222+/−83 ug of CA. For solution 1 the Y or the sum of the β intensity ratios was determined from the spectrum to be 0.468+/−0.036. Utilizing the same slope, internal standard concentration, dilution factor and conversion factors, the CIM equation predicts the β series solution, with theoretically 2100 ug of CA, had 2055+/−158. This experiment was repeated twice more. The second and third solutions, solutions 2 and 3, contained theoretical amounts of 2000 ug and 2200 ug in 1000 ul of solution, respectively. The sums of the peak intensity ratios for solution 2 α and β were 0.467+/−0.028 and 0.450+/−0.025, respectively. The CIM equation predicts that solution 2 utilizing either the α or β series contained 2051+/−123 ug (α) or 1976+/−110 ug (β) of CA. The sums of the peak intensity ratios for solution 3 α and β were 0.536+/−0.041 and 0.536+/−0.070, respectively. The CIM equation predicts that solution 3 utilizing either the α or β series contained 2354+/−180 ug (cc) or 2354+/−307 ug (β) of CA.

TABLE 67

CA Results Utilizing the CIM Equation

| Solutions | Theoretical(ug) | CIM Prediction(α) | CIM Prediction(β) |
|---|---|---|---|
| Solution 1 | 2100 | 2222+/−83 | 2055+/−158 |
| Solution 2 | 2000 | 2051+/−123 | 1976+/−110 |
| Solution 3 | 2200 | 2354+/−180 | 2354+/−307 |

The Application of the CIM Equation to Myoglobin (M)

Figure 36:
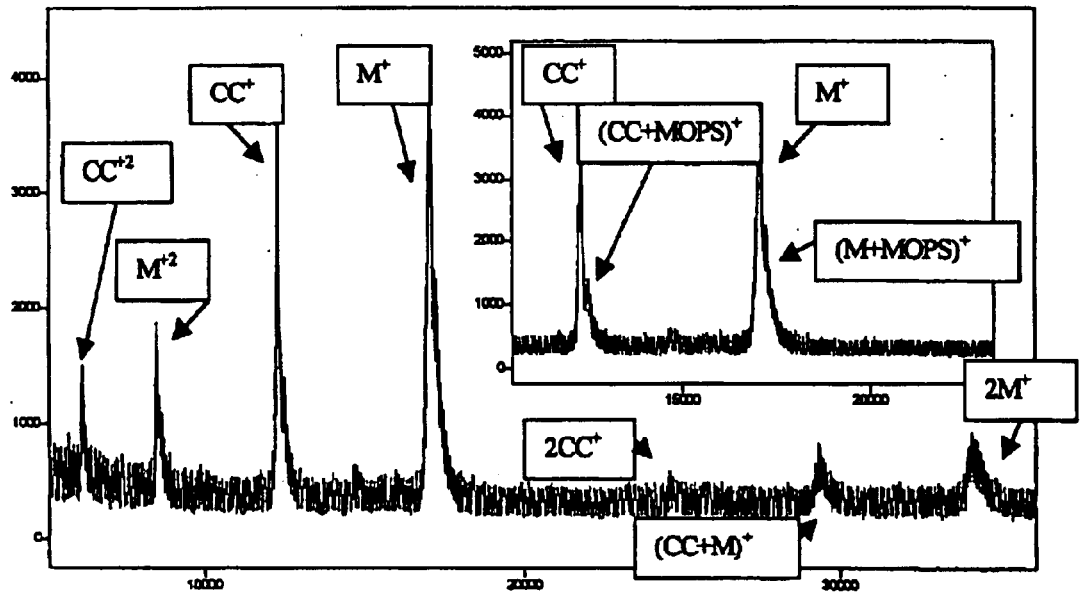

Samples were analyzed by MALDI to apply the CIM equation for M utilizing CC as the internal standard. The MALDI mass spectra of M and CC was shown in FIG. 36. The MALDI analyses yielded many peaks in the mass spectrum. The M related ions were $(M)^{+2}$ at 8.5KD, $(M+MOPS\ buffer)^{+2}$ or M plus buffer doubly charged at 8.6KD, $(M)^{+1}$ at 17.0KD, $(M+MOPS\ buffer)^{+1}$ or M plus buffer singly charged at 17.2KD, $(2M)^{+1}$ at 34.0KD and finally $(M+CC)^{+1}$ at 29.2KD. The CC related ions were $(CC)^{+2}$ at 6.1KD, $(CC+MOPS\ buffer)^{+2}$ at 6.2KD, $(CC)^{+1}$ at 12.2KD and $(CC+MOPS\ buffer)^{+1}$ at 12.4KD. The molecular ion region was expanded in FIG. 36 to better illustrate the CC and M molecular ion peaks.

The sample preparations for these results were as discussed above. There were three known solutions prepared. The samples were analyzed by MALDI. The CIM equation was applied to the results and the protein content was determined. The results were then compared to the known protein content.

There were many forms of the CIM equation based on rearrangement. The form utilized in this discussion was equation 2. This equation did not work but changing the phun factor from 2.5 to 5.5, Equation 7, resulted in an equation that predicted similar results compared to theoretical.

$$\sum_Y I(M) / \sum I(CC) = \underbrace{(2.5/MW(M))}_{M} \times \underbrace{([M]/[CC])}_{X} \qquad 2$$

-continued $$\sum_Y I(M) / \sum I(CC) = \underbrace{(5.5/MW(M))}_{M} \times \underbrace{([M]/[CC])}_{X} \qquad 7$$

The first solution, solution 1, contained 1000 ug (90% purity) in 1 ml of solution. Two micoliters of this solution was mixed with 40 ul of matrix and 2 ul of the internal standard (0.572 pmole/ul), dried and analyzed by MALDI under the conditions mentioned in section 3.2.4.5. Y or the sum of the intensity ratios was determined from the spectrum to be 1.37+/−0.029. The calculated slope is 5.5/16.95 or 0.32. The X is $([M]/[5.72 \times 10^{-13}\ mole/ul])$. With one unknown [M], the concentration of M was calculated to be $2.45 \times 10^{-12}$ mole/ul. To determine the actual amount, in microgram, in the original solution involves multiplying this answer by the dilution factor, 44/2, the number of micoliters of the original solution, 1000, the molecular weight of M, 16,951 g/mole, converting grams to milligrams, 1000 and finally converting milligrams to micrograms, 1000. The CIM equation predicted that the solution containing a theoretical amount of 900 ug had 915+/−20 ug of M. This experiment was repeated twice more. The second and third solutions, solutions 2 and 3, contained 1080 ug in 1000 ul of solution and 990 ug in 1000 ul of solution, respectively. The sums of the peak intensity ratios were 1.42+/−0.050 and 1.44+/−0.11, respectively. The CIM equation predicts that solution 2 contained 949+/−33 ug of M while solution 3 contained 962+/−74 ug of M.

TABLE 68

M Results Utilizing the CIM Equation

| Solution | Theoretical(ug) | CIM Prediction(ug) |
|---|---|---|
| Solution 1 | 900 | 915+/−20 |
| Solution 2 | 1080 | 949+/−33 |
| Solution 3 | 990 | 962+/−74 |

The Application of the CIM Equation to αLactalbumin(αL)

Figure 37:
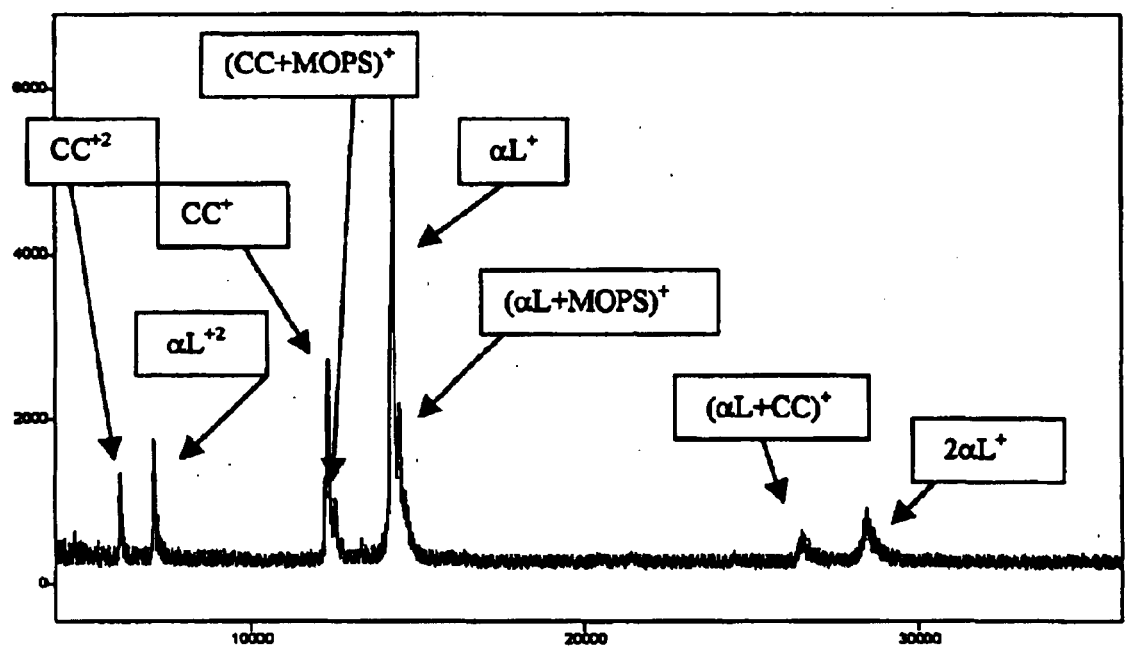

Samples were analyzed by MALDI to apply the CIM equation for αL utilizing CC as the IS. The MALDI mass spectrum of αL and CC was shown in FIG. 37. The MALDI analyses yielded many peaks in the mass spectrum. The αL related ions were $(αL)^{+2}$ at 7.15KD, $(αL+MOPS\ buffer)^{+2}$ or αL plus buffer doubly charged at 7.25KD, $(αL)^{+1}$ at 14.3KD, $(αL+MOPS\ buffer)^{+1}$ or αL plus buffer singly charged at 14.5KD, $(2αL)^{+1}$ at 28.6KD and finally $(αL+CC)^{+1}$ at 26.5KD. The CC related ions were $(CC)^{+2}$ at 6.1KD, $(CC+MOPS\ buffer)^{+2}$ at 6.2KD, $(CC)^{+1}$ at 12.2KD and $(CC+MOPS\ buffer)^{+1}$ at 12.4KD. The molecular ion region was expanded in FIG. 37 to better illustrate the CC and αL molecular ion peaks.

The sample preparations for these results were as discussed above. There were three known solutions prepared. The samples were analyzed by MALDI. The CIM equation was applied to the results and the protein content was determined. The results were then compared to the known protein content.

There were many forms of the CIM equation based on rearrangement. The form utilized in this discussion was equation 2. This equation did not work but changing the phun factor from 2.5 to 5.5, Equation 7, resulted in an equation that predicted similar results compared to theoretical.

$$\sum I(\alpha L) / \sum I(CC) = (2.5/MW(\alpha L)) \times ([\alpha L]/[CC]) \qquad 2$$
$$\quad Y \qquad = \qquad M \qquad X$$

$$\sum I(\alpha L) / \sum I(CC) = (5.5/MW(\alpha L)) \times ([\alpha L]/[CC]) \qquad 7$$
$$\quad Y \qquad = \qquad M \qquad X$$

The first solution, solution 1, contained 1200 ug (85% purity) in 1 ml of solution. Two micoliters of this solution was mixed with 40 ul of matrix and 2 ul of the internal standard (0.572 pmole/ul), dried and analyzed by MALDI under the conditions mentioned in section 3.2.4.4. Y or the sum of the intensity ratios was determined from the spectrum to be 2.24+/−0.10. The calculated slope is 5.5/14.175 or 0.39. The X is ($[\alpha L]/[5.72 \times 10^{-13}$ mole/ul]). With one unknown $[\alpha L]$, the concentration of $\alpha L$ was calculated to be $3.28 \times 10^{-12}$ mole/ul. To determine the actual amount, in microgram, in the original solution involves multiplying this answer by the dilution factor, 44/2, the number of micoliters of the original solution, 1000, the molecular weight of $\alpha L$, 14,175 g/mole, converting grams to milligrams, 1000 and finally converting milligrams to micrograms, 1000. The CIM equation predicted that the solution containing a theoretical amount of 1020 ug had 1024+/−45 ug of $\alpha L$. This experiment was repeated twice more. The second and third solutions, solutions 2 and 3, contained 935 ug in 1000 ul of solution and 935 ug in 1000 ul of solution, respectively. The sums of the peak intensity ratios were 2.07+/−0.14 and 2.09+/−0.17, respectively. The CIM equation predicts that solution 2 contained 947+/−64 ug of $\alpha L$ while solution 3 contained 958+/−79 ug of $\alpha L$.

TABLE 69

$\alpha L$ Results Utilizing the CIM Equation

| Solution | Theoretical(ug) | CIM Prediction(ug) |
|---|---|---|
| Solution 1 | 1020 | 1024+/−45 |
| Solution 2 | 935 | 947+/−64 |
| Solution 3 | 935 | 958+/−79 |

Discussion on the Phun Factor

This section will discuss the theory of why different families of proteins have different phun factors for the CIM equation when compared to CC. For example, the phun factor for proteins in family A (L, HSA, Al, La or CA), have a phun factor, when compared to CC, of 2.5(equation 2). The phun factor for proteins in family B (M and $\alpha L$) have a phun factor, when compared to CC, of 5.5 (equation 7). The phun factor is an ionization factor that compensates for differences in ionization between families.

The sequence of the proteins in each of the families was first explored for differences and similarities. It was discovered that proteins in family A had an abundance of arginine (R) and lysine (K) while family B was arginine deficient. These are two of the three basic amino acids. The other basic amino acid is histidine (H). The basic amino acids are of interest because in the positive MALDI mass spectrum, these are the most likely groups that carry the cation. The pKa of the amino acid side groups of arginine, lysine and histidine are 12.5, 10.0 and 6.0, respectively. Since arginine has the highest pKa, it will most likely cationize during the MALDI ionization process. So if a protein is arginine deficient then the protein will ionize on the amino acid that has the next highest pKa, lysine. So it is theorized that family A ionizes on arginine and family B ionizes on lysine. There are, of course, other possible cationic sites on proteins; the N-terminus (pKa=9.0–10.6) or charged inorganic metals. This is where family C (cytochome C) belongs. Cytochome C is arginine deficient, lysine rich and contains a heme group with inorganic iron. Initially it was thought that this protein was a family B protein because its amino acid content is similar to family B's description and is so similar to myoglobin. It is theorized that cytochrome C is partially ionizing on the iron group and that the ion is preformed in solution. The iron in cytochrome C oxidized much more readily that the iron in myoglobin (Chenj, J., Terrettaz S., Blankman J I., Electrochemical Comparison of HEME Proteins by Insulated Electrode Voltammetry, Israel Journal of Chemistry, 37(2–3):259–266, 1997).

Below are the sequences for family A proteins. The results or the number of K and R are next to the protein name in the title.

Sequence for Lysozyme (Brookhaven PDB: 1931) (R=11, K=6)

Sequence for Carbonic Anhydrase(SWISS-PROT:P00921) (R=9, K=18)

Sequence for Horse Albumin(SWISS-PROT:P35747) (R=25, K=61)

Sequence for Human Albumin(SWISS-PROT:P02768) (R=27, K=60)

Sequence for Lactoferrin(SWISS-PROT:P24627) (R=37, K=54)

Below are the sequences for family B proteins. The results or the number of K and R are next to the protein name in the title.

Sequence for Myoglobin(SWISS-PROT:P02188) (R=2, K=19)

Sequence for $\alpha$Lactalbumin (Brookhaven PDB: 1 hfz) (R=1, K=12)

Below is the sequence for the internal standard CC. Since there was a phun factor when families A or B was compared to CC, it means that CC is to its own family, family C. It is believed that this protein is ionizing on the metal heme group.

Sequence for Cytochrome C (SWISS-PROT:P00006) (R=2, K=18)

The Application of the CIM Equation to M Utilizing $\alpha L$ as the IS

Samples were analyzed by MALDI to apply the CIM equation for M utilizing $\alpha L$ as the IS. Conversely, this experiment can also be applying the CIM equation to $\alpha L$ utilizing M as the IS. The MALDI mass spectrum of $\alpha L$ and M was not shown. In fact, the same peaks (ion formation) shown for M and $\alpha L$ with CC can be applied here except, of course, discounting the CC peaks or any peaks evolving from M and $\alpha L$ interactions.

The sample preparations for these results were discussed above. There were three known solutions prepared. The samples were analyzed by MALDI. The sum of the peak intensity ratios was determined from the spectrum. Then, the known concentration and MW were applied to the CIM equation and the sum of the peak intensities ratios were predicted. The predicted results and the spectrum results were then compared to each other.

There were many forms of the CIM equation based on rearrangement. The form utilized in this discussion was equation 6. Equation 6 is utilized when two proteins from the same family are being used to quantitate one or the other.

$$(MW(M) \times \Sigma I(M))/[M] = (MW(\alpha L) \times \Sigma I(\alpha L))/[\alpha L] \quad\quad 6$$

$$(\Sigma \alpha L/\Sigma M) \times (MW(M) = [\alpha L])/(MW(\alpha L) \times [M]) \quad\quad 8$$

The first solution, solution 1, contained $2.52 \times 10^{-12}$ mol/ul of M, $3.21 \times 10^{-12}$ mol/ul of $\alpha L$ and matrix. The above CIM equation, equation 8, predicts that the sum of the peak intensity ratios ($\Sigma \alpha L/\Sigma M$) equals 1.52. This was determined from by inputting the molecular weights and the above concentrations. The above solution was analyzed and the actual sum of the peak intensity ratios was taken from the MALDI spectra and determined to be 1.58+/−0.07. Two more solutions were prepared. Solution 2 contained $2.50 \times 10^{-12}$ mol/ul of M, $3.21 \times 10^{-12}$ mol/ul of ($\alpha L$ and matrix. The above CIM equation, equation 8, predicts that the sum of the peak intensity ratios ($\Sigma \alpha L/\Sigma M$) equals 1.53. This was determined from by inputting the molecular weights and the above concentrations. The above solution was analyzed and the actual sum of the peak intensity ratios was taken from the MALDI spectra and determined to be 1.53+/−0.14. Solution 3 contained $2.35 \times 10^{-12}$ mol/ul of M, $3.21 \times 10^{-12}$ mol/ul of $\alpha L$ and matrix. The above CIM equation, equation 8, predicts that the sum of the peak intensity ratios ($\Sigma \alpha L/\Sigma M$) equals 1.63. This was determined from by inputting the molecular weights and the above concentrations. The above solution was analyzed and the actual sum of the peak intensity ratios was taken from the MALDI spectra and determined to be 1.57+/−0.06. Table 70 provides a summary of the above data.

TABLE 70

M and $\alpha L$ Results Utilizing the CIM Equation

| Solution | Actual ($\Sigma \alpha L/\Sigma M$) | CIM Prediction ($\Sigma \alpha L/\Sigma M$) |
|---|---|---|
| Solution 1 | 1.58 ± 0.07 | 1.52 |
| Solution 2 | 1.53 ± 0.14 | 1.53 |
| Solution 3 | 1.57 ± 0.06 | 1.63 |

The Application of the CIM Equation to Al Utilizing L as the IS

Samples were analyzed by MALDI to apply the CIM equation for Al utilizing L as the IS. Conversely, this experiment can also be applying the CIM equation to L utilizing Al as the IS. The MALDI mass spectra of Al and L is not shown. In fact, the same peaks (ion formation) shown for L and Al with CC can be applied here except, of course, discounting the CC peaks and peak evolving from L and Al peaks.

The sample preparations for these results were as discussed above. There were three known solutions prepared. The samples were analyzed by MALDI. The sum of the peak intensity ratios was determined from the spectrum. Then, the known concentration and MW were applied to the CIM equation and the sum of the peak intensity ratios was predicted. The predicted results and the spectrum results were then compared to each other.

There were many forms of the CIM equation based on rearrangement. The form utilized in this discussion was equation 6. Equation 6 is utilized when two proteins from the same family are being used to quantitate one or the other.

$$(MW(Al) = \Sigma I(Al))/[Al] = (MW(L) \times \Sigma I(L))/[L] \quad\quad 6$$

$$(\Sigma(Al)/\Sigma(L) = (MW(L) \times [Al])/(MW(Al) \times [L]) \quad\quad 8$$

The first solution, solution 1, contained $2.59 \times 10^{-12}$ mol/ul of L, $3.94 \times 10^{-12}$ mol/ul of Al and matrix. The above CIM equation, equation 8, predicts that the sum of the peak intensity ratios ($\Sigma(Al)/\Sigma(L)$) equals 0.365. This was determined from by inputting the molecular weights and the above concentrations. The above solution was analyzed and the actual sum of the peak intensity ratios was taken from the MALDI spectrum and determined to be 0.298+/−0.060. Two more solutions were prepared. Solution 2 contained $2.60 \times 10^{-12}$ mol/ul of L, $3.94 \times 10^{-12}$ mol/ul of Al and matrix. The above CIM equation, equation 8, predicts that the sum of the peak intensity ratios ($\Sigma(Al)/\Sigma(L)$) equals 0.330. This was determined from by inputting the molecular weights and the above concentrations. The above solution was analyzed and the actual sum of the peak intensity ratios was taken from the MALDI spectrum and determined to be 0.268+/−0.036. Solution 3 contained $2.77 \times 10^{-12}$ mol/ul of L, $4.36 \times 10^{-12}$ mol/ul of Al and matrix. The above CIM equation, equation 8, predicts that the sum of the peak intensity ratios ($\Sigma(Al)/\Sigma(L)$) equals 0.342. This was determined from by inputting the molecular weights and the above concentrations. The above solution was analyzed and the actual sum of the peak intensity ratios was taken from the MALDI spectrum and determined to be 0.281+/−0.053. Table 71 provides a summary of the above data.

TABLE 71

L and Al Results Utilizing the CIM Equation

| Solution | Actual ($\Sigma Al/\Sigma L$) | CIM Prediction ($\Sigma Al/\Sigma L$) |
|---|---|---|
| Solution 1 | 0.298 ± 0.060 | 0.365 |
| Solution 2 | 0.268 ± 0.036 | 0.330 |
| Solution 3 | 0.281 ± 0.053 | 0.342 |

The CIM predictions were 20% different than actual intensity ratios. There are a few possible reasons for these results; other desorption factors, instrumental transmission differences or detector sensitivity. Thus, as a general rule, the molecular weights have to be within 30KD of one another.

The Application of the CIM Equation to Protein Mixtures

The CIM was applied to protein mixtures. Only small molecular weight protein mixtures (10–30 kD) with total protein concentrations less that 5.0 pmol/$\mu$l resulted in peak intensity ratios in good agreement with the CIM, Table 72. The appropriate CIM equation containing the correct phun factor was used for the calculation in Table 72.

TABLE 72

|  | A | B | C | D | E | F |
|---|---|---|---|---|---|---|
| Carbonic Anhydrase | 2.08 | 0.29 | 0.31 +/− 0.022 | 1.98 | 0.38 | 0.37 +/− 0.021 |
| Lysozyme | 1.31 | 0.37 | 0.33 +/− 0.015 | 1.19 | 0.46 | 0.46 +/− 0.026 |

TABLE 72-continued

| | A | B | C | D | E | F |
|---|---|---|---|---|---|---|
| Myoglobin | 0.83 | 0.44 | 0.46 +/− 0.025 | 0.66 | 0.47 | 0.46 +/− 0.016 |
| Cytochrome C (IS) | 0.60 | 1.00 | N/A | 0.44 | 1.00 | N/A |

A = concentration in pmol/μl for proteins in run #1
B = peak intensity ratios (Sample Protein/Cytochrome C) predicted by the RQE equation
C = actual spectra peak intensity ratios
D–F is run #2

The Application of the CIM Equation to Oligonucleotide Samples

Oligonucleotides $(ATCG)_5$-TC and $(ATCG)_7$-AC were applied to the CIM equation, equation 6, with concentrations of 12.3 pmol/μl and 9.0 pmol/μl, respectively. The CIM equation predicts the peak intensity ratio of the $(ATCG)_5$-TC to $(ATCG)_7$-AC be 1.8. In negative mode the ratio was 1.81+/−0.11 and in positive mode 1.77+/−0.13. Oligonucleotides $(ATCG)_5$-TC and $(ATCG)_7$-AC were applied to the CIM equation with concentrations of 4.1 pmol/μl and 4.5 pmol/μl, respectively. The CIM equation predicts the peak intensity ratio of the $(ATCG)_5$-TC to $(ATCG)_7$-AC be 1.2. In negative mode the ratio was 1.31+/−0.15 and in positive mode no peaks were detected.

CONCLUSION

Matrix-Assisted Laser Desorption Ionization (MALDI) mass spectrometry is a bioanalytical technique typically used to qualitatively analyze peptides and proteins. Although a very powerful tool in qualitative analysis with femtomole and lower detection limits, the major disadvantage to MALDI is the difficulty in providing quantitative information due to matrix and sample sensitivities. The present invention overcomes obstacles, and the quantitative identification of proteins absorbed into contact lenses was examined by MALDI-time of flight (ToF). In these experiments, MALDI-ToF was performed on a PerSeptive Voyager-DE STR, with detection set in the linear mode. Calibration curves were constructed for HSA, La, and L utilizing CC as an internal standard. The calibration curves were used to quantify the protein uptake in ACCUVUE, a contact lens material produced by Johnson & Johnson. For all proteins, a linear concentration range of 1–7 pmol/uL was observed for the constructed calibration curves. Correlation coefficients with $R^2 > 0.999$ were routinely obtained. The MALDI-ToF results were compared to an UV calorimetric assay that has been used previously to quantify protein uptake into ACCUVUE lenses. MALDI-ToF and the UV assay also showed similar uptakes for L, La and HSA into the contact lenses, though in the case of HSA, neither technique detected any uptake of protein by the contact lenses. Of course, a major advantage of MALDI-ToF over UV colorimetry is the qualitative identification of individual analytes, whereas UV colorimetry is capable only of determining total protein uptake. Finally, the quantitative MALDI-ToF method was further developed according to this invention, so as to the eliminate calibration curves and the implementation of a simple equation, the CIM equation. It was shown that there are families of proteins and that these families are dependent on the protein amino acid content. To determine the concentration of a sample protein, the CIM equation is utilized with an internal standard (protein) from the same family as the sample protein. In other words, the two proteins ionize on the same amino acid. The CIM equation is below.

$$(MW(Sample) \times \Sigma I(Sample))/[Sample] = (MW(IS) \times \Sigma I(IS))/[IS]$$

IS=Internal Standard

The CIM equation works well (1σ), although the assumptions or general rules that are discussed here should generally be followed.

Other Reference

Griesser, H. J., Study of Protein Adsorption at Monolayer and Sub-Monolayer Levels by Surface-MALDI Spectroscopy, Society for biomaterials, 1998, San Diego, Calif.

I claim:

1. A method of quantitatively analyzing a sample analyte, selected from peptides, proteins and digest fragments of sample peptide or sample protein comprising:

performing matrix-assisted laser desorption ionization mass spectrometry on the sample analyte and an internal standard, and comparing signal intensities of the sample analyte with signal intensities of the internal standard, wherein the sample analyte and the internal standard are compared according to the following equation:

$$(MW(Sample) \times \Sigma I(Sample))/[Sample] = (MW(IS) \times \Sigma I(IS))/[IS]$$

where MW designates molecular weight, ΣI designates sum of peak intensities, brackets designate concentration, and IS designates internal standard, and wherein the sample analyte and the internal standard are ionized primarily on the same functional group.

2. The method of claim 1, wherein the internal standard is selected from a biomolecule and a synthetic molecule.

3. A method of quantitatively analyzing a sample analyte, selected from peptides, proteins and digest fragments of sample peptide or sample protein comprising:

performing matrix-assisted laser desorption ionization mass spectrometry on the sample analyte and an internal standard, and comparing signal intensities of the sample analyte with signal intensities of the internal standard, wherein the sample analyte and the internal standard are compared according to the following equation:

$$(MW(Sample) \times \Sigma I(Sample))/[Sample] = (MW(IS) \times \Sigma I(IS))/[IS]*C$$

where MW designates molecular weight, ΣI designates sum of peak intensities, brackets designate concentration, IS designates internal standard, and wherein the sample analyte and the internal standard are ionized on different functional groups, and constant C corrects for a difference in ionization efficiencies.

4. The method of claim 1, wherein matrix-assisted laser desorption ionization time-of-flight mass spectrometry is performed on the sample analyte.

* * * * *